US012612363B2

(12) United States Patent
Patrick et al.

(10) Patent No.: US 12,612,363 B2
(45) Date of Patent: Apr. 28, 2026

(54) RECRYSTALLISATION OF 5-METHOXY-N,N-DIMETHYL-TRYPTAMINE(5-MEO-DMT)

(71) Applicant: GH RESEARCH IRELAND LIMITED, Dublin (IE)

(72) Inventors: Leonard Gerard Francis Patrick, Northumberland (GB); Shaun Neil Robinson, Northumberland (GB); Theis Terwey, Berlin (DE)

(73) Assignee: GH RESEARCH IRELAND LIMITED, Dublin (IE)

( * ) Notice: Subject to any disclaimer, the term of this patent is extended or adjusted under 35 U.S.C. 154(b) by 944 days.

(21) Appl. No.: 17/620,854

(22) PCT Filed: Jun. 19, 2020

(86) PCT No.: PCT/EP2020/067113
§ 371 (c)(1),
(2) Date: Dec. 20, 2021

(87) PCT Pub. No.: WO2020/254584
PCT Pub. Date: Dec. 24, 2020

(65) Prior Publication Data
US 2022/0324802 A1 Oct. 13, 2022

(30) Foreign Application Priority Data
Jun. 19, 2019 (EP) .................................... 19181211

(51) Int. Cl.
*C07D 209/16* (2006.01)

(52) U.S. Cl.
CPC ........ *C07D 209/16* (2013.01); *C07B 2200/13* (2013.01)

(58) Field of Classification Search
CPC .................................................... C07D 209/16
See application file for complete search history.

(56) References Cited

U.S. PATENT DOCUMENTS 5,578,724 A * 11/1996 Haehl .................... A61P 17/02 544/335
6,513,524 B1 2/2003 Storz
7,458,374 B2 12/2008 Hale
7,485,285 B2 2/2009 Rabinowitz et al.
8,822,702 B2 9/2014 Berens et al.
9,370,629 B2 6/2016 Damani et al.
9,687,487 B2 6/2017 Hodges et al.
10,519,175 B2 12/2019 Londesbrough et al.
10,668,058 B2 6/2020 Rose et al.
11,518,742 B2 12/2022 Feilding-Mellen et al.
11,697,638 B2 7/2023 Rands et al.
11,773,063 B1 10/2023 Gray et al.
12,172,960 B2 12/2024 Northen et al.
2005/0282911 A1 12/2005 Hakkarainen et al.
2007/0122353 A1 5/2007 Hale et al.
2007/0178052 A1 8/2007 Rabinowitz
2007/0286816 A1 12/2007 Hale et al.
2008/0029099 A1 2/2008 Storz
2008/0311176 A1 12/2008 Hale et al.
2009/0078253 A1 3/2009 Bao
2010/0144784 A1 6/2010 Schmelzer et al.
2010/0166889 A1 7/2010 Sanfilippo
2011/0171141 A1 7/2011 Kellerman et al.
2011/0244020 A1 10/2011 Hale et al.
2011/0308521 A1 12/2011 Kofford
2012/0107396 A1 5/2012 Khan
2013/0032139 A1 2/2013 Hale et al.
2014/0060525 A1 3/2014 Hale et al.
2014/0065219 A1 3/2014 Bosch et al.
2014/0350064 A1 11/2014 Chen
2016/0346249 A1 12/2016 Mckinney et al.
2016/0374937 A1 12/2016 Hale et al.
2019/0336437 A1 11/2019 Hale et al.
2020/0069896 A1 3/2020 Bourque
2020/0147038 A1 5/2020 Russ et al.
2020/0397752 A1 12/2020 Perez-Castillo et al.
2021/0146067 A1 5/2021 Buchberger
(Continued)

FOREIGN PATENT DOCUMENTS

AU 2020225410 8/2021
AU 2020225766 8/2021
(Continued)

OTHER PUBLICATIONS

PubChem CID 1832, National Center for Biotechnology Information. PubChem Compound Summary for CID 1832, N, N-Dimethyl-5-methoxytryptamine. https://pubchem.ncbi.nlm.nih.gov/compound/N_N-Dimethyl-5-methoxytryptamine. Accessed Jan. 13, 2025, create date Mar. 25, 2005. (Year: 2005).*
Detoisien et al., Organic Process Research & Development, 2009, 13, pp. 1338-1342. (Year: 2009).*
Lyons T, Carhart-Harris RL. "Increased nature relatedness and decreased authoritarian political views after psilocybin for treatment-resistant depression." J Psychopharmacol. 2018,32(7):811-819.
Lyons T, Carhart-Harris RL. "More Realistic Forecasting of Future Life Events After Psilocybin for Treatment-Resistant Depression." Front Psychol. 2018;9:1721.
Mack JP, Mulvena DP, Slaytor M. "N,N-Dimethyltryptamine Production in Phalaris aquatica Seedlings: A Mathematical Model for its Synthesis." Plant Physiol. 1988,88(2):315-320.
(Continued)

*Primary Examiner* — Laura L Stockton
(74) *Attorney, Agent, or Firm* — Greenblum & Bernstein, P.L.C.

(57) ABSTRACT

A method of purifying 5-methoxy-N,N-dimethyltryptamine (5-MeO-DMT) is provided which comprises dissolving crude 5-MeO-DMT in a solvent at a temperature above room temperature, cooling the obtained solution to a temperature below room temperature to precipitate solid 5-MeO-DMT, separating the solid 5-MeO-DMT from the remaining solution and removing solvent from the crystalline 5-MeO-DMT. In the method, the solvent comprises one or more ethers and less than 5 wt % anti-solvent.

15 Claims, 2 Drawing Sheets

(56) References Cited

U.S. PATENT DOCUMENTS

| | | | |
|---|---|---|---|
| 2022/0031662 | A1 | 2/2022 | Terwey |
| 2022/0041551 | A1 | 2/2022 | Kruegel |
| 2022/0062238 | A1 | 3/2022 | Layzell et al. |
| 2022/0071958 | A1 | 3/2022 | Terwey |
| 2022/0232893 | A1 | 7/2022 | Jaeger et al. |
| 2022/0259147 | A1 | 8/2022 | Feilding-Mellen |
| 2022/0267267 | A1 | 8/2022 | Feilding-Mellen |
| 2022/0324802 | A1 | 10/2022 | Patrick et al. |
| 2022/0339139 | A1 | 10/2022 | Rao et al. |
| 2022/0354862 | A1 | 11/2022 | Barrow |
| 2022/0396552 | A1 | 12/2022 | Feilding-Mellen et al. |
| 2023/0031944 | A1 | 2/2023 | Feilding-Mellen et al. |
| 2023/0075124 | A1 | 3/2023 | Terwey |
| 2024/0101514 | A1 | 3/2024 | Gray et al. |
| 2024/0108601 | A1 | 4/2024 | Terwey et al. |
| 2024/0108602 | A1 | 4/2024 | Terwey et al. |
| 2024/0115549 | A1 | 4/2024 | Terwey et al. |
| 2024/0115550 | A1 | 4/2024 | Terwey et al. |
| 2024/0307350 | A1 | 9/2024 | Terwey |
| 2024/0327346 | A1 | 10/2024 | Chubb et al. |

FOREIGN PATENT DOCUMENTS

| | | |
|---|---|---|
| CA | 2843248 | 8/2014 |
| CA | 3221280 | 12/2022 |
| CL | 2021002173 | 1/2022 |
| CL | 2021002174 | 1/2022 |
| CN | 105636438 | 6/2016 |
| CN | 114555078 | 5/2022 |
| CO | 2021/0010882 | 1/2022 |
| CO | 2021/0010883 | 1/2022 |
| EM | 003387299-0001 | 9/2016 |
| EP | 0 933 093 | 8/1999 |
| EP | 1558251 | 8/2005 |
| EP | 1693366 | 8/2006 |
| EP | 1882487 | 1/2008 |
| EP | 1 884 254 | 2/2008 |
| EP | 19158774 | 2/2019 |
| EP | 19158774.0 | 8/2020 |
| EP | 19158806.0 | 8/2020 |
| EP | 3753923 | 12/2020 |
| EP | 3 927 337 A1 | 12/2021 |
| EP | 3927338 | 12/2021 |
| EP | 3941583 | 1/2022 |
| EP | 4349407 | 4/2024 |
| EP | 4353314 | 4/2024 |
| EP | 4464377 | 11/2024 |
| GB | 2008961.1 | 6/2020 |
| JP | 2003-137780 | 5/2003 |
| JP | 2004-531555 | 10/2004 |
| JP | 2006-516128 | 6/2006 |
| JP | 2010-532672 | 10/2010 |
| WO | 2002/048150 | 6/2002 |
| WO | 02/094216 | 11/2002 |
| WO | 2002/094218 | 11/2002 |
| WO | 2003094900 | 11/2003 |
| WO | 2004/043462 | 5/2004 |
| WO | 2005/055996 | 6/2005 |
| WO | 2008/077357 | 7/2008 |
| WO | 2011/020061 | 2/2011 |
| WO | 2014/035107 | 3/2014 |
| WO | 2014/144130 | 9/2014 |
| WO | 2015/006652 | 1/2015 |
| WO | 2016/056244 | 4/2016 |
| WO | 2017/011419 | 1/2017 |
| WO | 2017122196 | 7/2017 |
| WO | 2017/189883 | 11/2017 |
| WO | 2018/195455 | 10/2018 |
| WO | 2019/064031 | 4/2019 |
| WO | 2019/079742 | 4/2019 |
| WO | 2019/081764 | 5/2019 |
| WO | 2019/101825 | 5/2019 |
| WO | 2020/169850 | 8/2020 |
| WO | 2020/169851 | 8/2020 |
| WO | 2020/212952 | 10/2020 |
| WO | 2020/254584 | 12/2020 |
| WO | 2021/089872 | 5/2021 |
| WO | 2021/168082 | 8/2021 |
| WO | 2021/170614 | 9/2021 |
| WO | 2021/216489 | 10/2021 |
| WO | 2021/242988 | 12/2021 |
| WO | 2021/250434 | 12/2021 |
| WO | 2021/250435 | 12/2021 |
| WO | 2022/189662 | 9/2022 |
| WO | 2023/002005 | 1/2023 |
| WO | 2023/111544 | 6/2023 |
| WO | 2023/186797 | 10/2023 |
| WO | 2023/186798 | 10/2023 |
| WO | 2023/186806 | 10/2023 |
| WO | 2023/186808 | 10/2023 |
| WO | 2023/186816 | 10/2023 |
| WO | 2023/186820 | 10/2023 |
| WO | 2023/186821 | 10/2023 |
| WO | 2023/186823 | 10/2023 |
| WO | 2023/186824 | 10/2023 |
| WO | 2023/186826 | 10/2023 |
| WO | 2023/186827 | 10/2023 |
| WO | 2023/186828 | 10/2023 |
| WO | 2023/186829 | 10/2023 |
| WO | 2023/186830 | 10/2023 |
| WO | 2023/186831 | 10/2023 |
| WO | 2023/186832 | 10/2023 |
| WO | 2023/186834 | 10/2023 |
| WO | 2023/186835 | 10/2023 |
| WO | 2023/186837 | 10/2023 |

OTHER PUBLICATIONS

Majic T, Schmidt TT, Gallinat J. "Peak experiences and the after-glow phenomenon: when and how do therapeutic effects of hallucinogens depend on psychedelic experiences?" J Psychopharmacol. 2015,29(3):241-253.

Mandel LR, Walker RW. "The biosynthesis of 5-methoxy-N,N-dimethyltryptamine." Life Sciences. 1974;15(8):1457-1463.

May JA, McLaughlin MA, Sharif NA, Hellberg MR, Dean TR. "Evaluation of the ocular hypotensive response of serotonin 5-HT1A and 5-HT2 receptor ligands in conscious ocular hypertensive cynomolgus monkeys." J Pharmacol Exp Ther. 2003;306(1):301-309.

McKenna DJ, Towers GHN, Abbott FS. "Monoamine oxidase inhibitors in South American hallucinogenic plants part 2: Constituents of orally-active Myristicaceous hallucinogens." Journal of Ethnopharmacology. 1984,12(2):179-211.

Medhurst AD, Kaumann AJ. "Characterization of the 5-HT4 receptor mediating tachycardia in piglet isolated right atrium." Br J Pharmacol. 1993;110(3):1023-1030.

Minakami K, Shimizu T, Toriire Y, Fukuda T. Changes in head twitch response induced by a 5-hydroxytryptamine agonist in mice fed a low-protein diet. +-+ J Psychopharmacol. 1996,10(4):298-302.

Moreno FA, Wiegand CB, Taitano EK, Delgado PL. Safety, tolerability, and efficacy of psilocybin in 9 patients with obsessive-compulsive disorder. J Clin Psychiatry. 2006,67(11):1735-1740.

Multiple. Global Ayahausca Project. 2016.

Muthukumaraswamy SD, Carhart-Harris RL, Moran RJ, Brookes MJ, Williams TM, Errtizoe D, Sessa B, Papadopoulos A, Bolstridge M, Singh KD, Feilding A, Friston KJ, Nutt DJ. "Broadband cortical desynchronization underlies the human psychedelic state." J Neurosci. 2013;33(38):15171-15183.

N.D. Sepeda LYD, J.M. Clifton, J.P. Barsuglia, R. Lancelotta, R.R. Griffiths, A.K. Davis. "The influence of set and setting on the acute subjective effects of 5-MeO-DMT," 2018.

Nagai F, Nonaka R, Satoh Hisashi Kamimura K. "The effects of non-medically used psychoactive drugs on monoamine neurotransmission in rat brain." Eur J Pharmacol. 2007;559(2-3):132-137.

Nagata R, Izumi K. "Veratramine-induced behavior associated with serotonergic hyperfunction in mice." Jpn J Pharmacol. 1991;55(1):129-137.

Nash JF, Meltzer HY, Gudelsky GA. "Selective cross-tolerance to 5-HT1A and 5-HT2 receptor-mediated temperature and corticosterone responses." Pharmacology Biochemistry and Behavior. 1989;33(4):781-785.

(56) References Cited

OTHER PUBLICATIONS

Naurex Inc. aisoA, plc. "A Randomized, Double-blind, Placebo-controlled, Multicenter Study of Rapastinel as Adjunctive Therapy in Major Depressive Disorder"—Protocol Amendment 3; 2018.
Nichols DE. "Psychedelics." Pharmacol Rev. 2016;68(2):264-355.
Njung'e K, Handley SL. "Effects of 5-HT uptake inhibitors, agonists and antagonists on the burying of harmless objects by mice; a putative test for anxiolytic agents." Br J Pharmacol. 1991;104(1):105-112.
Nonaka R, Nagai F, Ogata A, Satoh K. "In vitro screening of psychoactive drugs by [(35)S]GTPgammaS binding in rat brain membranes." Biol Pharm Bull. 2007;30(12):2328-2333.
Nour MM, Evans L, Nutt D, Carhart-Harris RL. "Ego-Dissolution and Psychedelics: Validation of the Ego-Dissolution Inventory (EDI)." Front Hum Neurosci. 2016;10:269.
Osorio Fde L, Sanches RF, Macedo LR, Santos RG, Maia-de-Oliveira JP, Wichert-Ana L, Araujo DB, Riba J, Crippa JA, Hallak JE. "Antidepressant effects of a single dose of ayahuasca in patients with recurrent depression: a preliminary report." Rev Bras Psiquiatr. 2015;37(1):13-20.
Ott J. "Pharmacotheon" Entheogenic drugs, their plant sources and history; 1996.
Ott J. "Pharmahuasca: human pharmacology of oral DMT plus harmine." J Psychoactive Drugs. 1999;31(2):171-177.
Ott J. "Jonathan Ott Speaks." In: Hanna WBJ, ed. The Entheogen Review; 1999.
Ott J. "Pharmepena-Psychonautics: Human intranasal, sublingual and oral pharmacology of 5-methoxy-N,N-dimethyl-tryptamine." J Psychoactive Drugs. 2001;33(4):403-407.
Ott J. "Pharmanopo-psychonautics: human intranasal, sublingual, intrarectal, pulmonary and oral pharmacology of bufotenine." J Psychoactive Drugs. 2001;33(3):273-281.
Palhano-Fontes F, Andrade KC, Tofoli LF, Santos AC, Crippa JA, Hallak JE, Ribeiro S, de Araujo DB. "The psychedelic state induced by ayahuasca modulates the activity and connectivity of the default mode network." PLoS One. 2015;10(2):e0118143.
Palhano-Fontes et al. "Rapid antidepressant effects of the psychedelic ayahuasca in treatment-resistant depression: a randomised placebo-controlled trial." bioRxiv.org Aug. 15, 2017.
Palma-Conesa AJ, Ventura M, Galindo L, Fonseca F, Grifell M, Quintana P, Fornis I, Gil C, Farre M, Torrens M. "Something New about Something Old: A 10-Year Follow-Up on Classical and New Psychoactive Tryptamines and Results of Analysis." J Psychoactive Drugs. 2017;49(4):297-305.
Passie T, Seifert J, Schneider U, Emrich HM. "The pharmacology of psilocybin." Addict Biol. 2002;7(4):357-364.
Peto K, Nemeth N, Mester A, Magyar Z, Ghanem S, Somogyi V, Tanczos B, Deak A, Bidiga L, Frecska E, Nemes B. "Hemorheological and metabolic consequences of renal ischemia-reperfusion and their modulation by N,N-dimethyl-tryptamine on a rat model." Clin Hemorheol Microcirc. 2018;70(1):107-117.
Puxty DJ, Ramaekers JG, de la Torre R, Farre M, Pizarro N, Pujadas M, Kuypers KPC. "MDMA-Induced Dissociative State not Mediated by the 5-HT2A Receptor." Front Pharmacol. 2017;8:455.
Queiroz MM, Marti G, Queiroz EF, Marcourt L, Castro-Gamboa I, Bolzani VS, Wolfender JL. "LC-MS/MS quantitative determination of Tetrapterys mucronata alkaloids, a plant occasionally used in ayahuasca preparation." Phytochem Anal. 2015;26(3):183-188.
Ramabadran K, Jacob JJ. "Effects of various serotoninergic agonists and an antagonist on a nociceptive reaction in mice." Jpn J Pharmacol. 1982;32(6):1059-1065.
Rattan S, Goyal RK. "Effects of 5-hydroxytryptamine on the lower esophageal sphincter in vivo: evidence for multiple sites of action." J Clin Invest. 1977;59(1):125-133.
Ray TS. "Psychedelics and the human receptorome." PLoS One. 2010;5(2):e9019.
Rebec GV, Curtis SD. "Reciprocal changes in the firing rate of neostriatal and dorsal raphe neurons following local infusions or systemic injections of D-amphetamine: evidence for neostriatal heterogeneity." The Journal of Neuroscience. 1983;3(11):2240-2250.
Rènyi L. "Ejaculations induced by p-chloroamphetamine in the rat." Neuropharmacology. 1985;24(8):697-704.
Renyi L. "The effect of selective 5-hydroxytryptamine uptake inhibitors on 5-methoxy-N,N-dimethyltryptamine-induced ejaculation in the rat." Br J Pharmacol. 1986;87(4):639-648.
Renyi L. "The effects of monoamine oxidase inhibitors on the ejaculatory response induced by 5-methoxy-N,N-dimethyltryptamine in the rat." Br J Pharmacol. 1986;88(4):827-835.
Riba J. "Human Pharmacology of Ayahuasca;" 2003.
Riba J, McIlhenny EH, Bouso JC, Barker SA. "Metabolism and urinary disposition of N,N-dimethyltryptaminc after oral and smoked administration: a comparative study." Drug Test Anal. 2015;7(5):401-406.
Riba J, Valle M, Urbano G, Yritia M, Morte A, Barbanoj MJ. "Human pharmacology of ayahuasca: subjective and cardiovascular effects, monoamine metabolite excretion, and pharmacokinetics." J Pharmacol Exp Ther. 2003;306(1):73-83.
Rickli A, Moning OD, Hoener MC, Liechti ME. "Receptor interaction profiles of novel psychoactive tryptamines compared with classic hallucinogens." Eur Neuropsychopharmacol. 2016;26(8):1327-1337.
Riga MS, Bortolozzi A, Campa L, Artigas F, Celada P. "The serotonergic hallucinogen 5-methoxy-N,N-dimethyltryptamine disrupts cortical activity in a regionally-selective manner via 5-HT(1A) and 5-HT(2A) receptors." Neuropharmacology. 2016; 101:370-378.
Riga MS, Llado-Pelfort L, Artigas F, Celada P. "The serotonin hallucinogen 5-MeO-DMT alters cortico-thalamic activity in freely moving mice: Regionally-selective involvement of 5-HT1A and 5-HT2A receptors." Neuropharmacology. 2017.
Riga MS, Soria G, Tudela R, Artigas F, Celada P. "The natural hallucinogen 5-MeO-DMT, component of Ayahuasca, disrupts cortical function in rats: reversal by antipsychotic drugs." Int J Neuropsychopharmacol. 2014;17(8):1269-1282.
Rogawaski MA, Aghajanian GK. "Serotonin autoreceptors on dorsal raphe neurons: structure-activity relationships of tryptamine analogs." The Journal of Neuroscience. 1981;1(10):1148-1154.
Roseman L, Demetriou L, Wall MB, Nutt DJ, Carhart-Harris RL. "Increased amygdala responses to emotional faces after psilocybin for treatment-resistant depression." Neuropharmacology. 2017.
Roseman L, Leech R, Feilding A, Nutt DJ, Carhart-Harris RL. "The effects of psilocybin and MDMA on between-network resting state functional connectivity in healthy volunteers." Front Hum Neurosci. 2014;8:204.
Roseman L, Nutt DJ, Carhart-Harris RL. "Quality of Acute Psychedelic Experience Predicts Therapeutic Efficacy of Psilocybin for Treatment-Resistant Depression." Front Pharmacol. 2017;8:974.
Ross S, Bossis A, Guss J, Agin-Liebes G, Malone T, Cohen B, Mennenga SE, Belser A, Kalliontzi K, Babb J, Su Z, Corby P, Schmidt BL. "Rapid and sustained symptom reduction following psilocybin treatment for anxiety and depression in patients with life-threatening cancer: a randomized controlled trial." J Psychopharmacol. 2016;30(12):1165-1180.
Roth BL. "High-affinity agonist binding is not sufficient for agonist efficacy at 5-hydroxytryptamine2A receptors: evidence in favor of a modified ternary complex model." 1997.
Rucker JJ, Jelen LA, Flynn S, Frowde KD, Young AH. "Psychedelics in the treatment of unipolar mood disorders: a systematic review." J Psychopharmacol. 2016;30(12):1220-1229.
Rucker JJH, Iliff J, Nutt DJ. "Psychiatry & the psychedelic drugs. Past, present & future." Neuropharmacology. 2017.
Santos S. "Ayahuasca and Psychosis." 2011.
Schenberg EE, Alexandre JF, Filev R, Cravo AM, Sato JR, Muthukumaraswamy SD, Yonamine M, Waguespack M, Lomnicka I, Barker SA, da Silveira DX. "Acute Biphasic Effects of Ayahuasca." PLoS One. 2015;10(9):e0137202.
Schmid JT, Jungaberle H, Verres R. "Subjective Theories about (Self-)Treatment with Ayahuasca. Anthropology of Consciousness." 2010;21(2):188-204.
3$^{rd}$ Party Observation filed in EP Patent Application No. EP 20210711477, Sep. 22, 2023.

(56) References Cited

OTHER PUBLICATIONS

Rätsch, C, Encyclopedia of Psychoactive Plants: Ethnopharmacology and Its Applications, "5-MeO-DMT", p. 1822, 2005.
Quora, "Can one vaporize DMT/5-MeO-DMT in a marijuana vaporizer?", www.Quora.com, Aug. 22, 2014, https://www.quora.com/Can-one-vaporize-DMT-5-MeO-DMT-in-a-marijuana-vaporizer.
Third Party Submission filed in U.S. Appl. No. 17/801,389, filed Jun. 14, 2023.
Reddit comment on deleted post Jan. 8, 2020, https://www.reddit.com/r/5MeODMT/comments/elvrpt/comment/fdkizfn/.
Hazekamp 2006 Evaluation of a Vaporizing Device Volcano for the Pulmonary Administration of Tetrahydrocannabinol, Journal of Pharmaceutical Sciences, vol. 19 6 1308-1317.
Third Party Submission filed in U.S. Appl. No. 17/801,389, filed Sep. 25, 2023.
E.S. Vermeulen et al., "Novel 5HT7 Receptor Inverse Agonists. Synthesis and Molecular Modelling of Arylpiperazine and 1,2,3,4-Tetrahydroisoquinoline Based Axylsulfonamides", Journal of Medicinal Chemistry, vol. 47, No. 22, Sep. 23, 2004, pp. 5451-5466.
A.M. Sherwood et al., "Synthesis and Characterisation of 5meO-DMT Succinate for Clinical Use", ACS Omega, vol. 5, 49, Dec. 2, 2020, pp. 32067-32075.
ACS on STN entry RN 2761182-82-3, 5-MeO-DMT HBr (entered Mar. 3, 2022).
Alastair J. Florence: "Polymorph screening in pharmaceutical development—European Pharmaceutical Review", Aug. 19, 2010 (Aug. 19, 2010), XP055457333.
Christopher Greer Ewing, "Ground to Source-experiencing the Divine within", Apr. 15, 2017 https://thepracticaltripper.wordpress.com/2017/04/15/ground-tosource-experiencing-the-divine-within-2/ https://web.archive.org/web/20231122181702/https://thepracticaltripper.wordpress.com/2017/04/15/ground-to-source-experiencing-thedivine-within-2/.
Herrmann, "The Sunnybrook Stroke Study: A Prospective Study of Depressive Symptoms and Functional Outcome" Stroke. 1998;29:618-624, Mar. 1, 1998.
ISR issued in WIPO Patent Application No. PCT/EP2022/070590, dated Nov. 4, 2022.
IPRP issued in WIPO Patent Application No. PCT/EP2022/070590, dated Jan. 18, 2024.
Written Opinion issued in WIPO Patent Application No. PCT/EP2023/057873, dated Jul. 13, 2023.
Written Opinion issued in WIPO Patent Application No. PCT/EP2023/057874, dated Jun. 29, 2023.
Written Opinion issued in WIPO Patent Application No. PCT/EP2023/057883, dated Jul. 13, 2023.
Written Opinion issued in WIPO Patent Application No. PCT/EP2023/057885, dated Jul. 7, 2023.
Third Party Observation filed in EP3927337 (WO2020169850), Apr. 3, 2023.
Third Party Observation filed in EP3927337 (WO2020169850), Oct. 20, 2023.
Third Party Observation filed in EP3927337 (WO2020169850), Jan. 15, 2024.
Third Party Observation filed in EP3927338 (WO2020169851), Jan. 18, 2024.
Third Party Observation filed in EP3986864 (WO2020254584), Sep. 11, 2023.
Third Party Observation filed in EP3986864 (WO2020254584), Sep. 14, 2023.
Third Party Observation filed in EP3986864 (WO2020254584), Sep. 21, 2023.
Third Party Observation filed in PCT/EP2022/070590 (WO2023002005), Sep. 19, 2023.
Third Party Observation filed in PCT/EP2022/070590 (WO2023002005), Nov. 14, 2023.
Third Party Observation filed in PCT/EP2023/057871 (WO2023186824), Dec. 13, 2023.
Third Party Observation filed in PCT/EP2023/057877 (WO2023186830), Dec. 5, 2023.
Third Party Observation filed in PCT/EP2023/057882 (WO2023186834), Nov. 14, 2023.
Third Party Observation filed in EP4313945 (WO2023186834), Dec. 18, 2023.
Third Party Observation filed in EP Patent Application No. EP4110295 (WO2021170614), Sep. 22, 2023.
ISR issued in WIPO Patent Application No. PCT/EP2023/057882, dated May 11, 2023.
Written Opinion issued in WIPO Patent Application No. PCT/EP2023/057882, dated Oct. 5, 2023.
Third Party Submission filed in U.S. Appl. No. 17/431,626, filed Feb. 26, 2024.
Examination Report issued in EP20710060.3 (EP3927338) dated Dec. 16, 2022.
Anonymous, "What Is Depression?", American Psychiatric Association, (Jan. 17, 2019), pp. 1-6, American Psychiatric Association, URL: The Wayback Machine—https://web.archive.org/web/20190117034902/https://www.psychiatry.org/patient, (Feb. 6, 2024), XP093127661.
Jaffe Dena H., Rive Benoit, Denee Tom R., "The humanistic and economic burden of treatment-resistant depression in Europe: a cross-sectional study", BMC Psychiatry, GB , (Dec. 1, 2019), vol. 19, No. 1, doi:10.1186/s12888-019-2222-4, ISSN 1471-244X, pp. 1-11, XP093127705.
Malhi Gin S., Das Pritha, Mannie Zola, Irwin Lauren, "Treatment-resistant depression: problematic illness or a problem in our approach?", British Journal of Psychiatry, (Jan. 1, 2019), vol. 214, No. 1, doi:10.1192/bjp.2018.246, ISSN 0007-1250, pp. 1-3, XP093127711.
Harwood Laurence M., Moody C J, "Experimental Organic Chemistry: Principles and Practice", Experimental Chemistry—Organic Chemistry and Reaction, 1990, (Jan. 1, 1989), pp. 129-130, ISBN 978-0-632-02016-4, XP093089884.
Zal, "A Meditation on Solvents", Science.org, 2008, p. 1, XP093099402, retrieved Sep. 19, 2023.
Reckweg Johannes et al., "The clinical pharmacology and potential therapeutic applications of 5-methoxyN,N-dimethyltryptamine (5-MeO-DMT)" Journal of Neurochemistry, Feb. 11, 2022, vol. 162, Issue 1 / p. 128-146, https://doi.Org/10.1111/jnc.15587.
Elphick, M.; Anderson, S. M.; Hallis, K. F.; Grahame-Smith, D. G., "Effects of carbamazepine on 5-hydroxytryptamine function in rodents," Psychopharmacology (Berl), 1990;100(1):49-53.
Heal, D. J.; Hurst, E. M.; Prow, M. R.; Buckett, W. R., "An investigation of the role of 5-hydroxytryptamine in the attenuation of presynaptic alpha 2-adrenoceptor-mediated responses by antidepressant treatments," Psychopharmacology (Berl), 1990;101(1):100-6.
Kelland, M. D.; Freeman, A. S.; Chiodo, L. A., "Serotonergic afferent regulation of the basic physiology and pharmacological responsiveness of nigrostriatal dopamine neurons" J Pharmacol Exp Ther, 1990;253(2):803-11.
Licata, F.; Li Volsi, G.; Maugeri, G.; Santangelo, F., "Effects of 5-hydroxytryptamine on the firing rates of neurons of the lateral vestibular nucleus in the rat," Exp Brain Res, 1990;79(2):293-8.
Lima, L.; Drujan, B.; Walder, R., "Cerebral serotonin in viral encephalitis," J Neural Transm Suppl, 1990;29:141-51.
Loscher, W.; Witte, U.; Fredow, G.; Ganter, M.; Bickhardt, K., "Pharmacodynamic effects of serotonin (5-HT) receptor ligands in pigs: stimulation of 5-HT2 receptors induces malignant hyperthermia," Naunyn Schmiedebergs Arch Pharmacol, 1990;341(6):483-93.
Molina, V. A.; Volosin, M.; Cancela, L.; Keller, E.; Murua, V. S.; Basso, A. M., "Effect of chronic variable stress on monoamine receptors: influence of imipramine administration," Pharmacol Biochem Behav, 1990;35(2):335-40.
Spoerke, D. G.; Hall, A. H., "Plants and Mushrooms of Abuse," Emergency Medicine Clinics of North America, 1990;8(3):579-593.
Thor, K. B.; Hisamitsu, T.; de Groat, W. C., "Unmasking of a neonatal somatovesical reflex in adult cats by the serotonin autoreceptor agonist 5-methoxy-N,N-dimethyltryptamine," Brain Res Dev Brain Res, 1990;54(1):35-42.

(56) References Cited

OTHER PUBLICATIONS

Wing, L. L.; Tapson, G. S.; Geyer, M. A., "5HT-2 mediation of acute behavioral effects of hallucinogens in rats," Psychopharmacology (Berl), 1990;100(3):417-25.
Ahlenius, S.; Larsson, K., "Opposite effects of 5-methoxy-N,N-dimethyl-tryptamine and 5-hydroxytryptophan on male rat sexual behavior," Pharmacol Biochem Behav, 1991;38(1):201-5.
Akai, T.; Takahashi, M.; Nakada, Y.; Ohnishi, R.; Ikoma, Y.; Yamaguchi, M., "[Anxiolytic effects of lisuride and its agonistic action to central 5-HT1A receptors]," Nihon Yakurigaku Zasshi, 1991;97(4):209-20.
Ben-Harari, R. R.; Dalton, B. A.; Osman, R.; Maayani, S., "Kinetic characterization of 5-hydroxytryptamine receptor desensitization in isolated guinea-pig trachea and rabbit aorta," J Pharmacol Exp Ther, 1991;257(1):416-24.
Bogdanov, M. B.; Gainetdinov, R. R.; Kudrin, V. S.; Medvedev, O. S.; Val'dman, A. V., "[Study by the intracerebral microdialysis method of the effects of atypical neuroleptics and anxiolytics on striatal release and metabolism of dopamine in awake rats]," Biull Eksp Biol Med, 1991;111(5):505-7.
Boulenguez, P.; Chauveau, J.; Segu, L.; Morel, A.; Lanoir, J.; Delaage, M., "A new 5-hydroxy-indole derivative with preferential affinity for 5-HT1B binding sites," Eur J Pharmacol, 1991;194(1):91-8.
Clement, M. E.; McCall, R. B., "Pharmacological characterization of medullary serotonin neurons," Brain Res, 1991;542(2):205-11.
Fone, K. C.; Dixon, D. M., "Acute and chronic effects of intrathecal galanin on behavioural and biochemical markers of spinal motor function in adult rats," Brain Res, 1991;544(1):118-25.
Fujii, E.; Nomoto, T.; Muraki, T., "Effects of two 5-hydroxytryptamine agonists on head-weaving behaviour in streptozotocin-diabetic mice," Diabetologia, 1991;34(8):537-41.
Govitrapong, P.; Prapapanich, V.; Ebadi, M., "Identification of serotonin 5HT2 receptors in bovine pineal gland," J Pineal Res, 1991;11(3-4):182-7.
Koshikawa, N.; Mocaer, E.; Stephenson, J. D., "The effects of tianeptine on wet-dog shakes, fore-paw treading and a flexor reflex in rats are consistent with enhancement of 5-hydroxytryptamine uptake," Eur J Pharmacol, 1991;198(1):51-7.
Lima, L., "Region-selective reduction of brain serotonin turnover rate and serotonin agonist-induced behavior in mice treated with clonazepam," Pharmacol Biochem Behav, 1991;39(3):671-6.
Millan, M. J.; Bervoets, K.; Colpaert, F. C., "5-hydroxytryptamine (5-HT)1A receptors and the tail-flick response. I. 8-hydroxy-2-(di-n-propylamino) tetralin HBr-induced spontaneous tail-flicks in the rat as an in vivo model of 5-HT1A receptor-mediated activity," J Pharmacol Exp Ther, 1991;256(3):973-82.
Millan, M. J.; Colpaert, F. C., "5-hydroxytryptamine (HT)1A receptors and the tail-flick response. II. High efficacy 5-HT1A agonists attenuate morphine-induced antinociception in mice in a competitive-like manner," J Pharmacol Exp Ther, 1991;256(3):983-92.
Minetti, S. A.; Fulginiti, S., "Sexual receptivity of adult female rats prenatally intoxicated with alcohol on gestational day 8," Neurotoxicol Teratol, 1991;13(5):531-4.
Sanders-Bush, E.; Breeding, M., "Choroid plexus epithelial cells in primary culture: a model of 5HTIC receptor activation by hallucinogenic drugs," Psychopharmacology (Berl), 1991;105(3):340-6.
Volterra, G.; Cutrufo, C.; Lecci, A., "m-trifluoromethylphenylpiperazine and m-chlorophenylpiperazine-induced hypothermia in mice is reversed by tricyclic antidepressants and other drugs," Eur Neuropsychopharmacol, 1991;1(4):519-28.
Wright, I. K.; Ismail, H.; Upton, N.; Marsden, C. A., "Effect of isolation rearing on 5-HT agonist-induced responses in the rat," Psychopharmacology (Berl), 1991;105(2):259-63.
Yamaguchi, M.; Kimura-Iwasaki, K.; Akai, T.; Nakada, Y.; Nakagawa, H., "Terguride, a dopamine D(2) partial agonist, as a discriminative stimulus in rats," Behav Pharmacol, 1991;2(3):233-240.
Chojnacka-Wojcik, E., "Modulation of the 5-HT1C receptor-mediated behavior by 5-HT2, but not 5-HT1A, receptor activation," Pol J Pharmacol Pharm, 1992;44(5):427-36.
Chojnacka-Wojcik, E., "Functional interaction between 5-HT1B and 5-HT1A or 5-HT2 receptors in mice," Pol J Pharmacol Pharm, 1992;44(3):251-60.
Darmani, N. A.; Martin, B. R.; Glennon, R. A., "Repeated administration of low doses of cocaine enhances the sensitivity of 5- HT2 receptor function," Pharmacol Biochem Behav, 1992;41(3):519-27.
Eglen, R. M.; Perkins, L. A.; Walsh, L. K.; Whiting, R. L. "Agonist action of indole derivatives at 5-HT1-like, 5-HT3, and 5HT4 receptors in vitro," J Auton Pharmacol, 1992;12(5):321-33.
Eison, A. S.; Wright, R. N., "5-HT1A and 5-HT2 receptors mediate discrete behaviors in the Mongolian gerbil," Pharmacol Biochem Behav, 1992;43(1):131-7.
Fulginiti, S.; Vigliecca, N. S.; Minetti, S. A., "Acute ethanol intoxication during pregnancy: postnatal effects on the behavioral response to serotonin agents," Alcohol, 1992;9(6):523-7.
Glennon, R. A.; Young, R.; Dukat, M., "5-HT3 agonist 2-methylserotonin as a training drug in discrimination studies," Pharmacol Biochem Behav, 1992;41(2):361-4.
Kärkkäinen, J.; Räisänen, M., "Nialamide, an MAO inhibitor, increases urinary excretion of endogenously produced bufotenin in man," Biological Psychiatry, 1992;32(11):1042-1048.
Kolbeck, S. C.; Steers, W. D., "Neural regulation of the vas deferens in the rat: an electrophysiological analysis," Am J Physiol, 1992;263(2 Pt 2):R331-8.
Lima, L.; Radtke, I.; Drujan, B., "[3H]serotonin binding sites in goldfish retinal membranes," Neurochem Res, 1992;17(10):991-6.
Maps, "Subjective effects of DMT and the development of the Hallucinogen Rating Scale by Dr. Rick Strassman," 1992.
Nakamura, S.; Tani, Y.; Maezono, Y.; Ishihara, T.; Ohno, T., "Learning deficits after unilateral AF64A lesions in the rat basal forebrain: role of cholinergic and noncholinergic systems," Pharmacol Biochem Behav, 1992;42(1):119-30.
Ohue, T.; Koshimura, K.; Akiyama, Y.; Ito, A.; Kido, T.; Takagi, Y.; Miwa, S., "Regulation of acetylcholine release in vivo from rat hippocampus by monoamines as revealed by novel column-switching HPLC with electrochemical detection," Brain Res, 1992;572(1-2):340-4.
Tomaszewski, Z.; Johnson, M. P.; Huang, X.; Nichols, D. E., "Benzofuran bioisosteres of hallucinogenic tryptamines," J Med Chem, 1992;35(11):2061-4.
Yamazaki, J.; Fukuda, H.; Nagao, T.; Ono, H., "5-HT2/5-HT1C receptor-mediated facilitatory action on unit activity of ventral horn cells in rat spinal cord slices," Eur J Pharmacol, 1992;220(2-3):237-42.
Yamazaki, J.; Ono, H.; Nagao, T., "Stimulatory and inhibitory effects of serotonergic hallucinogens on spinal mono- and polysynaptic reflex pathways in the rat," Neuropharmacology, 1992;31(7):635-42.
Young, A. H.; MacDonald, L. M.; St John, H.; Dick, H.; Goodwin, G. M., "The effects of corticosterone on 5-HT receptor function in rodents," Neuropharmacology, 1992;31(5):433-8.
Abdulqader A. Alhaider, M. H., George L. Wilcox, "Intrathecal 5-methoxy-N,N-dimethyltryptamine in mice modulates 5-HT 1 and 5-HT 3 receptors," European Journal of Pharmacology, 1993.
Bondarenko, N. A.; Bondarenko, N. A.; Voronina, T. A., "[Differences in the action of serotonin 1A-receptor agonists on rotating behavior or rats with unilaterally raphe-lesioned rats]," Biull Eksp Biol Med, 1993;115(2):157-9.
Hery, F.; Hamon, M., "Neuroleptics and serotonin," Encephale, 1993;19(5):525-32.
Licata, F.; Li Volsi, G.; Maugeri, G.; Ciranna, L.; Santangelo, F., "Serotonin-evoked modifications of the neuronal firing rate in the superior vestibular nucleus: a microiontophoretic study in the rat," Neuroscience, 1993;52(4):941-9.
Licata, F.; Li Volsi, G.; Maugeri, G.; Santangelo, F., "Excitatory and inhibitory effects of 5-hydroxytryptamine on the firing rate of medial vestibular nucleus neurons in the rat," Neurosci Lett, 1993;154(1-2):195-8.
Lima, L.; Salazar, M.; Trejo, E., "Modulation of 5HT1A receptors in the hippocampus and the raphe area of rats treated with clonazepam," Prog Neuropsychopharmacol Biol Psychiatry, 1993; 17(4):663-77.

(56) References Cited

OTHER PUBLICATIONS

Liminga, U.; Johnson, A. E.; Andren, P. E.; Gunne, L. M., "Modulation of oral movements by intranigral 5-hydroxytryptamine receptor agonists in the rat," Pharmacol Biochem Behav, 1993;46(2):427-33.
Parker, E. M.; Grisel, D. A.; Iben, L. G.; Shapiro, R. A., "A single amino acid difference accounts for the pharmacological distinctions between the rat and human 5-hydroxytryptamine 1B receptors," J Neurochem, 1993;60(1):380-3.
Reimann, W.; Schneider, F., "The serotonin receptor agonist 5-methoxy-N,N-dimethyltryptamine facilitates noradrenaline release from rat spinal cord slices and inhibits monoamine oxidase activity," Gen Pharmacol, 1993;24(2):449-53.
Schreiber, R.; de Vry, J., "Studies on the neuronal circuits involved in the discriminative stimulus effects of 5-hydroxytryptamine1A receptor agonists in the rat," J Pharmacol Exp Ther, 1993;265(2):572-9.
R. G. Dos Santos et al., Efficacy, tolerability, and safety of serotonergic psychedelics for the management of mood, anxiety, and substance-use disorders: a systematic review of systematic reviews, Expert Rev Clin Pharmacol, 2018, vol. 11(9): 889-902, doi: 10.1080/17512433.2018.1511424.
J. Peters et al., Engineering Safer Psychedelics for Treating Addiction, Neurosci Insights, 2021, vol. 16, doi: 10.1177/26331055211033847.
Erowid, Erowid 5-MeO-DMT Health impact, 2018.
Erowid, Erowid description of fatal 5-MeO-DMT case, 2018.
T. Haeusermann et al., Ethical considerations in rapid and novel treatments in psychiatry, Neuropsychopharmacology, 2023.
D. B. Yaden et al., Ethical Issues Regarding Nonsubjective Psychedelics as Standard of Care, Camb Q Healthe Ethics, 2022vol. 31(4): 464-471, doi: 10.1017/S096318012200007X.
D. J. Heal et al., Evaluating the abuse potential of psychedelic drugs as part of the safety pharmacology assessment for medical use in humans, Neuropharmacology, 2018, vol. 142: 89-115, doi: 10.1016/j.neuropharm.2018.01.049.
D. E. Gard et al., Evaluating the Risk of Psilocybin for the Treatment of Bipolar Depression: A Review of the Research Literature and Published Case Studies, 2021, doi: 10.1101/2021.04.02.21254838.
A. Y. Simao et al., Evaluation of the Cytotoxicity of Ayahuasca Beverages, Molecules, 2020, vol. 25(23), doi: 10.3390/molecules25235594.
D. D. Kocak et al., Examining psychedelic drug action, Nat Chem, 2024, vol. 16(1): 142, doi: 10.1038/s41557-023-01412-w.
B. Szigeti et al., Expectancy effects in psychedelic trials, Biol Psychiatry Cogn Neurosci Neuroimaging, 2024, doi: 10.1016/j.bpsc.2024.02.004.
M. Butler et al., "Expectancy in placebo-controlled trials of psychedelics: if so, so what?" Psychopharmacology (Berl), 2022, doi: 10.1007/s00213-022-06221-6.
E. A. D. Schindler, et al., Exploratory Controlled Study of the Migraine-Suppressing Effects of Psilocybin, Neurotherapeutics, 2021, vol. 18(1): 534-543, doi: 10.1007/s13311-020-00962-y.
D. C. D'Souza et al., Exploratory study of the dose-related safety, tolerability, and efficacy of dimethyltryptamine (DMT) in healthy volunteers and major depressive disorder, Neuropsychopharmacology, 2022, doi: 10.1038/s41386-022-01344-y.
G. O. Silveira et al., Fast Hollow Fiber Liquid-Phase Microextraction as a Greener Alternative for the Determination of N,N-Dimethyltryptamine and Harmala Alkaloids in Human Urine, Front Chem, 2020, vol. 8, doi: 10.3389/fchem.2020.558501.
T. Gicquel et al., Fatal intoxication related to two new arylcyclohexylamine derivatives (2F-DCK and 3-MeO-PCE), Forensic Sci Int, 2021, vol. 324, doi: 10.1016/j.forsciint.2021.110852.
F. McCarthy-Doig, Feminism and Psychedelic Therapy: How scientific values can help or hinder potentially fruitful avenues of research, 2020.
U. Kozlowska et al., From psychiatry to neurology: Psychedelics as prospective therapeutics for neurodegenerative disorders, J Neurochem, 2022, vol. 162(1): 89-108, doi: 10.1111/jnc.15509.
P. Vizeli et al., Genetic influence of CYP2D6 on pharmacokinetics and acute subjective effects of LSD in a pooled analysis, Sci Rep, 2021, vol. 11(1): 10851, doi: 10.1038/s41598-021-90343-y.
J. S. Aday et al., Great Expectations: recommendations for improving the methodological rigor of psychedelic clinical trials, Psychopharmacology (Berl), 2022, vol. 239(6): 1989-2010, doi: 10.1007/s00213-022-06123-7.
G. Martinotti et al., Hallucinogen Persisting Perception Disorder: Etiology, Clinical Features, and Therapeutic Perspectives, Brain Sci, 2018, vol. 8(3), doi: 10.3390/brainsci8030047.
R. G. Dos Santos et al., Hallucinogenic/psychedelic 5HT2A receptor agonists as rapid antidepressant therapeutics: Evidence and mechanisms of action, J Psychopharmacol, 2021, vol. 35(4): 453-458, doi: 10.1177/0269881120986422.
C. S. Grob, Handbook of Medical Hallucinogens, 2021.
C. Pronovost-Morgan et al., Harnessing placebo: Lessons from psychedelic science, J Psychopharmacol, 2023, doi: 10.1177/02698811231182602.
E. Susser et al., Healthy pregnancy and prevention of psychosis, World Psychiatry, 2018, vol. 17(3): 357-358, doi: 10.1002/wps.20554.
C. R. Nicholas et al., High dose psilocybin is associated with positive subjective effects in healthy volunteers, J Psychopharmacol, 2018, vol. 32(7): 770-778, doi: 10.1177/0269881118780713.
M. van Elk et al., History repeating: guidelines to address common problems in psychedelic science, Ther Adv Psychopharmacol, 2023, vol. 13, doi: 10.1177/20451253231198466.
R. L. Carhart-Harris, "How do psychedelics work?" Curr Opin Psychiatry, 2019, vol. 32(1): 16-21, doi: 10.1097/YCO.0000000000000467.
H. Artin et al., How do serotonergic psychedelics treat depression: The potential role of neuroplasticity, World J Psychiatry, 2021, vol. 11(6): 201-214, doi: 10.5498/wjp.v11.i6.201.
A. Inserra, Hypothesis: The Psychedelic Ayahuasca Heals Traumatic Memories via a Sigma 1 Receptor-Mediated Epigenetic-Mnemonic Process,Front Pharmacol, 2018, vol. 9: 330, doi: 10.3389/fphar.2018.00330.
D. R. George et al., Imagining a Role for Psychedelics in Dementia Care, Am J Geriatr Psychiatry, 2019, vol. 27(9): 1028-1030 doi: 10.1016/j.jagp.2019.03.008.
E. Tagliazucchi et al., Increased Global Functional Connectivity Correlates with LSD-Induced Ego Dissolution, Curr Biol, 2016 vol. 26(8): 1043-50, doi: 10.1016/j.cub.2016.02.010.
T. Vesikari, "Increased Take Rate of Oral Rotavirus Vaccine in Infants after Milk Feeding," The Lancet, 1984, vol. 324(8404), doi: 10.1016/s0140-6736(84)91262-5.
J. G. Dean, Indolethylamine-N-methyltransferase Polymorphisms: Genetic and Biochemical Approaches for Study of Endogenous N,N,-dimethyltryptamine, Front Neurosci, 2018, vol. 12: 232, doi: 10.3389/fnins.2018.00232.
N. D. Sepeda et al., Inhaled 5-methoxy-N,N-dimethyltryptamine: Supportive context associated with positive acute and enduring effects, Journal of Psychedelic Studies, 2019, p. 1-9, doi: 10.1556/2054.2019.033.
T. Conclave, Integration & Suggested Techniques for Grounding, 2018.
J. Barbut Siva et al., Interactions between classic psychedelics and serotonergic antidepressants: Effects on the acute psychedelic subjective experience, well-being and depressive symptoms from a prospective survey study, J Psychopharmacol, 2024, doi: 10.1177/02698811231224217.
N. M. Barnes et al., International Union of Basic and Clinical Pharmacology. CX. Classification of receptors for 5-hydroxytryptamine; pharmacology and function, Pharmacological reviews, 2021, vol. 73(1): 310-520.
L. A. Averill et al., Investigational drugs for assisting psychotherapy for posttraumatic stress disorder (PTSD): emerging approaches and shifting paradigms in the era of psychedelic medicine, Expert Opin Investig Drugs, 2022, vol. 31(2): 133-137, doi: 10.1080/13543784.2022.2035358.
M. V. Uthaug, In-Vivo Effects of Toad Venom (5-MeO-DMT) on Affect and Thinking Style, Beyond Psychedelics, 2018.

(56) References Cited

OTHER PUBLICATIONS

B. Kadriu et al., Ketamine and Serotonergic Psychedelics: Common Mechanisms Underlying the Effects of Rapid-Acting Antidepressants, Int J Neuropsychopharmacol, 2021, vol. 24(1): 8-21, doi: 10.1093/ijnp/pyaa087.
D. E. McCulloch et al., Lasting effects of a single psilocybin dose on resting-state functional connectivity in healthy individuals, J Psychopharmacol, 2022, vol. 36(1): 74-84, doi: 10.1177/02698811211026454.
M. Wolff et al., Learning to Let Go: A Cognitive-Behavioral Model of How Psychedelic Therapy Promotes Acceptance, Front Psychiatry, 2020, vol. 11: 5, doi: 10.3389/fpsyt.2020.00005.
Opis, Legalising Access to Psilocybin to End the Agony of Cluster Headaches, 2020.
G. A. Higgins et al., Low Doses of Psilocybin and Ketamine Enhance Motivation and Attention in Poor Performing Rats: Evidence for an Antidepressant Property, Front Pharmacol, 2021, vol. 12, doi: 10.3389/fphar.2021.640241.
G. Wieckiewicz et al., Lysergic Acid Diethylamide, Psilocybin and Dimethyltryptamine in Depression Treatment: A Systematic Review, Pharmaceuticals (Basel), 2021, vol. 14(8), doi: 10.3390/ph14080793.
B. D. M. Jones et al., Magnitude of the Placebo Response Across Treatment Modalities Used for Treatment-Resistant Depression in Adults: A Systematic Review and Meta-analysis, JAMA Netw Open, 2021, vol. 4(9), e2125531 doi: 10.1001/jamanetworkopen.2021.25531.
P. J. Fitzgerald, Many Drugs of Abuse May Be Acutely Transformed to Dopamine, Norepinephrine and Epinephrine In Vivo, Int J Mol Sci, 2021, vol. 22(19), doi: 10.3390/ijms221910706.
Maps, Maps Newsletter Jan. 2018, 2018.
G. M. Jones et al., MDMA/ecstasy use and psilocybin use are associated with lowered odds of psychological distress and suicidal thoughts in a sample of US adults, J Psychopharmacol, 2022, vol. 36(1): 46-56, doi: 10.1177/02698811211058923.
F. Muller et al., MDMA-induced changes in within-network connectivity contradict the specificity of these alterations for the effects of serotonergic hallucinogens, Neuropsychopharmacology, 2021, vol. 46(3), 545-553, doi: 10.1038/s41386-020-00906-2.
A. M. Jaster et al., Mechanisms and molecular targets surrounding the potential therapeutic effects of psychedelics, Mol Psychiatry, 2023, doi: 10.1038/s41380-023-02274-x.
E. Sanders-Bush et al., Metabolism of bufotenine-2'-14C in human volunteers, Life Sciences, 1976, vol. 19(9), doi: 1407-1412.
R. J. Zeifman et al., Methodological concerns in psychedelic research: The issues of nonequivalent psychological support and generalizability, Eur Neuropsychopharmacol, 2024, vol. 78: 13-15, doi: 10.1016/j.euroneuro.2023.09.007.
R. S. McIntyre et al., Treatment-resistant depression: definition, prevalence, detection, management, and investigational interventions, World Psychiatry, 2023, vol. 22(3): 394-412, doi: 10.1002/wps.21120.
J. J. Palamar et al., Trends in DMT and other tryptamine use among young adults in the United States, Am J Addict, 2018, vol. 27(7): 578-585, doi: 10.1111/ajad.12803.
D. W. Lawrence et al., Trends in the Top-Cited Articles on Classic Psychedelics, J Psychoactive Drugs, 2021, p. 1-16, doi: 10.1080/02791072.2021.1874573.
R. Carhart-Harris et al., Trial of Psilocybin versus Escitalopram for Depression, N Engl J Med, 2021, vol. 384(15): 1402-1411, doi: 10.1056/NEJMoa2032994.
J. A. Olson et al., Tripping on nothing: placebo psychedelics and contextual factors, Psychopharmacology (Berl), 2020, vol. 237(5): 1371-1382, doi: 10.1007/s00213-020-05464-5.
G. Ballentine et al., Trips and neurotransmitters: Discovering principled patterns across 6850 hallucinogenic experiences, Sci Adv, 2022, vol. 8(11), doi: 10.1126/sciadv.abl6989.
P. McAllister, Tuning in to Psychedelics for Suicide Headaches, Practical Neurology, 2018.
R. L. Lancelotta et al., Use of Benefit Enhancement Strategies among 5-Methoxy-N,N-Dimethyltryptamine (5-MeO-DMT) Users: Associations with Mystical, Challenging, and Enduring Effects, J Psychoactive Drugs, 2020, vol. 52(3): 273-281, doi: 10.1080/02791072.2020.1737763.
J. J. Palamar et al., Use of new and uncommon synthetic psychoactive drugs among a nationally representative sample in the United States, 2005-2017, Human Psychopharmacology: Clinical and Experimental, 2019, vol. 34(2), e2690.
F. S. Barrett et al., Validation of the revised Mystical Experience Questionnaire in experimental sessions with psilocybin, J Psychopharmacol, 2015, vol. 29(11): 1182-90, doi: 10.1177/0269881115609019.
E. Jacobs et al., When the Trial Ends: The Case for Post-Trial Provisions in Clinical Psychedelic Research, Neuroethics, 2024, vol. 17(1): 3, doi: 10.1007/s12152-023-09536-z.
G. Deco et al., Whole-Brain Multimodal Neuroimaging Model Using Serotonin Receptor Maps Explains Non-linear Functional Effects of LSD, Curr Biol, 2018, vol. 28(19): 3065-3074 e6, doi: 10.1016/j.cub.2018.07.083.
C. Hayes et al, "Will psilocybin lose its magic in the clinical setting?" Ther Adv Psychopharmacol, 2022, vol. 12, doi: 10.1177/20451253221090822.
J. J. Breeksema et al., Working with Weirdness: A Response to Moving Past Mysticism in Psychedelic Science, ACS Pharmacol Transl Sci, 2021, vol. 4(4): 1471-1474, doi: 10.1021/acsptsci.1c00149.
T. Schmidt, "Workshop: The empirical study of altered states of consciousness common standards in the psychometric assessment of subjective experiences," 2018, doi: 10.13140/RG.2.2.11469.54240.
Porter R.S. et al: "Mood disorders", The Merck Manual of Diagnosis and Therapy—Twentieth Edition, Jan. 1, 2018 (Jan. 1, 2018), pp. 1757-1766, XP093113475.
Vollenweider et al.—Psychedelic drugs: neurobiology and potential for treatment of psychiatric, Nat Rev Neurosci, Sep. 14, 2020, 21(11): 611-624, doi: 10.1038/s41583-020-0367-2.
Unger, "Mescaline, LSD, Psilocybin, and Personality Change," Psychiatry, 26, 1963, pp. 111-125.
Pahnke et al., "LSD-assisted psychotherapy with terminal cancer patients. In: Psychedelic drugs," Proceedings of a Hahnemann Medical College and Hospital Symposium. Editors: Richard E. Hicks, Paul Jay Fink, Van Buren O. Hammett. Grune & Stratton, New York/London 1969, pp. 33-42.
MacLean Jr et al., "The use of LSD-25 in the treatment of alcoholism and other psychiatric problems," Q J Stud Alcohol, 22, 1961, pp. 34-45.
Johnson et al., "Pilot study of the 5-HT2AR agonist psilocybin in the treatment of tobacco addiction," J Psychopharmacol, 28(11), 2014, pp. 983-992.
Johnson MW et al., "Long-term follow-up of psilocybin-facilitated smoking cessation," Am J Drug Alcohol Abuse, 43(1), 2017, pp. 55-60.
Jensen, "A treatment program for alcoholics in a mental hospital," Q J Stud Alcohol, 23, 1962, pp. 315-320.
Uthaug, The Exploration of Naturalistically used Ayahuasca and 5-MeO-DMT, 2020, doi: 10.26481/dis.20200624 mu.
Allen et al., LSD increases sleep duration the night after microdosing, Transl Psychiatry, 2024, 14(1): 191, doi: 10.1038/s41398-024-02900-4.
Becker et al., Acute effects of psilocybin after escitalopram or placebo pretreatment in a randomized, double-blind, placebo-controlled, crossover study in healthy subjects, Clinical Pharmacology & Therapeutics, 2022, 111(4): 886-895.
Berlin et al., Monoamine oxidases and tobacco smoking, International Journal of Neuropsychopharmacology, 2001, 4(1):33-42.
Biospace, Small Pharma Reports Positive Top-line Data from SPL026 (DMT)-SSRI Drug Interaction Study in Patients with Major Depressive Disorder, Apr. 30, 2023.
Cheng et al., N, N-Dimethyltryptamine, a natural hallucinogen, ameliorates Alzheimer's disease by restoring neuronal Sigma-1

(56) References Cited

OTHER PUBLICATIONS receptor-mediated endoplasmic reticulum-mitochondria crosstalk, Alzheimers Res Ther, 2024, 16(1): 95, doi: 10.1186/s13195-024-01462-3.
Geyer et al., Behavioural and pharmacological studies of pharmahuasca in rodents, European Neuropsychopharmacology, 2016, 26, doi: 10.1016/s0924-977x(16)30889-6.
Goodwin et al., "5-HT2 receptor characteristics in frontal cortex and 5-HT2 receptor-mediated head-twitch behaviour following antidepressant treatment to mice", British journal of pharmacology, 1984, 83(1): 235.
Haniff et al., Psilocybin for dementia prevention? The potential role of psilocybin to alter mechanisms associated with major depression and neurodegenerative diseases, Pharmacol Ther, 2024, pp. 108641, doi:10.1016/j.pharmthera.2024.108641.
Rucker et al., Phase 1, placebo-controlled, single ascending dose trial to evaluate the safety, pharmacokinetics and effect on altered states of consciousness of intranasal BPL-003 (5-methoxy-N,N-dimethyltryptamine benzoate) in healthy participants, J Psychopharmacol, 2024, 2698811241246857, doi: 10.1177/02698811241246857.
Sheth et al., The Effects of Ayahuasca on Psychological Disorders: A Systematic Literature Review, Cureus, 2024, 16(3): e55574, doi: 10.7759/cureus.55574.
Tap, The potential of 5-methoxy-N,N-dimethyltryptamine in the treatment of alcohol use disorder: A first look at therapeutic mechanisms of action, Addict Biol, 2024, 29(4): e13386, doi: 10.1111/adb.13386.
Warren et al., Structural pharmacology and therapeutic potential of 5-methoxytryptamines, Nature, 2024, 630, 8015, 237-246, doi: 10.1038/s41586-024-07403-2.
Examination Report issued in EP3927338, Jan. 3, 2024.
Examination Report issued in EP3927338, Dec. 16, 2022.
Examination Report issued in EP3986864, May 9, 2023.
Result of Consultation by Telephone issued in EP Patent Application No. EP3927338, dated Mar. 27, 2024.
Third-Party Observation and Additional Comments filed in PCT/EP2020/54804, Jun. 28, 2021.
Office Action issued in JP 2021-575424 (WO2020/254584), dated Jan. 7, 2025, translation.
European Search Report on EP4464377 (WO2020169851) dated Jan. 24, 2025.
European Search Opinion on EP4464377 (WO2020169851) dated Jan. 24, 2025.
European Search Strategy on EP4464377 (WO2020169851) dated Jan. 24, 2025.
Examination Report issued in EP4110295 (WO2021170614), Feb. 19, 2025.
Uthaug et al., A placebo-controlled study of the effects of ayahuasca, set and setting on mental health of participants in ayahuasca group retreats, Psychopharmacology (Berl), 2021, 238(7): 1899-1910, doi: 10.1007/s00213-021-05817-8.
McAlpine et al., Development and psychometric validation of a novel scale for measuring 'psychedelic preparedness', Sci Rep, 2024, 14(1): 3280, doi: 10.1038/s41598-024-53829-z.
Hartogsohn, Set and setting, psychedelics and the placebo response: An extra-pharmacological perspective on psychopharmacology, J Psychopharmacol, 2016, 30(12): 1259-1267, doi: 10.1177/0269881116677852.
Vapormed: "Volcano Medic," Aug. 3, 2017, pp. 1-64, XP093250157, retrieved from the Internet: URL: www.vapormed.com/de/amfile/file/download/file/471/.
Third Party Submission filed in U.S. Appl. No. 18/373,903, dated Oct. 1, 2024.
ISR issued in International Patent Application No. PCT/EP2023/057873, dated Jul. 13, 2023.
ISR issued in International Patent Application No. PCT/EP2023/057883, dated Jul. 13, 2023.
ISR issued in International Patent Application No. PCT/EP2023/057874, dated Jun. 29, 2023.
ISR issued in International Pat. Appl. No. PCT/EP2023/057885, Jul. 7, 2023, translation.
Iel Yseieva "Microdosing Moms: Psilocybin & Postpartum Depression relief—Truffle Report", Oct. 29, 2021, pp. 1-10.
Clayton, "Field Trip Health Ltd. to Pursue Treatment Resistant Depression & Postpartum Depression as Indications for FT-104", Psychedelicalpha, URL://psychedelicalpha.com/news/field-trip-health-ltd-to-pursue-treatment-resistant-depression-and-postpartum-depression-as-indications-for-ft-104, Sep. 9, 2021.
Montgomery, S. A., & Åsberg, M. (1979). A new depression scale designed to be sensitive to change. The British Journal of Psychiatry 134, p. 382.
Lake et al., "Mania associated with LSD ingestion", American Journal of Psychiatry. 138(11):1508-150 (1981).
Hendin et al., 2021. "An episode of mania following self-reported ingestion of psilocybin mushrooms in a woman previously not diagnosed with bipolar disorder: A case report." Bipolar Disorders 23(4):1-3.
Szmulewicz et al., Switch to mania after ayahuasca consumption in a man with bipolar disorder: a case report. International Journal of Bipolar Disorders, (2015) 3:4.
Brown et al., A Physician's attempt to self-medicate bipolar depression with N, N-dimethyltryptamine (DMT), Journal of Psychoactive Drugs, 49(4), 294-296 (2017).
Bader et al., "Antidepressant-induced hypomania in treatment-resistant depression," Journal of Psychiatric Practice, 13.4 (2007): 233-237.
Bennett et al., "Risk from drugs in breast milk: an analysis by relative dose." Br J Clin Pharmacol 42.5 (1996): pp. 673-674.
J. Arendt, "Melatonin and the Mammalian Pineal Gland, Chapter 3: Biochemistry of the Pineal", Chapman & Hall, 1995.
Slominski et al., "Synthesis and Metabolism of Melatonin in the Skin and Retinal Pigment Epithelium. Chapter 3" Melatonin in the Promotion of Health, Watson RR (Ed.) CRC Press 2012.
Sitaram et al., "Urinary excretion of 5-methoxy-N,N-dimethyltryptamine, N,N-dimethyltryptamine and their N-oxides in the rat," Biochemical Pharmacology 36: 2235-2231 (1987).
Roseman et al., "Quality of Acute Psychedelic Experience Predicts Therapeutic Efficacy of Psilocybin for Treatment-Resistant Depressio," Front Pharmacol. 2018; 8:974.
Uthaug Malin V. et al., "A comparison of reactivation experiences following vaporization and intramuscular injection (IM) of synthetic 5-methoxy-N, N-dimethyltryptamine (6-MeO-DMT) in a naturalistic setting", Journal of Psychedelic studies, vol. 4, No. 2, Mar. 26, 2020, pp. 104-113.
Busner et al., "The Clinical Global Impressions Scale: Applying a Research Tool in Clinical Practice" Psychiatry 2007, pp. 29-37.
Spoormaker et al., "Initial validation of the SLEEP-50 questionnaire", Behav Sleep Med. 2005;3(4), 2005, pp. 227-246.
Buysse et al., "The Pittsburgh Sleep Quality Index: a new instrument for psychiatric practice and research", Psychiatry Res., 28(2), May 1989, pp. 193-213.
Shahid et al., "Stop, That and One Hundred Other Sleep Scales," Springer Science+Business Media, LLC, 2012.
Arnulf et al., "A scale for assessing the severity of arousal disorders", Sleep. 1;37(1), Jan. 1, 2014, pp. 127-136.
Beique, J. C.; Imad, M.; Mladenovic, L.; Gingrich, J. A.; Andrade, R., "Mechanism of the 5-hydroxytryptamine 2A receptor-mediated facilitation of synaptic activity in prefrontal cortex," Proc Natl Acad Sci U S A, 2007;104(23):9870-5.
Notice of Allowance issued in U.S. Appl. No. 18/604,747 dated Jul. 26, 2024 (pages reflecting non-considered IDS omitted for brevity).
Office Action issued in CN 202080045130.0 (WO2020/254584), Jul. 29, 2024, translation.
ISR issued in WIPO Patent Application No. PCT/EP2023/076820 (WO2024160392), Dec. 13, 2023.
Information on Search Strategy issued in WIPO Patent Application No. PCT/EP2023/076820 (WO2024160392), Dec. 13, 2023.
Written Opinion issued in WIPO Pat. Appl. No. PCT/EP2023/076820 (WO2024160392), Dec. 13, 2023.
ISR issued in WIPO Patent Application No. PCT/EP2023/076819 (WO2024160391), Dec. 11, 2023.

(56) References Cited

OTHER PUBLICATIONS

Information on Search Strategy issued in WIPO Patent Application No. PCT/EP2023/076819 (WO2024160391), Dec. 11, 2023.
Written Opinion issued in WIPO Pat. App. No. PCT/EP2023/076819 (WO2024160391), Dec. 11, 2023.
ISR issued in WIPO Patent Application No. PCT/EP2023/076817 (WO2024160390), Dec. 11, 2023.
Information on Search Strategy issued in WIPO Patent Application No. PCT/EP2023/076817 (WO2024160390), Dec. 11, 2023.
Written Opinion issued in WIPO Pat. App. No. PCT/EP2023/076817 (WO2024160390), Dec. 11, 2023.
ISR issued in WIPO Patent Application No. PCT/EP2023/076816 (WO2024160389), Dec. 12, 2023.
Information on Search Strategy issued in WIPO Patent Application No. PCT/EP2023/076816 (WO2024160389), Dec. 12, 2023.
Written Opinion issued in WIPO Pat. App. No. PCT/EP2023/076816 (WO2024160389), Dec. 12, 2023.
Office Action issued in CN 202080030317.3 (WO2020/169850), dated Aug. 15, 2024.
Office Action issued in IN 202117042723 (WO2020/169851), dated Aug. 20, 2024, translation.
Anonymous, "Phase 2 Clinical Trial of 1-87 GH001 in Postpartum Depression—NCT05804708," ClinicalTrials.gov, May 2, 2023 (May 2, 2023), pp. 1-10, XP093106917, www.clinicaltrials.gov/study/NCT05804708?tab=history&a=3.
Written Opinion issued in WIPO Patent Application No. PCT/EP2023/057870, Jul. 14, 2023.
Written Opinion issued in WIPO Patent Application No. PCT/EP2023/057871, Jun. 27, 2023.
Written Opinion issued in WIPO Patent Application No. PCT/EP2023/057842, Jul. 12, 2023.
Written Opinion issued in WIPO Patent Application No. PCT/EP2023/057845, Jul. 12, 2023.
Written Opinion issued in WIPO Patent Application No. PCT/EP2023/057867, Sep. 19, 2023.
Written Opinion issued in WIPO Patent Application No. PCT/EP2023/057868, Sep. 19, 2023.
Written Opinion issued in WIPO Patent Application No. PCT/EP2023/057857, Jul. 12, 2023.
Written Opinion issued in WIPO Patent Application No. PCT/EP2023/057875, Jul. 5, 2023.
Written Opinion issued in WIPO Patent Application No. PCT/EP2023/057873, Jul. 13, 2023.
Written Opinion issued in WIPO Patent Application No. PCT/EP2023/057874, Jun. 29, 2023.
Written Opinion issued in WIPO Patent Application No. PCT/EP2023/057827, Jul. 13, 2023.
Written Opinion issued in WIPO Patent Application No. PCT/EP2023/057828, Jul. 13, 2023.
Written Opinion issued in WIPO Patent Application No. PCT/EP2023/057876, Jul. 7, 2023.
Written Opinion issued in WIPO Patent Application No. PCT/EP2023/057879, Jul. 17, 2023.
Written Opinion issued in WIPO Patent Application No. PCT/EP2023/057877, Jun. 29, 2023.
Written Opinion issued in WIPO Patent Application No. PCT/EP2023/057878, Jul. 7, 2023.
Written Opinion issued in WIPO Patent Application No. PCT/EP2023/057883, Jul. 13, 2023.
Written Opinion issued in WIPO Patent Application No. PCT/EP2023/057885, Jul. 7, 2023.
Written Opinion issued in WIPO Patent Application No. PCT/EP2023/057882, dated May 11, 2023.
Tanaka, E.; Baba, N.; Toshida, K.; Suzuki, K., "Evidence for 5-HT2 receptor involvement in the stimulation of preovulatory LH and prolactin release and ovulation in normal cycling rats," Life Sci, 1993;52(7):669-76.
Chamakura, R. P., "Bufotenine—A Hallucinogen in Ancient Snuff Powders of South America and a Drug of Abuse on the Streets of New York City," Forensic Sci Rev, 1994.
Fornal, C. A.; Litto, W. J.; Metzler, C. W.; Marrosu, F.; Tada, K.; Jacobs, B. L., "Single-unit responses of serotonergic dorsal raphe neurons to 5-HT1A agonist and antagonist drug administration in behaving cats," J Pharmacol Exp Ther, 1994;270(3):1345-58.
Gudelsky, G. A.; Yamamoto, B. K.; Nash, J. F., "Potentiation of 3,4-methylenedioxymethamphetamine-induced dopamine release and serotonin neurotoxicity by 5-HT2 receptor agonists," Eur J Pharmacol, 1994;264(3):325-30.
Johnson, M. P.; Loncharich, R. J.; Baez, M.; Nelson, D. L., "Species variations in transmembrane region V of the 5-hydroxytryptamine type 2A receptor alter the structure-activity relationship of certain ergolines and tryptamines," Molecular pharmacology, 1994;45(2):277-286.
Keller, E. A.; Cancela, L. M.; Molina, V. A.; Orsingher, O. A., "Lack of adaptive changes in 5-HT sites in perinatally undernourished rats after chronic stress: opioid influence," Pharmacol Biochem Behav, 1994;47(4):789-93.
Lima, L.; Schmeer, C., "Characterization of serotonin transporter in goldfish retina by the binding of [3H]paroxetine and the uptake of [3H]serotonin: modulation by light," J Neurochem, 1994;62(2):528-35.
Lima, L.; Schmeer, C.; Urbina, M., "8-[3H]hydroxy-2-(di-n-propylamino) tetralin binding sites in goldfish retina," Neurochem Res, 1994;19(3):249-55.
Lin-Shiau, S. Y.; Hsu, K. S., "Modification of 2,2',2"-tripyridine-induced tremor in mice by serotonergic agonists and antagonists and benzodiazepines," Pharmacol Biochem Behav, 1994;48(3):665-70.
Minakami, K. "[Brain monoamines and behavior in hyperammonemic sparse-fur mice]," Nihon Yakurigaku Zasshi, 1994;103(5):219-29.
Sawynok, J.; Reid, A., "Spinal supersensitivity to 5-HT1, 5-HT2 and 5-HT3 receptor agonists following 5,7-dihydroxytryptamine," Eur J Pharmacol, 1994;264(3):249-57.
Scott, P. A.; Chou, J. M.; Tang, H.; Frazer, A., "Differential induction of 5-HT1A-mediated responses in vivo by three chemically dissimilar 5-HT1A agonists," J Pharmacol Exp Ther, 1994;270(1):198-208.
Takeda, N., "Serotonin-degradative pathways in the toad (*Bufo bufo japonicus*) brain: clues to the pharmacological analysis of human psychiatric disorders," Comparative Biochemistry and Physiology Part C: Pharmacology, Toxicology and Endocrinology, 1994;107(2):275-281.
Kärkkäinen, J.; Räisänen, M.; Huttunen, M. O.; Kallio, E.; Naukkarinen, H.; Virkkunen, M., "Urinary excretion of bufotenin (N,N-dimethyl-5-hydroxytryptamine) is increased in suspicious violent offenders: A confirmatory study," Psychiatry Research, 1995;58(2):145-152.
Kofman, O.; Levin, U., "Myo-inositol attenuates the enhancement of the serotonin syndrome by lithium," Psychopharmacology (Berl), 1995;118(2):213-8.
Mohanakumar, K. P.; Mohanty, S.; Ganguly, D. K., "Neonatal treatment with 5-HT antiserum alters 5-HT metabolism and function in adult rats," Neuroreport, 1995;7(1):238-40.
Richter, A.; Loscher, W., "Behavioural response to pharmacologic manipulation of serotonin receptors in the genetically dystonic hamster," Pharmacol Biochem Behav, 1995;52(4):655-65.
Bonson, K., "Chronic Administration of Serotonergic Antidepressants Attenuates the Subjective Effects of LSD in Humans," Neuropsychopharmacology, 1996;14(6):425-436.
Graeff, F. G.; Guimaraes, F. S.; De Andrade, T. G.; Deakin, J. F., "Role of 5-HT in stress, anxiety, and depression," Pharmacol Biochem Behav, 1996;54(1):129-41.
Kehne, J. H.; Baron, B. M.; Carr, A. A.; Chaney, S. F.; Elands, J.; Feldman, D. J.; Frank, R. A.; van Giersbergen, P. L.; McCloskey, T. C.; Johnson, M. P.; McCarty, D. R.; Poirot, M.; Senyah, Y.; Siegel, B. W.; Widmaier, C., "Preclinical characterization of the potential of the putative atypical antipsychotic MDL 100,907 as a potent 5-HT2A antagonist with a favorable CNS safety profile," J Pharmacol Exp Ther, 1996;277(2):968-81.
Netto, S. M.; Guimaraes, F. S., "Role of hippocampal 5-HT1A receptors on elevated plus maze exploration after a single restraint experience," Behav Brain Res, 1996;77(1-2):215-8.

(56) References Cited

OTHER PUBLICATIONS

Newton, R. A.; Phipps, S. L.; Flanigan, T. P.; Newberry, N. R.; Carey, J. E.; Kumar, C.; McDonald, B.; Chen, C.; Elliott, J. M., "Characterisation of human 5-hydroxytryptamine2A and 5-hydroxytryptamine2C receptors expressed in the human neuroblastoma cell line SH-SY5Y: comparative stimulation by hallucinogenic drugs," J Neurochem, 1996;67(6):2521-31.
Sánchez, C.; Arnt, J.; Moltzen, E., "Assessment of relative efficacies of 5-HT1A receptor ligands by means of in vivo animal models," European Journal of Pharmacology, 1996;315(3):245-254.
Sanchez, C.; Arnt, J.; Moltzen, E. K., "The antiaggressive potency of (−)-penbutolol involves both 5-HT1A and 5-HT1B receptors and beta-adrenoceptors," Eur J Pharmacol, 1996;297(1-2):1-8.
Thielen, R. J.; Fangon, N. B.; Frazer, A., "4-(2'-Methoxyphenyl)-1-[2'-[N-(2"-pyridinyl)-p-iodobenzamido]ethyl] piperazine and 4-(2'-methoxyphenyl)-1-[2'-[N-(2"-pyridinyl)-p-fluorobenzamido]ethyl]piperazine, two new antagonists at pre- and postsynaptic serotonin-1A receptors," J Pharmacol Exp Ther, 1996;277(2):661-70.
Cerda, J.; Petrino, T. R.; Greenberg, M. J.; Wallace, R. A., "Pharmacology of the serotonergic inhibition of steroid-induced reinitiation of oocyte meiosis in the teleost Fundulus heteroclitus," Mol Reprod Dev, 1997;48(2):282-91.
Matsumoto, K.; Mizowaki, M.; Takayama, H.; Sakai, S.; Aimi, N.; Watanabe, H., "Suppressive effect of mitragynine on the 5-methoxy-N,N-dimethyltryptamine-induced head-twitch response in mice," Pharmacol Biochem Behav, 1997;57(1-2):319-23.
Matsumoto, K.; Mizowaki, M.; Thongpraditchote, S.; Murakami, Y.; Watanabe, H., "alpha2-Adrenoceptor antagonists reverse the 5-HT2 receptor antagonist suppression of head-twitch behavior in mice," Pharmacol Biochem Behav, 1997;56(3):417-22.
Pickworth, W. B.; Henningfield, J. E., "Smokable drugs: pharmacologic basis for consumer appeal," Addiction, 1997;92(6):691-692.
Dittrich, A., "The standardized psychometric assessment of altered states of consciousness (ASCs) in humans," Pharmacopsychiatry, 1998;31 Suppl 2:80-4.
Helsley, S.; Fiorella, D.; Rabin, R. A.; Winter, J. C., "A comparison of N,N-dimethyltryptamine, harmaline, and selected congeners in rats trained with LSD as a discriminative stimulus," Progress in Neuro-Psychopharmacology and Biological Psychiatry, 1998;22(4):649-663.
Nielsen, C. K., "Head and whole-body jerking in guinea pigs are differentially modulated by 5-HT1A, 5-HT1B/1D and 5-HT2A receptor antagonists," Eur J Pharmacol, 1998;361(2-3):185-90.
Smith, R. L.; Canton, H.; Barrett, R. J.; Sanders-Bush, E., "Agonist properties of N, N-dimethyltryptamine at serotonin 5-HT2A and 5-HT2C receptors," Pharmacology Biochemistry and Behavior, 1998;61(3):323-330.
Da-Silva, V. A.; Altenburg, S. P.; Malheiros, L. R.; Thomaz, T. G.; Lindsey, C. J., "Postnatal development of rats exposed to fluoxetine or venlafaxine during the third week of pregnancy," Braz J Med Biol Res, 1999;32(1):93-8.
Jolly, D. C.; Richards, J. B.; Seiden, L. S., "Serotonergic mediation of DRL 72s behavior: receptor subtype involvement in a behavioral screen for antidepressant drugs," Biol Psychiatry, 1999;45(9):1151-62.
Pomilio, A. B.; Vitale, A. A.; Ciprian-Ollivier, J.; Cetkovich-Bakmas, M.; Gomez, R.; Vazquez, G., "Ayahoasca: an experimental psychosis that mirrors the transmethylation hypothesis of schizophrenia," J Ethnopharmacol, 1999;65(1):29-51.
Robertson, L.; Robertson, W. M.; Jones, J. T., "Direct analysis of the secretions of the potato cyst nematode *Globodera rostochiensis*," Parasitology, 1999;119 ( Pt 2):167-76.
Winter, J. C.; Helsley, S.; Fiorella, D.; Rabin, R. A., "The acute effects of monoamine reuptake inhibitors on the stimulus effects of hallucinogens," Pharmacol Biochem Behav, 1999;63(3):507-13.
Glennon, R. A.; Lee, M.; Rangisetty, J. B.; Dukat, M.; Roth, B. L.; Savage, J. E.; McBride, A.; Rauser, L.; Hufeisen, S.; Lee, D. K., "2-Substituted tryptamines: agents with selectivity for 5-HT(6) serotonin receptors," J Med Chem, 2000;43(5):1011-8.
McBride, M. C., "Bufotenine: toward an understanding of possible psychoactive mechanisms," J Psychoactive Drugs, 2000;32(3):321-31.
Sarkar, S.; Thomas, B.; Muralikrishnan, D.; Mohanakumar, K. P., "Effects of serotoninergic drugs on tremor induced by physostigmine in rats," Behav Brain Res, 2000;109(2):187-93.
Tsai, Y. et al., "N1-(Benzenesulfonyl)tryptamines as novel 5-HT6 antagonists," Bioorg Med Chem Lett, 2000;10(20):2295-9.
Bunzow, J. R. et al., "Amphetamine, 3,4-methylenedioxymethamphetamine, lysergic acid diethylamide, and metabolites of the catecholamine neurotransmitters are agonists of a rat trace amine receptor," Mol Pharmacol, 2001;60(6):1181-8.
Harris, L. C.; Awe, S. O.; Opere, C. A.; Leday, A. M.; Ohia, S. E.; Sharif, N. A., "[(3)H]-serotonin release from bovine iris-ciliary body: pharmacology of prejunctional serotonin (5-HT(7)) autoreceptors," Exp Eye Res, 2001;73(1):59-67.
Egashira, N. et al., "Involvement of 5-hydroxytryptamine neuronal system in Delta(9)-tetrahydrocannabinol-induced impairment of spatial memory," Eur J Pharmacol, 2002;445(3):221-9.
Rabin, R. A.; Regina, M.; Doat, M.; Winter, J. C., "5-HT2A receptor-stimulated phosphoinositide hydrolysis in the stimulus effects of hallucinogens," Pharmacol Biochem Behav, 2002;72(1-2):29-37.
Riba, J. et al., "Effects of ayahuasca on sensory and sensorimotor gating in humans as measured by P50 suppression and prepulse inhibition of the startle reflex, respectively," Psychopharmacology (Berl), 2002;165(1):18-28.
Thor, K. B. et al., "The role of 5-HT(1A) receptors in control of lower urinary tract function in cats," Brain Res, 2002;946(2):290-7.
De Meutter, J.; Tytgat, T.; Witters, E.; Gheysen, G.; Van Onckelen, H.; Gheysen, G., "Identification of cytokinins produced by the plant parasitic nematodes *Heterodera schachtii* and *Meloidogyne incognita*," Mol Plant Pathol, 2003;4(4):271-7.
Meatherall, R.; Sharma, P., "Foxy, a designer tryptamine hallucinogen," J Anal Toxicol, 2003;27(5):313-7.
Pullagurla, M. R. et al. "N1-benzenesulfonylgramine and N1-benzenesulfonylskatole: novel 5-HT6 receptor ligand templates," Bioorg Med Chem Lett, 2003;13(19):3355-9.
Yu, A. M.; Idle, J. R.; Herraiz, T.; Kupfer, A.; Gonzalez, F. J., "Screening for endogenous substrates reveals that CYP2D6 is a 5-methoxyindolethylamine O-demethylase," Pharmacogenetics, 2003;13(6):307-19.
Beuhler, M.; Lee, D. C.; Gerkin, R., "The Meixner test in the detection of alpha-amanitin and false-positive reactions caused by psilocin and 5-substituted tryptamines," Ann Emerg Med, 2004;44(2):114-20.
Martin-Cora, F. J.; Pazos, A., "Autoradiographic distribution of 5-HT7 receptors in the human brain using [3H] mesulergine: comparison to other mammalian species," Br J Pharmacol, 2004;141(1):92-104.
Office Action issued in HN 2021-001979 (WO2020/169851), dated Oct. 8, 2024, translation.
Office Action issued in MX/a/2021/009942 (WO2020/169851), dated Aug. 21, 2024, translation.
Office Action issued in JP 2021-549427 (WO2020/169850), dated Oct. 1, 2024, translation.
Office Action issued in JP 2021-549460 (WO2020/169851), dated Oct. 1, 2024, translation.
Office Action issued in CN 202180016407.1 (WO2021/170614), dated Oct. 30, 2024, translation.
Office Action issued in IL 289085 (WO2020/254584), dated Aug. 26, 2024, translation.
Office Action issued in MX/a/2021/009942 (WO2020/169851), dated Apr. 10, 2024, translation.
Office Action issued in AU 2020225410 (WO2020/169850), dated Nov. 1, 2024.
Office Action issued in AU 2020225766 (WO2020/169851), dated Nov. 1, 2024.
Notice of Opposition filed in EP3927337, dated Nov. 13, 2024.
Notice of Opposition filed in EP3927337, dated Nov. 14, 2024.
Consolidated List of Cited Opposition Documents in EP3927337, dated Nov. 14, 2024.

(56) References Cited

OTHER PUBLICATIONS

Toshio Hoshino et al., On the Synthesis of Bufotenin Methyl Ether (5-Methoxy-N-Dimethyl-Tryptamin) and Bufotenin (Syntheses in the Indol Group. XV), Bulletin of the Chemical Society of Japan, vol. 11, No. 3, Mar. 1936 (Mar. 1936), pp. 221-224, XP055641802, JP ISSN: 0009-2673, DOI: 10.1246/bcsj.11.221, paragraph 4, translation.
Winther, A., LSD—Verdens Mest Potente Stof er Tilbage, Anne Winther Ink Journalistik & Kommunikation, 2018, translation.
Horák et al., Bufo alvarius: evidencias literarias y controversias en torno a su uso tradicional, Medicina Naturista, 2019, 13(1), translation.
G. Blackburne et al., Complex slow waves radically reorganise human brain dynamics under 5-MeO-DMT, bioRxiv, 2024, Oct. 2024. 04.616717.
D. T. Myran et al., Emergency Department Visits Involving Hallucinogen Use and Risk of Schizophrenia Spectrum Disorder, JAMA Psychiatry, 2024, doi: 10.1001/jamapsychiatry.2024.3532.
A. E. Calder et al., Naturalistic psychedelic therapy: The role of relaxation and subjective drug effects in antidepressant response, J Psychopharmacol,2024, 38(10): 873-886, doi: 10.1177/02698811241278873.
Declaration of Mark Seelig, dated Nov. 13, 2024.
Riga et al., The serotonin hallucinogen 5-MeO-DMT alters corticothalamic activity in freely moving mice: Regionally-selective involvement of 5-HT1A and 5-HT2A receptors, Neuropharmacology, Nov. 2018, 142.
Stafford, Psychedelics Encyclopedia, 1993 3rd Edition.
Document summarising the use of the terms "depression" and "treatment-resistant depression" by the Patentee of EP 3927337 in their public communications, 2021.
Corporate presentation from the Patentee of EP 3927337, dated Mar. 2022.
Corporate presentation from the Patentee of EP 3927337, dated May 2022.
Corporate presentation from the Patentee of EP 3927337, dated Nov. 2022.
Corporate presentation from the Patentee of EP 3927337, dated Mar. 2023.
Corporate presentation from the Patentee of EP 3927337, dated May 2023.
Press release from the Patentee of EP 3927337, dated Apr. 12, 2021.
Press release from the Patentee of EP 3927337, dated Sep. 3, 2024.
Archived version of "The Essential Guide to 5-MEO-DMT" produced by Third Wave, as it appeared on Nov. 9, 2018: https://web.archive.org/web/20181109024846/https://thethirdwave.co/psychedelics/5-meodmt/, Also available at: https://archive.ph/c11Dw.
Clinical trial disclosure: "A phase ½ study of GH001 in patients with treatment-resistant depression", EudraCT No. 2018-004208-20, Sponsor's Protocol Code No. GH001-MDD-3e2. Also available https://web.archive.org/web/20210729022042/https://www.clinicaltrialsreQister.eu/ctrsearch/trial/2018-004208-20/NL, dated at least Aug. 21, 2019.
EudraCT & EU CTR Question and Answer table, Frequently Asked Questions & Answers (FAQs)—V1.3, Mar. 2019.
Kaufman J et al., The 5-HT1A receptor in Major Depressive Disorder, Eur Neuropsychopharmacol. Mar. 2016; 26(3):397-410. doi: 10.1016/j.euroneuro.2015.12.039. Epub Jan. 11, 2016. PMID: 26851834; PMCID: PMC5192019.
Form F-1 (Registration Statement Under Securities Act 1933) filed by GH Research PLC (of which GH Research is a subsidiary) with the Securities and Exchange Commission on Jun. 21, 2021.
Birnbaum HG et al., Employer burden of mild, moderate, and severe major depressive disorder: Mental health services utilization and costs , and work performance, Depress Anxiety, 2010;27(1):78-89.
Cowen P., Altered states: psilocybin for treatment-resistant depression, Lancet Psychiatry, Jul. 2016, 3(7):592-3. doi: 10.1016/S2215-0366(16)30087-6. Epub May 17, 2016. PMID: 27210032.
Meccia J et al., Treatment of major depressive disorder and treatment resistant depression with 5-MeO-DMT: impact of 25 years of non-traditional public scientific communication and education on clinical development and commercialization. Manuscript published online Nov. 12, 2024 at: https://www.portasophia.org/files/claimscharts/Meccia-et-al-2024-5-MeO-DMT.pdf. Also available online at: https://web.archive.org/web/20241112195128/https://www.portasophia.org/files/claimscharts/Meccia-et-al-2024-5-MeO-DMT.pdf.
Archived version of a press release entitled "Porta Sophia Publishes Narrative Review Manuscript Summarizing Historical Evidence of 5-MeO-DMT as a Compound Used in 4Therapeutic Practice" issued on Nov. 12, 2024, as it appeared on Nov. 12, 2024: https://web.archive.org/web/20241112194425/https://www.portasophia.org/newsroom/pressreleases/porta-sophia-publishes-narrative-review-manuscript-summarizing-historicalevidence-of-5-meo-dmt-as-a-compound-used-in-therapeutic-practice Also available via: https://archive.ph/L VILs.
B. Malcolm et al., Serotonin toxicity of serotonergic psychedelics, Psychopharmacology (Berl), 2022, vol. 239(6): 1881-1891, doi: 10.1007/s00213-021-05876-x.
S. T. Aaronson et al., Single-Dose Synthetic Psilocybin With Psychotherapy for Treatment-Resistant Bipolar Type II Major Depressive Episodes: A Nonrandomized Controlled Trial, JAMA Psychiatry, 2023, doi: 10.1001/jamapsychiatry.2023.4685.
N. L. Mason et al., Sub-Acute Effects of Psilocybin on Empathy, Creative Thinking, and Subjective Well-Being, J Psychoactive Drugs, 2019, pp. 1-12, doi: 10.1080/02791072.2019.1580804.
L. Pasquini et al., Subacute effects of the psychedelic ayahuasca on the salience and default mode networks, J Psychopharmacol, 2020, vol. 34(6): 623-635, doi: 10.1177/0269881120909409.
A. Nikolaidis et al., Subtypes of the psychedelic experience have reproducible and predictable effects on depression and anxiety symptoms, J Affect Disord, 2022, doi: 10.1016/j.jad.2022.12.042.
Hive, Suggested Dosing Protocol from the T.O.A.D., 2018.
G. M. Knudsen, Sustained effects of single doses of classical psychedelics in humans, Neuropsychopharmacology, 2022, doi: 10.1038/s41386-022-01361-x.
A. M. Sherwood et al., Synthesis and Characterization of 5-MeO-DMT Succinate for Clinical Use, ACS Omega, 2020, vol. 5(49): 32067-32075, doi: 10.1021/acsomega.0c05099.
N. V. Cozzi et al., Synthesis and characterization of high-purity N, N-dimethyltryptamine hemifumarate for human clinical trials, Drug Testing and Analysis, 2020, vol. 12(10): 1483-1493.
A. A. de Deus Pontual et al., Systematic Review of Psychometric Instruments Used in Research with Psychedelics, J Psychoactive Drugs, 2022, pp. 1-10, doi: 10.1080/02791072.2022.2079108.
E. A. Schindler, Table 1: Summary of neuroendocrine associations, 2018.
R. L. Carhart-Harris et al., The administration of psilocybin to healthy, hallucinogen-experienced volunteers in a mock-functional magnetic resonance imaging environment: a preliminary investigation of tolerability, J Psychopharmacol, 2011, vol. 25(11): 1562-7, doi: 10.1177/0269881110367445.
A. H. Young, The age of psychedelics, J Psychopharmacol, 2022, vol. 36(1): 3-5, doi: 10.1177/02698811211070065.
M. Falchi-Carvalho, "The antidepressant effects of vaporized N,N-Dimethyltryptamine: a preliminary report in treatment-resistant depression," Brazilian Journal of Psychiatry as Brief Communication, 2024, doi: 10.1101/2024.01.03.23300610.
J. S. Chambers, The Buzz 2: Usual Suspect. In Birkholz death, alcohol, drug abuse were largely glossed over, 2018.
J. T. Reckweg et al., The clinical pharmacology and potential therapeutic applications of 5-methoxy-N,N-dimethyltryptamine (5-MeO-DMT), J Neurochem, 2022, vol. 162(1): 128-146, doi: 10.1111/jnc.15587.
S. L. So, R. et al., The Z of 5-Methoxy-N,N-Dimethyltryptamine (5-MeO-DMT) are associated with improvements in depression and anxiety conditions, 2018.
E. Marseille et al., The economics of psychedelic-assisted therapies: A research agenda, Front Psychiatry, 2022, vol. 13, doi: 10.3389/fpsyt.2022.1025726.
D. Dudysová et al., The effects of daytime psilocybin administration on sleep: implications for antidepressant action, Frontiers in pharmacology, 2020, vol. 11, 602590.

(56) References Cited

OTHER PUBLICATIONS

S. Yanakieva et al., The effects of microdose LSD on time perception: a randomised, double-blind, placebo-controlled trial, Psychopharmacology (Berl), 2019, vol. 236(4): 1159-1170, doi: 10.1007/s00213-018-5119-x.

J. J. Rucker et al., The effects of psilocybin on cognitive and emotional functions in healthy participants: Results from a phase 1, randomised, placebo-controlled trial involving simultaneous psilocybin administration and preparation, J Psychopharmacol, 2022, vol. 36(1): 114-125, doi: 10.1177/02698811211064720.

J. Castelhano et al., The Effects of Tryptamine Psychedelics in the Brain: A meta-Analysis of Functional and Review of Molecular Imaging Studies, Front Pharmacol, 2021, vol. 12, doi: 10.3389/fphar.2021.739053.

R. L. Carhart-Harris, The entropic brain—revisited, Neuropharmacology, 2018, doi: 10.1016/j.neuropharm.2018.03.010.

R. J. Zeifman et al., The Impact of Ayahuasca on Suicidality: Results From a Randomized Controlled Trial, Front Pharmacol, 2019, vol. 10, p. 1325, doi: 10.3389/fphar.2019.01325.

C. Kraus et al., The influence of ketamine on drug discovery in depression, Drug Discov Today, 2019, vol. 24(10): 2033-2043, doi: 10.1016/j.drudis.2019.07.007.

B. R. Barksdale et al., "The mechanistic divide in psychedelic neuroscience: An unbridgeable gap?" Neurotherapeutics, 2024, doi: 10.1016/j.neurot.2024.e00322.

B. L. Roth et al., "The Multiplicity of Serotonin Receptors: Uselessly Diverse Molecules or an Embarrassment of Riches?" The Neuroscientist, 2016, vol. 6(4): 252-262, doi: 10.1177/107385840000600408.

S. Ruffell et al, The pharmacological interaction of compounds in ayahuasca: a systematic review, Braz J Psychiatry, 2020, vol. 42(6): 646-656, doi: 10.1590/1516-4446-2020-0884.

T. Mishraki-Berkowitz et al., The Psilocin (4-hydroxy-N,N-dimethyltryptamine) and Bufotenine (5-hydroxy-N,N-dimethyltryptamine) Case: Ensuring the Correct Isomer has Been Identified, J Forensic Sci, 2020, vol. 65(5): 1450-1457, doi: 10.1111/1556-4029.14368.

K. Gillin, The psychedelic model of schizophrenia: the case of N, N-dimethyltryptamine, 2007.

G. Hilaire et al., The role of serotonin in respiratory function and dysfunction, Respir Physiol Neurobiol, 2010, vol. 174(1-2):76-88, doi: 10.1016/j.resp.2010.08.017.

B. E. McGeeney, The Science Behind Psychedelics for Cluster Headache, 2018.

E. W. Boyer et al., The serotonin syndrome, N Engl J Med, 2005, vol. 352(11):1112-20, doi: 10.1056/NEJMra041867.

D. B. Yaden et al., The Subjective Effects of Psychedelics Are Necessary for Their Enduring Therapeutic Effects, ACS Pharmacol Transl Sci, 2021, vol. 4(2): 568-572, doi: 10.1021/acsptsci.0c00194.

D. E. Olson, The Subjective Effects of Psychedelics May Not Be Necessary for Their Enduring Therapeutic Effects, ACS Pharmacol Transl Sci, 2021, vol. 4(2); 563-567, doi: 10.1021/acsptsci.0c00192.

T. R. Wave, The Ultimate Guide to 5-MeO-DMT, 2018.

J. S. Kurtz et al., The Use of Psychedelics in the Treatment of Medical Conditions: An Analysis of Currently Registered Psychedelics Studies in the American Drug Trial Registry, Cureus, 2022, vol. 14(9), doi: 10.7759/cureus.29167.

M. Marks, The varieties of psychedelic law, Neuropharmacology, 2022, doi: 10.1016/j.neuropharm.2022.109399.

J. Bornemann, The Viability of Microdosing Psychedelics as a Strategy to Enhance Cognition and Well-being—An Early Review, J Psychoactive Drugs, 2020, vol. 52(4):300-308, doi: 10.1080/02791072.2020.1761573.

R. Murphy et al., Therapeutic Alliance and Rapport Modulate Responses to Psilocybin Assisted Therapy for Depression, Front Pharmacol, 2021, vol. 12, doi: 10.3389/fphar.2021.788155.

K. van Oorsouw et al., Therapeutic effect of an ayahuasca analogue in clinically depressed patients: a longitudinal observational study, Psychopharmacology (Berl), 2022, vol. 239(6): 1839-1852, doi: 10.1007/s00213-021-06046-9.

K. A. A. Andersen et al., Therapeutic effects of classic serotonergic psychedelics: A systematic review of modern-era clinical studies, Acta Psychiatr Scand, 2021, vol. 143(2): 101-118, doi: 10.1111/acps.13249.

L. J. Mertens et al., Therapeutic mechanisms of psilocybin: Changes in amygdala and prefrontal functional connectivity during emotional processing after psilocybin for treatment-resistant depression, J Psychopharmacol, 2020, vol. 34(2): 167-180, doi: 10.1177/0269881119895520.

B. D. Heifets et al., Therapeutic mechanisms of psychedelics and entactogens, Neuropsychopharmacology, 2023, doi: 10.1038/s41386-023-01666-5.

A. Hosanagar et al., Therapeutic Potential of Psychedelics in the Treatment of Psychiatric Disorders, Part 1: Psychopharmacology and Neurobiological Effects, J Clin Psychiatry, 2021, vol. 82(2), doi: 10.4088/JCP.20ac13786.

A. Hosanagar et al., Therapeutic Potential of Psychedelics in Treatment of Psychiatric Disorders, Part 2: Review of the Evidence, J Clin Psychiatry, 2021, vol. 82(3), doi: 10.4088/JCP.20ac13787.

S. Ross, Therapeutic use of classic psychedelics to treat cancer-related psychiatric distress, Int Rev Psychiatry, 2018, vol. 30(4): 317-330, doi: 10.1080/09540261.2018.1482261.

R. G. Dos Santos et al., Therapeutic use of serotoninergic hallucinogens: A review of the evidence and of the biological and psychological mechanisms, Neurosci Biobehav Rev, 2020, vol. 108: 423-434, doi: 10.1016/j.neubiorev.2019.12.001.

S. P. Singleton et al., Time-resolved network control analysis links reduced control energy under DMT with the serotonin 2a receptor, signal diversity, and subjective experience, bioRxiv, 2023, doi: 10.1101/2023.05.11.540409.

Toxline, Tox publications, 2018.

A. Y. Simao et al., Toxicological Aspects and Determination of the Main Components of Ayahuasca: A Critical Review, Medicines (Basel), 2019, vol. 6(4), doi: 10.3390/medicines6040106.

J. Keppel Hesselink, Transformation and Migration of Healing Rituals from Indigenous Cultures to the West: Amphibian Secretions, the 'Frog Medicine and Toad Medicine',Sm J Psychiatry Ment Health, 2019.

J. M. K. Hesselink et al., Transformative Psychopharmacology: the Case of 5-Methoxy-N,N-Dimethyltryptamine, International Journal of Psychotherapy Practice and Research, 2019, vol. 1(3): 9-15, doi: 10.14302/issn.2574-612X.ijpr-18-2503.

C. Ly et al., Transient Stimulation with Psychoplastogens Is Sufficient to Initiate Neuronal Growth, ACS Pharmacol Transl Sci, 2021, vol. 4(2): 452-460, doi: 10.1021/acsptsci.0c00065.

TRD Questions, 2018.

Ennis, C. et al., "Characterisation of inhibitory 5-hydroxytryptamine receptors that modulate dopamine release in the striatum," *J Neurochem*, 1981;36(4):1515-20.

Glennon, R. A. et al., "Behavioral properties of psychoactive phenylisopropylamines in rats," *Eur J Pharmacol*, 1981;76(4):353-60.

Green, A. R. "Pharmacological studies on serotonin-mediated behaviour," *J Physiol* (Paris), 1981;77(2-3):437-47.

Kuhn, C. M. et al., "Effect of 5,7-dihydroxytryptamine on serotonergic control of prolactin secretion and behavior in rats," *Psychopharmacology* (Berl), 1981;73(2):188-93.

Laubscher, A. P., A. et al., "Interaction of D-LSD with blood platelets of rabbits: shape change and specific binding," *J Pharmacol Exp Ther*, 1981.

Migliaccio, G. P. et al., "Comparison of solution conformational preferences for the hallucinogens bufotenin and psilocin using 360-MHz proton NMR spectroscopy," J Med Chem, 1981;24(2):206-9.

Mueller, R. A. et al., "Alteration of aminophylline-induced respiratory stimulation by perturbation of biogenic amine systems," *J Pharmacol Exp Ther*, 1981;218(3):593-9.

Ortmann, R. et al., "Supersensitivity to L-5-hydroxytryptophan after 5,7-dihydroxytryptamine injections in desmethylimipramine- and nomifensine-pretreated rats: behavioral evidence for postsynaptic supersensitivity," *Psychopharmacology* (Berl), 1981;74(2):109-14.

(56) References Cited

OTHER PUBLICATIONS

Schlemmer, R. F., Jr. et al., "Evidence for dopamine mediation of submissive gestures in the stumptail macaque monkey," *Pharmacol Biochem Behav*, 1981;14 Suppl 1:95-102.
Shimizu, T. "[Effects of peripheral electric stimulation on the central 5-hydroxytryptamine in mice: relation to the peripheral stimulation-produced analgesia] (author's transl)," *Nihon Yakurigaku Zasshi*, 1981;77(4):347-60.
Wiklund, L. et al., "Morphological and functional studies on the serotoninergic innervation of the inferior olive," *J Physiol* (*Paris*), 1981;77(2-3):183-6.
Archer, T. et al., "Serotonin involvement in aversive conditioning: reversal of the fear retention deficit by long-term p-chloroamphetamine but not p-chlorophenylalanine," *Neurosci Lett*, 1982;34(1):75-82.
Berge, O. G. "Effects of 5-HT receptor agonists and antagonists on a reflex response to radiant heat in normal and spinally transected rats," *Pain*, 1982;13(3):253-266.
Blackburn, T. P. et al., "Possible mechanism of 5-methoxy-N,N-dimethyltryptamine-induced turning behaviour in DRN lesioned rats," *Pharmacol Biochem Behav*, 1982;16(1):7-11.
Blackburn, T. P. et al., "Involvement of a central dopaminergic system in 5-methoxy-N,N-dimethyltryptamine-induced turning behaviour in rats with lesions of the dorsal raphe nuclei," *Psychopharmacology* (*Berl*), 1982;78(3):261-5.
Blackshear, M. A. et al., "Serotonin receptor sensitivity after acute and chronic treatment with mianserin," *J Pharmacol Exp Ther*, 1982;221(2):303-8.
Clemens, J. A. et al., "Inhibition of prolactin release by stimulation of presynaptic serotonin autoreceptors," *Life Sci*, 1982;31(23):2641-6.
Glennon, R. A. et al., "Hallucinogens as discriminative stimuli: a comparison of 4-OMe DMT and 5-OMe DMT with their methythio counterparts," *Life Sci*, 1982;30(5):465-7.
Glennon, R. A. et al., "Discriminative stimulus properties of DOM and several molecular modifications," *Pharmacology Biochemistry and Behavior*, 1982;16(4):553-556.
Heym, J. et al., "Activity of serotonin-containing neurons in the nucleus raphe pallidus of freely moving cats," *Brain Res*, 1982;251(2):259-76.
Kato, S. et al., "5-hydroxytryptamine stimulates [3H]dopamine release from the fish retina," *J Neurochem*, 1982;39(2):493-8.
Kline, T. B. et al. "Structure-activity relationships for hallucinogenic N,N-dialkyltryptamines: photoelectron spectra and serotonin receptor affinities of methylthio and methylenedioxy derivatives," *J Med Chem*, 1982;25(11):1381-3.
Lalley, P. M., "Inhibition of phrenic and sympathetic vasomotor neurons in cats by the serotonin analog 5-methoxy-N,N-dimethyltryptamine," *J Pharmacol Exp Ther*, 1982;220(1):39-48.
Larson, A. A., "Nociception is enhanced by the intrathecal injection of 5-methoxy-N,N-dimethyltryptamine in the rat," *Neurosci Lett*, 1982;33(3):323-8.
Lucki, I., et al., "Prevention of the serotonin syndrome in rats by repeated administration of monoamine oxidase inhibitors but not tricyclic antidepressants," *Psychopharmacology* (*Berl*), 1982;77(3):205-11.
Rebec, G. V. et al., "Dorsal raphe neurons: self-inhibition by an amphetamine-induced release of endogenous serotonin," *Brain Res*, 1982;251(2):374-9.
Shephard, R. A. et al., "Effects of diazepam and of serotonin agonists on hyponeophagia in rats," *Neuropharmacology*, 1982;21(4):337-40.
Shephard, R. A. et al., "Beta-adrenoceptor antagonists may attenuate hyponeophagia in the rat through a serotonergic mechanism," *Pharmacol Biochem Behav*, 1982;16(5):741-4.
Slater, P. et al., "Effects of intrapallidal drugs on hyperactivity induced by nucleus accumbens dopamine receptor stimulation," *Naunyn Schmiedebergs Arch Pharmacol*, 1982;321(3):201-6.
Tricklebank, M. D. et al., "Analgesia induced by brief footshock is inhibited by 5-hydroxytryptamine but unaffected by antagonists of 5-hydroxytryptamine or by naloxone," *Neuropharmacology*, 1982;21(1):51-6.
Vandermaelen, C. P. et al., "Intracellular studies on the effects of systemic administration of serotonin agonists on rat facial motoneurons," *Eur J Pharmacol*, 1982;78(2):233-6.
White, F. J. et al., "The role of dopamine and serotonin in the discriminative stimulus effects of lisuride," *J Pharmacol Exp Ther*, 1982;221(2):421-7.
White, F. J. et al., "Training dose as a factor in LSD-saline discrimination," *Psychopharmacology* (*Berl*), 1982;76(1):20-5.
Young, R. et al., "Comparative discriminative stimulus effects of 5-methoxy-N,N-dimethyltryptamine and LSD," *Life Sci*, 1982;30(24):2057-62.
Barbaccia, M. L.; Brunello, N.; Chuang, D. M.; Costa, E., "Serotonin-elicited amplification of adenylate cyclase activity in hippocampal membranes from adult rat," *J Neurochem*, 1983;40(6):1671-9.
Berge, O. G. et al., "Serotonin receptor antagonists induce hyperalgesia without preventing morphine antinociception," *Pharmacol Biochem Behav*, 1983;19(5):873-8.
Dickinson, S. L. et al., "Roles of dopamine and 5-hydroxytryptamine in stereotyped and non-stereotyped behaviour," *Neuropharmacology*, 1983;22(7):805-12.
Dickinson, S. L. et al., "Effect of apomorphine on behaviour induced by 5-methoxy-N, N-dimethyl tryptamine: three different scoring methods give three different conclusions," *Psychopharmacology* (*Berl*), 1983;80(2):196-7.
Erowid, "The Sonoran Desert Toad, practical guide," 1983.
Glennon, R. A. et al., "Antagonism of the effects of the hallucinogen DOM and the purported 5-HT agonist quipazine by 5-HT2 antagonists," *Eur J Pharmacol*, 1983;91(2-3):189-96.
Hutson, P. H. et al. "Analgesia induced by brief footshock: blockade by fenfluramine and 5-methoxy-N,N-dimethyltryptamine and prevention of blockade by 5-HT antagonists," *Brain Res*, 1983;279(1-2):105-10.
Kalkman, H. O. et al., "Calcium-dependency of the pressor responses to selective 5-hydroxytryptamine receptor agonists in pithed rats," *J Auton Pharmacol*, 1983;3(4):281-6.
Kato, S. et al., "5-hydroxytryptamine: its facilitative action on [3H]dopamine release from the retina," *Vision Res*, 1983;23(4):445-9.
Kitada, Y. et al., "Involvement of alpha- and beta 1-adrenergic mechanisms in the immobility-reducing action of desipramine in the forced swimming test," *Neuropharmacology*, 1983;22(9):1055-60.
Long, J. B. et al., "Regional differences in the response of serotonergic neurons in rat CNS to drugs," *Eur J Pharmacol*, 1983;88(1):89-97.
Santos, R. et al., "Serotonin receptor activation in rats previously deprived of REM sleep," *Pharmacol Biochem Behav*, 1983;18(4):501-7.
Shephard, R. A. et al., "Hyponeophagia in the Roman rat strains: effects of 5-methoxy-N,N-dimethyltryptamine, diazepam, methysergide and the stereoisomers of propranolol," *Eur J Pharmacol*, 1983;95(3-4):177-84.
Trulson, M. E. et al., "Mescaline elicits behavioral effects in cats by an action at both serotonin and dopamine receptors," *Eur J Pharmacol*, 1983;96(1-2):151-4.
Uebelhack, R. et al., "Methylated and unmethylated indolamine in the cisternal fluid in acute endogenous psychoses," *Biomed Biochim Acta*, 1983;42(10):1343-6.
Whipple, M. R. et al., "Inhibition of synaptosomal neurotransmitter uptake by hallucinogens," *J Neurochem*, 1983;40(4):1185-8.
Youdim, M. B. et al., "Brain Iron and Dopamine Receptor Function," *Advances in biochemical psychopharmacology*, 1983;37:309-321.
Archer, T. et al., "Effects of acute administration of 5-methoxy-N,N-dimethyltryptamine upon the latency and duration of post-decapitation convulsions," *Acta Pharmacol Toxicol* (*Copenh*), 1984;55(3):224-30.
Arnt, J. et al., "Changes in rat dopamine- and serotonin function in vivo after prolonged administration of the specific 5-HT uptake inhibitor, citalopram," *Psychopharmacology* (*Berl*), 1984;84(4):457-65.

(56) References Cited

OTHER PUBLICATIONS

Beaton, J. M. et al., “Ontogeny of N,N-dimethyltryptamine and related indolealkylamine levels in neonatal rats,” *Mech Ageing Dev*, 1984;25(3):343-7.
Bundman, M. C. et al., “In vivo increase in hypothalamic cyclic AMP following 5-hydroxytryptophan administration in rats,” *Naunyn Schmiedebergs Arch Pharmacol*, 1984;327(3):214-20.
McKenna, D. J., “Clinical investigations of the therapeutic potential of ayahuasca: rationale and regulatory challenges,” Pharmacol Ther, 2004;102(2):111-29.
Vorce, S. P.; Sklerov, J. H., “A general screening and confirmation approach to the analysis of designer tryptamines and phenethylamines in blood and urine using GC-EI-MS and HPLC-electrospray-MS,” J Anal Toxicol, 2004;28(6):407-10.
Costa, T. O.; Morales, R. A.; Brito, J. P.; Gordo, M.; Pinto, A. C.; Bloch, C., Jr., “Occurrence of bufotenin in the Osteocephalus genus (*Anura: hylidae*),” Toxicon, 2005;46(4):371-5.
Ikeda, A.; Sekiguchi, K.; Fujita, K.; Yamadera, H.; Koga, Y., “5-methoxy-N,N-diisopropyltryptamine-induced flashbacks,” Am J Psychiatry, 2005;162(4):815.
Isbister, G. K.; Buckley, N. A., “The pathophysiology of serotonin toxicity in animals and humans: implications for diagnosis and treatment,” Clin Neuropharmacol, 2005;28(5):205-14.
Karkkainen, J.; Forsstrom, T.; Tornaeus, J.; Wahala, K.; Kiuru, P.; Honkanen, A.; Stenman, U. H.; Turpeinen, U.; Hesso, A., “Potentially hallucinogenic 5-hydroxytryptamine receptor ligands bufotenine and dimethyltryptamine in blood and tissues,” Scand J Clin Lab Invest, 2005;65(3):189-99.
Matsumoto, K.; Morishige, R.; Murakami, Y.; Tohda, M.; Takayama, H.; Sakakibara, I.; Watanabe, H., “Suppressive effects of isorhynchophylline on 5-HT2A receptor function in the brain: behavioural and electrophysiological studies,” Eur J Pharmacol, 2005;517(3):191-9.
swgdrug.org, “Bufotenine Chemical Details,” 2005.
Fantegrossi, W. E.; Harrington, A. W.; Kiessel, C. L.; Eckler, J. R.; Rabin, R. A.; Winter, J. C.; Coop, A.; Rice, K. C.; Woods, J. H., “Hallucinogen-like actions of 5-methoxy-N,N-diisopropyltryptamine in mice and rats,” Pharmacol Biochem Behav, 2006;83(1):122-9.
Kaumann, A. J.; Levy, F. O., “5-hydroxytryptamine receptors in the human cardiovascular system,” Pharmacol Ther, 2006;111(3):674-706.
Moretti, C.; Gaillard, Y.; Grenand, P.; Bevalot, F.; Prevosto, J. M., “Identification of 5-hydroxy-tryptamine (bufotenine) in takini (*Brosimumacutifolium huber* subsp. *acutifolium* C.C. Berg, Moraceae), a shamanic potion used in the Guiana Plateau,” J Ethnopharmacol, 2006;106(2):198-202.
Sandoval Isaac, G. R., “Vaporizing 5-MeO-DMT From Bufo Alvarius as an Entheogen: A Retrospective Case Control Study,” The God Molecule: 5-MeO-DMT and the Spiritual Path to the Divine Light, 2006.
Tsujikawa, K.; Mohri, H.; Kuwayama, K.; Miyaguchi, H.; Iwata, Y.; Gohda, A.; Fukushima, S.; Inoue, H.; Kishi, T., “Analysis of hallucinogenic constituents in Amanita mushrooms circulated in Japan,” Forensic Sci Int, 2006;164(2-3):172-8.
Erowid, “The Sonoran Desert Toad, 5-MeO-DMT content,” 2007.
Erowid, “The Sonoran Desert Toad, dose,” 2007.
Erowid, “The Sonoran Desert Toad, how to smoke,” 2007.
Taylor Tavares, J. V.; Clark, L.; Cannon, D. M.; Erickson, K.; Drevets, W. C.; Sahakian, B. J., “Distinct profiles of neurocognitive function in unmedicated unipolar depression and bipolar II depression,” Biol Psychiatry, 2007;62(8):917-24.
Winkelman, M. J., “Shamanic guidelines for psychedelic medicine,” Psychedelic medicine: New evidence for hallucinogenic substances as treatments, 2007;2:143-167.
Barbanoj, M. J.; Riba, J.; Clos, S.; Gimenez, S.; Grasa, E.; Romero, S., “Daytime Ayahuasca administration modulates REM and slow-wave sleep in healthy volunteers,” Psychopharmacology (Berl), 2008;196(2):315-26.
Dea, “FDA Basis for the Recommendation to Control 5-Methoxy-DMT,” 2008.
Fantegrossi, W. E.; Murnane, K. S.; Reissig, C. J., “The behavioral pharmacology of hallucinogens Biochem Pharmacol,” 2008;75(1):17-33.
Gan, N.; Yang, X.; Li, T. H.; He, P., “[Studies on constituents of rootsanel leaves from Desmodium blandum and their cytotoxic activity against growth of several tumor cells],” Zhongguo Zhong Yao Za Zhi, 2008;33(18):2077-80.
González-Maeso, J.; Ang, R. L.; Yuen, T.; Chan, P.; Weisstaub, N. V.; López-Giménez, J. F.; Zhou, M.; Okawa, Y.; Callado, L. F.; Milligan, G., “Identification of a serotonin/glutamate receptor complex implicated in psychosis,” Nature, 2008;452(7183):93-97.
Hardeland, R., “Melatonin, hormone of darkness and more: occurrence, control mechanisms, actions and bioactive metabolites,” Cell Mol Life Sci, 2008;65(13):2001-18.
Maps, “Clinical Study Protocol—Psilocybin-assisted Psychotherapy in the Management of Anxiety Associated With Stage IV Melanoma,” 2008.
Sano, K.; Mishima, K.; Koushi, E.; Orito, K.; Egashira, N.; Irie, K.; Takasaki, K.; Katsurabayashi, S.; Iwasaki, K.; Uchida, N.; Egawa, T.; Kitamura, Y.; Nishimura, R.; Fujiwara, M., “Delta 9-tetrahydrocannabinol-induced catalepsy-like immobilization is mediated by decreased 5-HT neurotransmission in the nucleus accumbens due to the action of glutamate-containing neurons,” Neuroscience, 2008;151(2):320-8.
Spectrum, “Material Safety, Data Sheet—5-Methoxy-N,N-dimethyltryptamine,” 2008.
Gatch, M. B.; Rutledge, M. A.; Carbonaro, T.; Forster, M. J., “Comparison of the discriminative stimulus effects of dimethyltryptamine with different classes of psychoactive compounds in rats,” Psychopharmacology (Berl), 2009;204(4):715-24.
Hanna, J., “Psychedelic Resource List,” 2009.
Wallach, J. V., “Endogenous hallucinogens as ligands of the trace amine receptors: a possible role in sensory perception,” Med Hypotheses, 2009;72(1):91-4.
Wang, M. J.; Tsai, C. H.; Hsu, W. Y.; Liu, J. T.; Lin, C. H., “Optimization of separation and online sample concentration of N,N-dimethyltryptamine and related compounds using MEKC,” J Sep Sci, 2009;32(3):441-5.
Winter, J. C., “Hallucinogens as discriminative stimuli in animals: LSD, phenethylamines, and tryptamines,” Psychopharmacology (Berl), 2009;203(2):251-63.
Carhart-Harris, R. L.; Nutt, D. J., “User perceptions of the benefits and harms of hallucinogenic drug use: A web-based questionnaire study Journal of Substance Use,” 2010;15(4):283-300.
Drug Enforcement Administration, D. o. J., “Schedules of controlled substances: placement of 5-methoxy-N,N-dimethyltryptamine into Schedule I of the Controlled Substances Act. Final rule,” Fed Regist, 2010;75(243):79296-300.
Rao, D.; Basura, G. J.; Roche, J.; Daniels, S.; Mancilla, J. G.; Manis, P. B., “Hearing loss alters serotonergic modulation of intrinsic excitability in auditory cortex,” J Neurophysiol, 2010;104(5):2693-703.
Romano, A. G.; Quinn, J. L.; Li, L.; Dave, K. D.; Schindler, E. A.; Aloyo, V. J.; Harvey, J. A., “Intrahippocampal LSD accelerates learning and desensitizes the 5-HT(2A) receptor in the rabbit, Romano et al.” Psychopharmacology (Berl),2010;212(3):441-8.
Baggott, M. J.; Coyle, J. R.; Erowid, E.; Erowid, F.; Robertson, L. C., “Abnormal visual experiences in individuals with histories of hallucinogen use: a Web-based questionnaire,” Drug Alcohol Depend, 2011;114(1):61-7.
Bitter, C., “Transmucosal nasal drug delivery—Pharmacokinetics and Pharmacodynamics of Nasally Applied Esketamine,” Philosophisch-Naturwissenschaftlichen Fakultät, 2011.
Halberstadt, A. L.; Geyer, M. A., “Multiple receptors contribute to the behavioral effects of indoleamine hallucinogens,” Neuropharmacology, 2011;61(3):364-381.
Hill, S. L.; Thomas, S. H., “Clinical toxicology of newer recreational drugs,” Clin Toxicol (Phila), 2011;49(8):705-19.
Corkery, J. M.; Durkin, E.; Elliott, S.; Schifano, F.; Ghodse, A. H., “The recreational tryptamine 5-MeO-DALT (N,N-diallyl-5-methoxytryptamine): a brief review,” Prog Neuropsychopharmacol Biol Psychiatry, 2012;39(2):259-62.

(56) References Cited

OTHER PUBLICATIONS

Maclean, K. A.; Leoutsakos, J. M.; Johnson, M. W.; Griffiths, R. R., "Factor Analysis of the Mystical Experience Questionnaire: A Study of Experiences Occasioned by the Hallucinogen Psilocybin," J Sci Study Relig, 2012;51(4):721-737.

Nichols, D. E., "Structure-activity relationships of serotonin 5-HT2A agonists," Wiley Interdisciplinary Reviews: Membrane Transport and Signaling, 2012;1(5):559-579.

Owens, J.; Provenza, F. D.; Wiedmeier, R. D.; Villalba, J. J., "Influence of saponins and tannins on intake and nutrient digestion of alkaloid-containing foods," J Sci Food Agric, 2012;92(11):2373-8.

Hanks, J. B.; Gonzalez-Maeso, J., "Animal models of serotonergic psychedelics," ACS Chem Neurosci, 2013;4(1):33-42.

Krebs, T. S.; Johansen, P. O., "Psychedelics and mental health: a population study," PLoS One, 2013;8(8):e63972.

Martin, R.; Schurenkamp, J.; Gasse, A.; Pfeiffer, H.; Kohler, H., "Determination of psilocin, bufotenine, LSD and its metabolites in serum, plasma and urine by SPE-LC-MS/MS," Int J Legal Med, 2013;127(3):593-601.

Passie, T., "Aktuelle Forschung mit Halluzinogenen und Entaktogenen (1985 bis 2013)," 2013.

Servillo, L.; Giovane, A.; Balestrieri, M. L.; Casale, R.; Cautela, D.; Castaldo, D., "Citrus genus plants contain N-methylated tryptamine derivatives and their 5-hydroxylated forms," J Agric Food Chem, 2013;61(21):5156-62.

Govare, A.; Leroux, E., "Licit and illicit drug use in cluster headache," Curr Pain Headache Rep, 2014;18(5):413.

Shpakova, E. A.; Derkach, K. V.; Shpakov, A. O., "Effect of peptides corresponding to extracellular domains of serotonin 1B/ID receptors and melanocortin 3 and 4 receptors on hormonal regulation of adenylate cyclase in rat brain," Bull Exp Biol Med, 2014;156(5):658-62.

Vigerelli, H.; Sciani, J. M.; Jared, C.; Antoniazzi, M. M.; Caporale, G. M.; da Silva Ade, C.; Pimenta, D. C., "Bufotenine is able to block rabies virus infection in BHK-21 cells," J Venom Anim Toxins Incl Trop Dis, 2014;20(1):45.

Bogenschutz, M. P.; Forcehimes, A. A.; Pommy, J. A.; Wilcox, C. E.; Barbosa, P. C.; Strassman, R. J., "Psilocybin-assisted treatment for alcohol dependence: a proof-of-concept study," J Psychopharmacol, 2015;29(3):289-99.

Carbonaro, T. M.; Eshleman, A. J.; Forster, M. J.; Cheng, K.; Rice, K. C.; Gatch, M. B., "The role of 5-HT2A, 5-HT 2C and mGlu2 receptors in the behavioral effects of tryptamine hallucinogens N,N-dimethyltryptamine and N,N-diisopropyltryptamine in rats and mice," Psychopharmacology (Berl), 2015;232(1):275-84.

Eide, P. K.; Hole, K., "Intrathecal substance P modulates the depressant effect of 5-methoxy-N,N-dimethyltryptamine on a reflex response to radiant heat in mice," Neurosci Lett, 1988;90(1-2):203-7.

Eide, P. K.; Hole, K.; Berge, O. G., "Mechanisms by which the putative serotonin receptor antagonist metitepin alters nociception in mice," J Neural Transm, 1988;73(1):31-41.

Eide, P. K.; Hole, K.; Berge, O. G.; Broch, O. J., "5-HT depletion with 5,7-DHT, PCA and PCPA in mice: differential effects on the sensitivity to 5-MeODMT, 8-OH-DPAT and 5-HTP as measured by two nociceptive tests," Brain Res, 1988;440(1):42-52.

Eide, P. K.; Tjolsen, A., "Effects of serotonin receptor antagonists and agonists on the tail-flick response in mice involve altered tail-skin temperature," Neuropharmacology, 1988;27(9):889-93.

Geyer, M. A.; Tapson, G. S., "Habituation of tactile startle is altered by drugs acting on serotonin-2 receptors," Neuropsychopharmacology, 1988;1(2):135-47.

Glennon, R. A., "Site-selective serotonin agonists as discriminative stimuli," Psychopharmacol Ser, 1988;4:15-31.

Godfrey, P. P.; McClue, S. J.; Young, M. M.; Heal, D. J., "5-Hydroxytryptamine-stimulated inositol phospholipid hydrolysis in the mouse cortex has pharmacological characteristics compatible with mediation via 5-HT2 receptors but this response does not reflect altered 5-HT2 function after 5,7-dihydroxytryptamine lesioning or repeated antidepressant treatments," J Neurochem, 1988;50(3):730-8.

Gyarmati, S.; Timar, J.; Knoll, B.; Knoll, J., "Serotonin-mediated behavior in rats chronically treated with (−) deprenyl," Pol J Pharmacol Pharm, 1988;40(6):667-71.

Haleem, D. J.; Kennett, G.; Curzon, G., Adaptation of female rats to stress: shift to male pattern by inhibition of corticosterone synthesis, Brain Res, 1988;458(2):339-47.

Heal, D. J.; Smith, S. L., "The effects of acute and repeated administration of T3 to mice on 5-HT1 and 5-HT2 function in the brain and its influence on the actions of repeated electroconvulsive shock," Neuropharmacology, 1988;27(12):1239-48.

Lima, L.; Ayala, C.; Walder, R.; Drujan, B., "Behavioural effects produced in mice infected with venezuelan equine encephalomyelitis virus," Physiol Behav, 1988;43(3):281-6.

Lyon, R. A.; Titeler, M.; Seggel, M. R.; Glennon, R. A., "Indolealkylamine analogs share 5-HT2 binding characteristics with phenylalkylamine hallucinogens," Eur J Pharmacol, 1988;145(3):291-7.

Minor, B. G.; Persson, M. L.; Post, C.; Jonsson, G.; Archer, T., "Intrathecal noradrenaline restores 5-methoxy-N,N-dimethyltryptamine induced antinociception abolished by intrathecal 6-hydroxydopamine," J Neural Transm, 1988;72(2):107-20.

Moser, P. C.; Redfern, P. H., "The effect of benzodiazepines on the 5-HT agonist-induced head-twitch response in mice," Eur J Pharmacol, 1988;151(2):223-31.

Murakami, H.; Sano, M.; Tsukimura, T.; Yamazaki, A., The relaxation induced by indole and nonindole 5-HT agonists in the molluscan smooth muscle, Comp Biochem Physiol C, 1988;90(1):249-55.

Mushiake, H.; Kodama, T.; Shima, K.; Yamamoto, M.; Nakahama, H., "Fluctuations in spontaneous discharge of hippocampal theta cells during sleep-waking states and PCPA-induced insomnia," J Neurophysiol, 1988;60(3):925-39.

Nagano, N.; Ono, H.; Fukuda, H., "Functional significance of subtypes of 5-HT receptors in the rat spinal reflex pathway," Gen Pharmacol, 1988;19(6):789-93.

Nagano, N.; Ono, H.; Ozawa, M.; Fukuda, H., "The spinal reflex of chronic spinal rats is supersensitive to 5-HTP but not to TRH or 5-HT agonists," Eur J Pharmacol, 1988;149(3):337-44.

Peters, D. A., "Both prenatal and postnatal factors contribute to the effects of maternal stress on offspring behavior and central 5-hydroxytryptamine receptors in the rat," Pharmacol Biochem Behav, 1988;30(3):669-73.

Peters, D. A., "Effects of maternal stress during different gestational periods on the serotonergic system in adult rat offspring," Pharmacol Biochem Behav, 1988;31(4):839-43.

Simansky, K. J.; Schechter, L. E., "Properties of some 1-arylpiperazines as antagonists of stereotyped behaviors mediated by central serotonergic receptors in rodents," J Pharmacol Exp Ther, 1988;247(3):1073-81.

Wilkinson, L. O.; Jacobs, B. L., "Lack of response of serotonergic neurons in the dorsal raphe nucleus of freely moving cats to stressful stimuli," Exp Neurol, 1988;101(3):445-57.

Winter, J. C.; Rabin, R. A., "Interactions between serotonergic agonists and antagonists in rats trained with LSD as a discriminative stimulus," Pharmacol Biochem Behav, 1988;30(3):617-24.

Arnt, J., "Characterization of the discriminative stimulus properties induced by 5-HT1 and 5-HT2 agonists in rats," Pharmacol Toxicol, 1989;64(2):165-72.

Berendsen, H. H.; Jenck, F.; Broekkamp, C. L., "Selective activation of 5HT1A receptors induces lower lip retraction in the rat," Pharmacol Biochem Behav, 1989;33(4):821-7.

Dubocovich, M. L.; Shankar, G.; Mickel, M., "2-[125I]iodomelatonin labels sites with identical pharmacological characteristics in chicken brain and chicken retina," Eur J Pharmacol, 1989;162(2):289-99.

Eide, P. K.; Hole, K., "Subsensitivity of serotonin and substance P receptors involved in nociception after repeated administration of a serotonin receptor agonist," J Neural Transm, 1989;77(1):1-10.

Fowler, C. J.; Thorell, G.; Fagervall, I., "Postmortem- and cryostability of the potassium-evoked release of [3H]5-hydroxytryptamine from rat cerebral cortical miniprisms," J Neural Transm, 1989;75(2):135-48.

(56) References Cited

OTHER PUBLICATIONS

Freedman, J.; Hokfelt, T.; Post, C.; Brodin, E.; Sundstrom, E.; Jonsson, G.; Terenius, L.; Leander, S.; Fischer, J. A.; Verhofstad, A., "Immunohistochemical and behavioral analysis of spinal lesions induced by a substance P antagonist and protection by thyrotropin releasing hormone," Exp Brain Res, 1989;74(2):279-92.
Heidenreich, B. A.; Rebec, G. V., "Serotonergic dorsal raphe neurons: changes in spontaneous neuronal activity and responsiveness to 5-MeODMT following long-term amphetamine administration," Neurosci Lett, 1989;103(1):81-6.
Hide, I.; Kato, T.; Yamawaki, S., "In vivo determination of 5-hydroxytryptamine receptor-stimulated phosphoinositide turnover in rat brain," J Neurochem, 1989;53(2):556-60.
Hoyer, D.; Waeber, C.; Schoeffter, P.; Palacios, J. M.; Dravid, A., "5-HTIC receptor-mediated stimulation of inositol phosphate production in pig choroid plexus. A pharmacological characterization," Naunyn Schmiedebergs Arch Pharmacol, 1989;339(3):252-8.
Jackson, H. C.; Kitchen, I., "Behavioural profiles of putative 5-hydroxytryptamine receptor agonists and antagonists in developing rats," Neuropharmacology, 1989;28(6):635-42.
Kodama, T.; Mushiake, H.; Shima, K.; Hayashi, T.; Yamamoto, M., "Slow fluctuations of single unit activities of hippocampal and thalamic neurons in cats. II. Role of serotonin on the stability of neuronal activities," Brain Res, 1989;487(1):35-44.
Kubota, M.; Ueno, K.; Yamano, M.; Kitagawa, H., "[Changes in 5-HT2 receptor density induced by repeated treatment with 5-HT uptake inhibitor or 5-HT agonist]," Yakubutsu Seishin Kodo, 1989;9(3):289-92.
Maj, J.; Deren, A.; Moryl, E., "Pharmacological effects of oxaprotiline enantiomers on the central serotonin system," Pol J Pharmacol Pharm, 1989;41(4):345-57.
Marek, G. J.; Li, A. A.; Seiden, L. S., "Evidence for involvement of 5-hydroxytryptamine1 receptors in antidepressant-like drug effects on differential-reinforcement-of-low-rate 72-second behavior," J Pharmacol Exp Ther, 1989;250(1):60-71.
McClue, S. J.; Brazell, C.; Stahl, S. M., "Hallucinogenic drugs are partial agonists of the human platelet shape change response: A physiological model of the 5-HT2 receptor," Biological Psychiatry, 1989;26(3):297-302.
McKenna, D. J.; Peroutka, S. J., "Differentiation of 5-hydroxytryptamine2 receptor subtypes using 125I-R-(−)2,5-dimethoxy-4-iodo-phenylisopropylamine and 3H-ketanserin," J Neurosci, 1989;9(10):3482-90.
Nabeshima, T.; Itoh, K.; Kawashima, K.; Kameyama, T., "Effects of 5-HT2 receptor antagonist on cycloheximide-induced amnesia in mice," Pharmacol Biochem Behav, 1989;32(3):787-90.
Nabeshima, T.; Tohyama, K.; Noda, A.; Maeda, Y.; Hiramatsu, M.; Harrer, S. M.; Kameyama, T.; Furukawa, H.; Jacobson, A. E.; Rice, K. C., "Effects of metaphit on phencyclidine and serotonin2 receptors," Neurosci Lett, 1989;102(2-3):303-8.
Nanry, K. P.; Tilson, H. A., "The role of 5HT1A receptors in the modulation of the acoustic startle reflex in rats," Psychopharmacology (Berl), 1989;97(4):507-13.
Nash, J. F.; Meltzer, H. Y., "Effect of gepirone and ipsapirone on the stimulated and unstimulated secretion of prolactin in the rat," J Pharmacol Exp Ther, 1989;249(1):236-41.
Ohi, K.; Mikuni, M.; Takahashi, K., "Stress adaptation and hypersensitivity in 5-HT neuronal systems after repeated foot shock," Pharmacol Biochem Behav, 1989;34(3):603-8.
Pranzatelli, M. R., "Benzodiazepine-induced shaking behavior in the rat: structure-activity and relation to serotonin and benzodiazepine receptors," Exp Neurol, 1989;104(3):241-50.
Sadzot, B.; Baraban, J. M.; Glennon, R. A.; Lyon, R. A.; Leonhardt, S.; Jan, C. R.; Titeler, M., "Hallucinogenic drug interactions at human brain 5-HT2 receptors: implications for treating LSD-induced hallucinogenesis," Psychopharmacology (Berl), 1989;98(4):495-9.
Sargent, T., 3rd; Braun, U.; Braun, G.; Kusubov, N.; Bristol, K. S., "Cerebral and peripheral demethylation of psychotomimetics measured by expired 14CO2," Int J Rad Appl Instrum B, 1989;16(1):91-9.
Sheets, L. P.; Cook, L. L.; Reiter, L. W., "Serotonergic modulation of the acoustic startle response in rats during preweaning development," Pharmacol Biochem Behav, 1989;33(2):415-22.
Stewart, B. R.; Jenner, P.; Marsden, C. D., "Induction of purposeless chewing behaviour in rats by 5-HT agonist drugs," Eur J Pharmacol, 1989;162(1):101-7.
Wieland, S.; Goodale, D.; Lucki, I., "Behavioral effects of 8-OH-DPAT: studies using the Microtaxic ventricular injector," J Neurosci Methods, 1989;30(2):151-9.
Barbeau, H.; Rossignol, S., "The effects of serotonergic drugs on the locomotor pattern and on cutaneous reflexes of the adult chronic spinal cat," Brain Res, 1990;514(1):55-67.
Bourke, C. A.; Carrigan, M. J.; Dixon, R. J., "The pathogenesis of the nervous syndrome of Phalaris aquatica toxicity in sheep," Aust Vet J, 1990;67(10):356-8.
Cancela, L.; Volosin, M.; Molina, V. A., "Opioid involvement in the adaptive change of 5-HTI receptors induced by chronic restraint," Eur J Pharmacol, 1990;176(3):313-9.
Darmani, N. A.; Martin, B. R.; Pandey, U.; Glennon, R. A., "Do functional relationships exist between 5-HT1A and 5-HT2 receptors?" Pharmacol Biochem Behav, 1990;36(4):901-6.
Eide, P. K.; Joly, N. M.; Hole, K., "The role of spinal cord 5-HT1A and 5-HT1B receptors in the modulation of a spinal nociceptive reflex," Brain Res, 1990;536(1-2):195-200.
Office Action issued in MX/a/2021/009941 (WO2020/169850), dated Oct. 23, 2024, translation.
Third Party Submission filed in U.S. Appl. No. 18/373,906, dated Oct. 3, 2024.
Euvrard, C. et al., "Effect of quipazine, a serotonin-like drug, on striatal cholinergic interneurons," Eur J Pharmacol, 1977;41(3):281-9.
Uthaug et al., A single inhalation of vapor from dried toad secretion containing 5-methoxy-N, N-dimethyltryptamine (5-MeO-DMT) in a naturalistic setting is related to sustained enhancement of satisfaction with life, mindfulness-related capacities and a decrement of psychopathological symptoms, Psychopharmacology (2019) 236:2653-2666 https://doi.org/10.1007/s00213-019-05236-w.
A. Bonham, Neurotransmitters in the CNS control of breathing, Respiration physiology, 1995, 101(3):219-230.
Ramaekers et al., Benefits and Challenges of Ultra-Fast, Short-Acting Psychedelics in the Treatment of Depression, Am J Psychiatry, 2025, 182 (1): 33-46, doi: 10.1176/appi.ajp.20230890.
Ghaznavi et al., Primum Non Nocere: The Onus to Characterize the Potential Harms of Psychedelic Treatment, Am J Psychiatry, 2025, 182 (1): 47-53, doi: 10.1176/appi.ajp.20230914.
Liao et al., Structural neural plasticity evoked by rapid-acting antidepressant interventions, Nat Rev Neurosci, 2024, doi: 10.1038/s41583-024-00876-0.
Shinozuka et al., Synergistic, multi-level understanding of psychedelics: three systematic reviews and meta-analyses of their pharmacology, neuroimaging and phenomenology, Transl Psychiatry, 2024, 14(1): 485, doi: 10.1038/s41398-024-03187-1.
Erritzoe et al., Effects of discontinuation of serotonergie antidepressants prior to psilocybin therapy versus escitalopram for major depression, J Psychopharmacol, 2024, 38(5):458-470, doi:10.1177/02698811241237870.
Kwasny et al., Short-term safety and tolerability profile of 5-methoxy-N,N-dimethyltryptamine in human subjects: a systematic review of clinical trials, Front Psychiatry, 2024, 15: 1477996, doi: 10.3389/fpsyt.2024.1477996.
Roberts et al., Rapid antidepressant effect of intranasal BPL-003 (5-methoxy-N,N-dimethyltryptamine) in treatment-resistant patients: a Phase 2a open-label study, 2024.
Colloca et al., What should constitute a control condition in psychedelic drug trials?, Nature Mental Health, 2024.
A Study to Evaluate Safety and Efficacy of SAGE-547 in Participants With Moderate Postpartum Depression (547-PPD-202C),

(56) References Cited

OTHER PUBLICATIONS

Clinicaltrials.gov, Retrieved Jan. 28, 2022. URL: www.clinicaltrials.gov/study/NCT02942017?cond=post%20partum%20depression&termsage&rank2.
Hutcherson, Brexanolone for postpartum depression, American Journal of HealthSystem Pharmacy, 2020, vol. 77, issue 5, pp. 336-345.
Kanes, Brexanolone (SAGE-547 injection) in post-partum depression: a randomised controlled trial, Lancet, 2017, vol. 390, pp. 480-489.
Trevethan, The Barkin Index of Maternal Functioning: an evaluation and foundations for a new parental functioning scale, Health Services and Outcomes Research Methodology, 2022, vol. 22, pp. 416-434.
Barkin, The Psychometric Properties of the Barkin Index of Maternal Functioning, Journal of Obstetric, Gynecologic & Neonatal Nursing 2014, vol. 43, issue 6, pp. 792-802.
Chamgurdani, The effect of counseling with a skills training approach on maternal functioning: a randomized controlled clinical trial, BMC Women's Health, 2019, vol. 20, issue 51.
Suryawanshi, A Comprehensive Review on Postpartum Depression, Cureus, 2022, vol. 14, issue 12, p. e32745.
Shang, The effectiveness of postpartum interventions aimed at improving women's mental health after medical complications of pregnancy: a systematic review and meta-analysis, BMC Pregnancy and Childbirth, 2022, vol. 22, p. 809.
Dorheim, Sleep and Depression in Postpartum Women: A Population-Based Study, Sleep, 2009, vol. 32, issue 7, pp. 847-855.
Brand, Psychedelics and Breastfeeding: What We Know- and Don't Know—About a Taboo Subject, Double Blind, retrieved Sep. 15, 2022. URL: https://doubleblindmag.com/psychedelics -and-breastfeeding/.
GH Research PLC, GH Research Announces Successful Outcome of the Phase 2 part of its Phase ½ Clinical Trial of GH001 in Treatment-Resistant Depression, GlobeNewswire, Retrieved Dec. 6, 2021. URL: www.globenewswire.com/en/news-release/2021/12/06/2346425/0/en/GHResearch-Announces-SuccessfulOutcome-of-the-Phase-2-part-of-itsPhase-1-2-Clinical-Trial-of-GH001-inTreatment-Resistant-Depression.html.
Nelson, Ethical Considerations in the Design and Conduct of Clinical Lactation Studies, U.S. Food and Drug Administration (FDA), retrieved from Web Archives, May 16, 2022. URL: https://web.archive.org/web/20220516053433/https://www.fda.gov/files/drugs/published/Nelson--Ethical-Considerations-in-the-Design-and-Conduct-of-Clinical-Lactation-Studies.pdf.
"Protocol 547-PPD-202, a Multicenter, Randomized, Double-Blind, Parallel-Group, Placebo Controlled Study Evaluating the Efficacy, Safety, and Pharmacokinetics of SAGE-547 Injection in the Treatment of Adult Female Subjects With Severe Postpartum Depression and Adult Female Subjects With Moderate Postpartum Depression," Retrieved Mar. 16, 2017. URL: https://cdn.clinicaltrials.gov/large-docs/17/NCT02942017/Prot_000.pdf.
How Much and How Often to Breastfeed, CDC, retrieved Apr. 11, 2022, URL: www.cdc.gov/infant-toddler-nutrition/breastfeeding/how-much-and-how-often.html.
Office Action issued in CL2022-02303 (WO2021/170614), dated Dec. 9, 2024, translation.
Third Party Submission filed in U.S. Appl. No. 18/373,914, dated Oct. 4, 2024.
Third Party Submission filed in U.S. Appl. No. 18/373,904, dated Oct. 1, 2024.
Gerbasi, "Associations between commonly used patient-reported outcome tools in postpartum depression clinical practice and the Hamilton Rating Scale for Depression," Archives of Women's Mental Health, 2020, 23: 727-735.
Walker, The Long-Term Impact of Maternal Anxiety and Depression Postpartum and in Early Childhood on Child and Paternal Mental Health at 11-12 Years Follow-Up, Frontier in Psychiatry, 2020, 1: 562237.
Gillin JCT, J; Stoff, D M; Stillman, R; Shortlidge, J S ; Wyatt, R J. "5-Methoxy-N,N-dimethyltryptamine: behavioral and toxicological effects in animals." Biol Psychiatry. 1976.
Gomes MM, Coimbra JB, Clara RO, Dorr FA, Moreno AC, Chagas JR, Tufik S, Pinto E, Jr., Catalani LH, Campa A., "Biosynthesis of N,N-dimethyltryptamine (DMT) in a melanoma cell line and its metabolization by peroxidases." Biochem Pharmacol. 2014;88(3):393-401.
Goodwin GM, De Souza RJ, Wood AJ, Green AR., "The enhancement by lithium of the 5-HT1A mediated serotonin syndrome produced by 8-OH-DPAT in the rat: evidence for a post-synaptic mechanism." Psychopharmacology (Berl). 1986;90(4):488-493.
Goodwin GM, Green AR., "A behavioural and biochemical study in mice and rats of putative selective agonists and antagonists for 5-HT1 and 5-HT2 receptors." Br J Pharmacol. 1985;84(3):743-753.
Gouzoulis-Mayfrank E, Heekeren K, Neukirch A, Stoll M, Stock C, Obradovic M, Kovar KA. "Psychological effects of (S)-ketamine and N,N-dimethyltryptamine (DMT): a double-blind, cross-over study in healthy volunteers." Pharmacopsychiatry. 2005;38(6):301-311.
Gouzoulis-Mayfrank E, Thelen B, Habermeyer E, Kunert HJ, Kovar KA, Lindenblatt H, Hermle L, Spitzer M, Sass H. "Psychopathological, neuroendocrine and autonomic effects of 3,4-methylenedioxyethylamphetamine (MDE), psilocybin and d-methamphetamine in healthy volunteers. Results of an experimental double-blind placebo-controlled study." Psychopharmacology (Berl). 1999;142(1):41-50.
Grahame-Smith DG. "Inhibitory effect of chlorpromazine on the syndrome of hyperactivity produced by L-tryptophan or 5-methoxy-N,N-dimethyltryptamine in rats treated with a monoamine oxidase inhibitor." Br J Pharmacol. 1971;43(4):856-864.
Grahame-Smith DG, Green AR. "The role of brain 5-hydroxytryptamine in the hyperactivity produced in rats by lithium and monoamine oxidase inhibition." Br J Pharmacol. 1974;52(1):19-26.
Green AR. "Repeated chlorpromazine administration increases a behavioural response of rats to 5-hydroxytryptamine receptor stimulation." Br J Pharmacol. 1977;59(2):367-371.
Green AR. "Repeated exposure of rats to the convulsant agent flurothyl enhances 5-hydroxytryptamine- and dopamine-mediated behavioural responses." Br J Pharmacol. 1978;62(3):325-331.
Green AR, DeSouza RJ, Davies EM, Cross AJ. "The effects of Ca2+ antagonists and hydralazine on central 5-hydroxytryptamine biochemistry and function in rats and mice." Br J Pharmacol. 1990;99(1):41-46.
Green AR, Hall JE, Rees AR. "A behavioural and biochemical study in rats of 5-hydroxytryptamine receptor agonists and antagonists, with observations on structure-activity requirements for the agonists." Br J Pharmacol. 1981;73(3):703-719.
Greene SL. "Tryptamines." 2013:363-381.
Griffiths R, Richards W, Johnson M, McCann U, Jesse R. "Mystical-type experiences occasioned by psilocybin mediate the attribution of personal meaning and spiritual significance 14 months later." J Psychopharmacol. 2008;22(6):621-632.
Griffiths RR, Johnson MW, Carducci MA, Umbricht A, Richards WA, Richards BD, Cosimano MP, Klinedinst MA. "Psilocybin produces substantial and sustained decreases in depression and anxiety in patients with life-threatening cancer: A randomized double-blind trial." J Psychopharmacol. 2016;30(12):1181-1197.
Griffiths RR, Johnson MW, Richards WA, Richards BD, Jesse R, MacLean KA, Barrett FS, Cosimano MP, Klinedinst MA. "Psilocybin-occasioned mystical-type experience in combination with meditation and other spiritual practices produces enduring positive changes in psychological functioning and in trait measures of prosocial attitudes and behaviors." J Psychopharmacol. 2018;32(1):49-69.
Griffiths RR, Johnson MW, Richards WA, Richards BD, McCann U, Jesse R. "Psilocybin occasioned mystical-type experiences: immediate and persisting dose-related effects." Psychopharmacology (Berl). 2011;218(4):649-665.
Griffiths RR, Richards WA, McCann U, Jesse R. "Psilocybin can occasion mystical-type experiences having substantial and sustained personal meaning and spiritual significance." Psychopharmacology (Berl). 2006;187(3):268-283; discussion 284-292.

(56) References Cited

OTHER PUBLICATIONS

Grob CS, Danforth AL, Chopra GS, Hagerty M, McKay CR, Halberstadt AL, Greer GR. "Pilot study of psilocybin treatment for anxiety in patients with advanced-stage cancer." Arch Gen Psychiatry. 2011;68(1):71-78.
Grome JJ, Harper AM. "Local cerebral glucose utilisation following indoleamine- and piperazine-containing 5-hydroxytryptamine agonists." J Neurochem. 1986;46(1):117-124.
Guchhait RB. "Biogenesis of 5-methoxy-N,N-dimethyltryptamine in human pineal gland." Journal of Neurochemistry. 1976.
Haijen ECHM, Kaelen M, Roseman L, Timmermann C, Kettner H, Russ S, Nutt D, Daws RE, Hampshire ADG, Lorenz R, Carhart-Harris RL. "Predicting Responses to Psychedelics: A Prospective Study." Frontiers in Pharmacology. 2018;9.
Halberstadt AG, M. "Hallucinogens Review." 2010.
Halberstadt AL. "Behavioral and pharmacokinetic interactions between monoamine oxidase inhibitors and the hallucinogen 5-methoxy-N,N-dimethyltryptamine." Pharmacol Biochem Behav. 2016;143:1-10.
Halberstadt AL, Buell MR, Masten VL, Risbrough VB, Geyer MA. "Modification of the effects of 5-methoxy-N,N-dimethyltryptamine on exploratory behavior in rats by monoamine oxidase inhibitors." Psychopharmacology (Berl). 2008;201(1):55-66.
Halberstadt AL, Geyer MA. "Neuropharmacology of Lysergic Acid Diethylamide (LSD) and Other Hallucinogens." Biological Research on Addiction; 2013:625-635.
Halberstadt AL, Koedood L, Powell SB, Geyer MA. "Differential contributions of serotonin receptors to the behavioral effects of indoleamine hallucinogens in mice." J Psychopharmacol. 2011;25(11):1548-1561.
Halberstadt AL, Nichols DE, Geyer MA. "Behavioral effects of alpha,alpha,beta,beta-tetradeutero-5-MeO-DMT in rats: comparison with 5-MeO-DMT administered in combination with a monoamine oxidase inhibitor." Psychopharmacology (Berl). 2012;221(4):709-718.
Halpern JH, Sherwood, A.R., Passie, T., Blackwell, K.C., & Ruttenber, A.J. "Evidence of health and safety in American members of a religion who use a hallucinogenic sacrament." Medical Science Monitor. 2008.
Halpern JH, Pope HG. "Do hallucinogens cause residual neuropsychological toxicity?" Drug and Alcohol Dependence. 1999;53(3):247-256.
Harrison-Read PE. "Evidence from behavioural reactions to fenfluramine, 5-hydroxytryptophan, and 5-methoxy-N,N-dimethyltryptamine for differential effects of short-term and long-term lithium on indoleaminergic mechanisms in rats [proceedings]." British Journal of Pharmacology. 1979.
Hasler F, Bourquin D, Brenneisen R, Vollenweider FX. "Renal excretion profiles of psilocin following oral administration of psilocybin: a controlled study in man." Journal of Pharmaceutical and Biomedical Analysis. 2002;30(2):331-339.
Hasler F, Grimberg U, Benz MA, Huber T, Vollenweider FX. "Acute psychological and physiological effects of psilocybin in healthy humans: a double-blind, placebo-controlled dose-effect study." Psychopharmacology (Berl). 2004;172(2):145-156.
Hirose T, Uwahodo Y, Yamada S, Miwa T, Kikuchi T, Kitagawa H, Burris KD, Altar CA, Nabeshima T. "Mechanism of action of aripiprazole predicts clinical efficacy and a favourable side-effect profile." J Psychopharmacol. 2004;18(3):375-383.
Ho BT, McIsaac MW, An R, Harris RT, Walker KE, Kralik PM, Airaksinen MM. "Biological activities of some 5-substituted N,N-dimethyltryptamines, alpha-methyltryptamines, and gramines." Psychopharmacologia. 1970;16(5):385-394.
Horita A, Weber LJ. "The enzymic dephosphorylation and oxidation of psilocybin and pscilocin by mammalian tissue homogenates." Biochemical Pharmacology. 1961;7(1):47-54.
Ito T, Furukawa K, Karasawa T, Kadokawa T, Shimizu M. "Functional change in the rat spinal cord by chronic spinal transection and possible roles of monoamine neurons." Jpn J Pharmacol. 1985;38(3):243-251.
J C Gillin JT, D M Stoff, R Stillman, J S Shortlidge, R J Wyatt. 5-Methoxy-N,N-dimethyltryptamine: behavioral and toxicological effects in animals. Biol Psychiatry. 1976.
Jiang XL, Shen HW, Mager DE, Schmidt S, Yu AM. "Development of a mechanism-based pharmacokinetic/pharmacodynamic model to characterize the thermoregulatory effects of serotonergic drugs in mice." Acta Pharm Sin B. 2016;6(5):492-503.
Jiang XL, Shen HW, Mager DE, Yu AM. Pharmacokinetic interactions between monoamine oxidase A inhibitor harmaline and 5-methoxy-N,N-dimethyltryptamine, and the impact of CYP2D6 status. Drug Metab. Dispos. 2013;41(5):975-986.
Jiang XL, Shen HW, Yu AM. Potentiation of 5-methoxy-N,N-dimethyltryptamine-induced hyperthermia by harmaline and the involvement of activation of 5-HT1A and 5-HT2A receptors. Neuropharmacology. 2015;89:342-351.
Jiang XL, Shen HW, Yu AM. Modification of 5-methoxy-N,N-dimethyltryptamine-induced hyperactivity by monoamine oxidase a inhibitor harmaline in mice and the underlying serotonergic mechanisms. Pharmacol Rep. 2016;68(3):608-615.
Johnson M, Richards W, Griffiths R. "Human hallucinogen research: guidelines for safety." J Psychopharmacol. 2008;22(6):603-620.
Johnson MW, Griffiths RR, Hendricks PS, Henningfield JE. "The abuse potential of medical psilocybin according to the 8 factors of the Controlled Substances Act." Neuropharmacology. 2018;142:143-166.
Kaelen M, Giribaldi B, Raine J, Evans L, Timmerman C, Rodriguez N, Roseman L, Feilding A, Nutt D, Carhart-Harris R. "The hidden therapist: evidence for a central role of music in psychedelic therapy." Psychopharmacology (Berl). 2018;235(2):505-519.
Krebs TS, Johansen PO. "Lysergic acid diethylamide (LSD) for alcoholism: meta-analysis of randomized controlled trials." J Psychopharmacol. 2012;26(7):994-1002.
Krebs-Thomson K, Ruiz EM, Masten V, Buell M, Geyer MA. "The roles of 5-HT1A and 5-HT2 receptors in the effects of 5-MeO-DMT on locomotor activity and prepulse inhibition in rats." Psychopharmacology (Berl). 2006;189(3):319-329.
Kuypers KP, Riba J, de la Fuente Revenga M, Barker S, Theunissen EL, Ramaekers JG. "Ayahuasca enhances creative divergent thinking while decreasing conventional convergent thinking." Psychopharmacology (Berl). 2016;233(18):3395-3403.
Kuypers KPC. "Out of the box: A psychedelic model to study the creative mind." Med Hypotheses. 2018;115:13-16.
Kuypers KPC. "Psychedelic medicine: The biology underlying the persisting psychedelic effects." Med Hypotheses. 2019;125:21-24.
Labate BC, Feeney K. "Ayahuasca and the process of regulation in Brazil and internationally: implications and challenges." Int J Drug Policy. 2012;23(2):154-161.
Lafrance A, Loizaga-Velder A, Fletcher J, Renelli M, Files N, Tupper KW. "Nourishing the Spirit: Exploratory Research on Ayahuasca Experiences along the Continuum of Recovery from Eating Disorders." J Psychoactive Drugs. 2017;49(5):427-435.
Lalley PM. "The excitability and rhythm of medullary respiratory neurons in the cat are altered by the serotonin receptor agonist 5-methoxy-N,N, dimethyltryptamine." Brain Research. 1994;648(1):87-98.
Lebedev AV, Kaelen M, Lovden M, Nilsson J, Feilding A, Nutt DJ, Carhart-Harris RL. LSD-induced entropic brain activity predicts subsequent personality change. Hum Brain Mapp. 2016;37(9):3203-3213.
Lebedev AV, Lovden M, Rosenthal G, Feilding A, Nutt DJ, Carhart-Harris RL. "Finding the self by losing the self: Neural correlates of ego-dissolution under psilocybin." Hum Brain Mapp. 2015;36(8):3137-3153.
Lewis CR, Preller KH, Krachenmann R, Michels L, Staempfli P, Vollenweider FX. "Two dose investigation of the 5-HT-agonist psilocybin on relative and global cerebral blood flow." Neuroimage. 2017;159:70-78.
Liester MB, Prickett JI. "Hypotheses regarding the mechanisms of ayahuasca in the treatment of addictions." J Psychoactive Drugs. 2012;44(3):200-208.
Lima da Cruz RV, Moulin TC, Petiz LL, Leão RN. "A Single Dose of 5-MeO-DMT Stimulates Cell Proliferation, Neuronal Survivabil-

(56) References Cited

OTHER PUBLICATIONS ity, Morphological and Functional Changes in Adult Mice Ventral Dentate Gyrus." Frontiers in Molecular Neuroscience. 2018;11(312).
Llado-Pelfort L, Celada P, Riga MS, Troyano-Rodriguez E, Santana N, Artigas F. "Effects of Hallucinogens on Neuronal Activity." Curr Top Behav Neurosci. 2018;36:75-105.
Yu, A. M., "Indolealkylamines: biotransformations and potential drug-drug interactions," *AAPS Journal*, 2008;10(2):242-53.
Zimmerman, M et al., "The remission from depression questionnaire as an outcome measure in the treatment of depression," *Depress and Anxiety*, 2014;31(6):533-8.
Zarracina, J., "The fascinating, strange medical potential of psychedelic drugs, explained in 50+ studies," *Vox*, 2016.
Evarts, E. V., "Some effects of bufotenine and lysergic acid diethylamide on the monkey," *AMA Arch Neurol Psychiatry*, 1956;75(1):49-53.
Taborsky, R. G. et al., "The relationship between the metabolic fate and pharmacological action of 5-methoxy-N-methyltryptamine," *Biochemical Pharmacology*, 1964;13(3):531-534.
Ghosal, S et al., "Occurrence of 5-methoxy-N,N-dimethyltryptamine oxide and other tryptamines in Desmodium pulchellum Benth ex Baker," *Chem Ind*, 1965;19:793-4.
Taborsky, R. G. et al., "6-hydroxylation: effect on the psychotropic potency of tryptamines," *Science*, 1966;153(3739):1018-20.
Erspamer, V. et al., "5-Methoxy- and 5-Hydroxyindoles in the skin of Bufo alvarius," *Biochemical Pharmacology*, 1967;16(7):1149-1164.
Gessner, P. K. et al., "Structure-activity relationships among 5-methoxy-n:n-dimethyltryptamine, 4-hydroxy-n:n-dimethyltryptamine (psilocin) and other substituted tryptamines," *Life Sci*, 1968;7(5):267-77.
Gessner, P. K., "Pharmacological Studies of 5-Methoxy-N,N-Dimethyltryptamine, LSD and Other Hallucinogens," Psychotomimetic drugs, 1969:105-122.
Hopf, A. et al. "Autoradiographic Studies on the Distribution of Psychoactive Drugs in the Rat Brain," *Psychopharmacologia*, 1969; 16, 201-222.
Horowitz, M. J., "Flashbacks: recurrent intrusive images after the use of LSD," *Amer. J. Psychiatry*, 1969;126(4):565-9.
Narasimhachari, N. et al. "The use of o-phthalaldehyde as a spray reagent for the thin-layer chromatographic identification and quantitation of bufotenin and 5-methoxy-N:N-dimethyltryptamine," *J Chromatogr*, 1971; 57(3):433-7.
Strahilevitz, M. et al. "Blocking of 5-methoxy-n-dimethyltryptamine-induced EEG alerting in the rabbit by previous administration of antiserum to this compound," *Biological Psychiatry*, 1971;3(3):227-36.
Winocur, G. et al. "Effects of bufotenine and p-chlorophenylalanine on stress induced behaviour," *Psychopharmacologia*, 1971;22(1):100-10.
Grahame-Smith, D. G. et al., "The prevention by inhibitors of brain proptein synthesis of the hyperactivity and hyperpyrexia produced in rats by monoamine oxidase inhibition and the administration of L-tryptophan or 5-methoxy-N,N-dimethyltryptamine," *Journal of Neurochemistry*, 1972;19(10):2409-22.
Narasimhachari, N. et al., "The determination of bufotenin in urine of schizophrenic patients and normal controls," Journal of *Psychiatric Research*, 1972;9(2):113-121.
Baumann, P. et al., "Identification of N,N-dimethyltryptamine, 5-methoxy-N,N-dimethyltryptamine and bufotenin by cellulose TLC," *Journal of Chromatography*, 1973;86(1):269-73.
Haertzen, C. A., "An Overview of Addiction Research Center Inventory Scales (ARCI): An Appendix and Manual of Scales," National Institute on Drug Abuse, 1974.
Kaplan, J. et al., "Blood and urine levels of N, N-dimethyltryptamine following administration of psychoactive dosages to human subjects," *Psychopharmacologia*, 1974;38(3):239-245.
Carpenter, W. T., Jr., et al., "A test of the transmethylation hypothesis in acute schizophrenic patients," *Am J Psychiatry*, 1975;132(10):1067-71.
Geyer, M. A. et al., "Opposite effects of intraventricular serotonin and bufotenin on rat startle responses," *Pharmacology Biochemistry and Behavior*, 1975;3(4):687-691.
Squires, R. F., "Evidence that 5-methoxy-N, N-dimethyl tryptamine is a specific substrate for MAO-A in the rat: implications for the indoleamine dependent behavioural syndrome," *J Neurochem*, 1975;24(1):47-50.
Von Hungen, K. et al., "Interactions between lysergic acid diethylamide and dopamine-sensitive adenylate cyclase systems in rat brain," *Brain Research*, 1975;94(1):57-66.
Gillin, J. C. et al. ,"Evidence for and against the involvement of N,N-dimethyl-tryptamine (DMT) and 5-methoxy-N,N-dimethyltryptamine (5-MeO-DMT) in schizophrenia," *Psychopharmacol Bull*, 1976;12(4):12-3.
Green, A. R. et al., "Elevation of brain GABA concentrations with amino-oxyacetic acid; effect on the hyperactivity syndrome produced by increased 5-hydroxytryptamine synthesis in rats," *J Neural Transm*, 1976;39(1-2):103-12.
Hamon, M. et al., "The effects of quipazine on 5-HT metabolism in the rat brain," *Naunyn Schmiedebergs Arch Pharmacol*, 1976;294(1):99-108.
Trulson, M. E. et al., "Behavioral evidence for supersensitivity following destruction of central serotonergic nerve terminals by 5,7-dihydroxytryptamine," *J Pharmacol Exp Ther*, 1976;198(1):23-32.
Trulson, M. E et al., "Behavioral evidence for the rapid release of CNS serotonin by PCA and fenfluramine," *Eur J Pharmacol*, 1976;36(1):149-54.
Cottrell, A. C. et al., "A bufotenin-like substance in the urine of schizophrenics," *Am J Psychiatry*, 1977;134(3):322-2.
Schlemmer, R. F., Jr. et al., "The effect of a hallucinogen, 5-methoxy N,N-dimethyltryptamine, on primate social behavior," *Commun Psychopharmacol*, 1977;1(2):105-18.
Glennon, R. A. et al., "Serotonin receptor binding affinities of several hallucinogenic phenylalkylamine and N,N-dimethyltryptamine analogues," *J Med Chem*, 1978;21(8):822-5.
Meltzer, H. Y. et al., "Stimulation of rat prolactin secretion by indolealkylamine hallucinogens," *Psychopharmacology* (*Berl*), 1978;56(3):255-9.
Riceberg, L. J. et al., "Determination of N,N-dimethylindolealkylamines in plasma, blood and urine extracts by radioimmunoassay and high pressure liquid chromatography," *J Pharmacol Exp Ther*, 1978;206(1):158-66.
Sloviter, R. S. et al., "Specificity of a rat behavioral model for serotonin receptor activation," *J Pharmacol Exp Ther*, 1978;206(2):339-47.
Uebelhack, R. et al., "Action of LSD and 5-methoxy-N,N-dimethyltryptamine on the high affinity uptake of [3H]-serotonin by isolated rat brain synaptosomes," *Acta Biol Med Ger*, 1978;37(10):1611-4.
Uebelhack, R. et al., "[Effects of serotonin, 5-hydroxy-N,N-dimethyltryptamine and 5-methoxy-N,N-dimethyltryptamine on the synaptosomal Mg(Na,K)-ATPase from rat brain]," *Acta Biol Med Ger*, 1978;37(2):363-6.
Walters, J. K. et al., "Effects of N,N-dimethyltryptamine (DMT) and 5-methoxy-N,N-dimethyltryptamine (5-MeODMT) on shock elicited fighting in rats," *Pharmacol Biochem Behav*, 1978;9(1):87-90.
Abramson, H. A. et al., "The intracranial injection of drug in goldfish. I: Hallucinogens and their antagonism to smooth muscle activity," *J Asthma Res*, 1979;16(2):55-61.
Glennon, R. A. et al., "Bufotenine esters," *J Med Chem*, 1979;22(11):1414-6.
Glennon, R. A. et al., "Hallucinogens as a discriminative stimuli: Generalization of DOM to a 5-methoxy-N, N-dimethyltryptamine stimulus," *Life Sciences*, 1979;24(11):993-997.
Nicolaou, N. M. et al., "Interactions between serotonergic and dopaminergic systems in rat brain demonstrated by small unilateral lesions of the raphe nuclei," *Eur J Pharmacol*, 1979;57(4):295-305.
Yamada, K. et al., "Serotonergic function in mouse head twitches induced by lithium and reserpine," *Psychopharmacology* (*Berl*), 1979;61(3):255-60.

(56) References Cited

OTHER PUBLICATIONS

Berge, O. G. et al., "Nociception is enhanced after low doses and reduced after high doses of the serotonin receptor agonist 5-methoxy-N,N-dimethyltryptamine," *Neurosci Lett*, 1980;19(2):219-23.
Blackburn, T. P. et al., "Unilateral 5,7-dihydroxytryptamine lesions of the dorsal raphe nucleus (DRN) and rat rotational behaviour," *Eur J Pharmacol*, 1980;67(4):427-38.
Davis, M. et al., "5-Methoxy-N,N-dimethyltryptamine: spinal cord and brainstem mediation of excitatory effects on acoustic startle," *Psychopharmacology* (*Berl*), 1980;70(2):123-30.
Glennon, R. A. et al., "Demethyl analogues of psychoactive methoxyphenalkylamines: synthesis and serotonin receptor affinities," *J Med Chem*, 1980;23(9):990-4.
Glennon, R. A. et al, "Hallucinogenic agents as discriminative stimuli: a correlation with serotonin receptor affinities," *Psychopharmacology* (*Berl*), 1980;68(2):155-8.
Kitzrow, W. et al., "Extraction of serotonin, bufotenin, 5-methoxytryptamine and 5-methoxy-N,N-dimethyltryptamine and their fluorometric determination with o-phthaldialdehyde," *Acta Biol Med Ger*, 1980;39(4):489-94.
Lundberg, D. B. "An evaluation of the mechanism by which serotonergic activation depresses respiration," *J Pharmacol Exp Ther*, 1980;212(3):397-404.
Mueller, R. A. et al., "Evidence that respiratory depression by serotonin agonists may be exerted in the central nervous system," *Pharmacol Biochem Behav*, 1980;13(2):247-55.
Oppenheim, B. et al., "Serotonin receptor site in human platelets from control and chlorpromazine treated subjects," *Prog Biochem Pharmacol*, 1980;16:119-32.
Slater, P. "Circling produced by serotonin and dopamine agonists in raphe lesioned rats: a serotonin model," *Pharmacol Biochem Behav*, 1980;13(6):817-21.
Chapin, R. E. et al., "Antagonism of ethanol-induced decrease in LH by para-chlorophenylalanine: lack of correlation with altered serotonergic mechanisms," *Pharmacol Biochem Behav*, 1981;14(3):293-8.
Schmeer et al., "Further characterization of 5-HT1A receptors in the goldfish retina: role of cyclic AMP in the regulation of the in vitro outgrowth of retinal explants", Neurochem Res,2001;26(3):213-23.
"Is it possible to use Bufo Alvarius with the Volcano?", Aazbeltran, Jan. 8, 2020, URL:https:/www.reddit.com/r/5MeODMT/comments/elvrpt/is_it_possible_to_us_bufo_alvarius_with_the/.
Gotti92: Volcano?; URL:https://www.reddit.com/r/5MeODMT/comments//ebxb1h/volcano/, Dec. 17, 2019.
Uthaug et al., A single inhalation of vapor from dried toad secretion containing 5-methoxy-N, N-dimethyltryptamine (5-MeO-DMT) in a naturalistic setting is related to sustained enhancement of satisfaction with life, mindfulness-related capacities and a decrement of psychopathological symptoms.
IPRP issued in WIPO Patent Application No. PCT/EP2020/067113, Dec. 21, 2021.
Fernanda Palhano-Fontes et al., A randomized placebo-controlled trial on the antidepressant effects of the psychedelic ayahuasca in treatment-resistant depression, Psychological Medicine, Jun. 15, 2018, pp. 655-663.
Integrating with Depression, https://forums.5meodmt.org, retrieved May 24, 2023.
Reddit, Testosterone for depression and anxiety, https://www.reddit.com/r/depressionregimens, Nov. 14, 2019, retrieved May 24, 2023.
Masanori Somei et al: "The Chemistry of Indoles. C1 11. Simple Syntheses of Serotonin, N-Methylserotonin, Bufotenine, 5-Methoxy-N-methyltryptamine, Bufobutanoic Acid, N-( Indol-3-yl) methyl-5-methoxy-N-methyltryptamine, and Lespedamine Based on 1-Hydroxyindole Chemistry.", Chemical & Pharmaceutical Bulletin, vol. 49, No. 1, Jan. 2001 (Jan. 2001), pp. 87-96, XPO55202219, ISSN: 0009-2363, DOI: 10.1248/ cpb.49.87 p. 92—right-hand column, paragraph 3.
Toshio Hoshino et al: "Uber Die Synthese Des Bufotenin-Methyl-Athers (5-Methoxy-N-Dimethyl-Tryptamin) Und Bufotenins ( Synthesen in Der Indol-Gruppe. XV)", Bulletin of the Chemical Society of Japan, vol. 11, No. 3, Mar. 1936 (Mar. 1936), pp. 221-224, XP055641802, JP ISSN: 0009-2673, DOI: 10.1246/bcsj.11.221 cited in the application p. 223, paragraph 4.
S. F. Muthukumaraswamy, A. et al., Blinding and Expectancy Confounds in Psychedelic Randomised Controlled Trials, Expert Rev Clin Pharmacol, 2021.
M. J. Spriggs et al., Body mass index (BMI) does not predict responses to psilocybin, J Psychopharmacol, 2023, vol. 37(1): 107-116, doi: 10.1177/02698811221131994.
M. B. Youdim et al., Brain Iron and Dopamine Receptor Function, Advances in biochemical psychopharmacology, 1983, vol. 37:309-321.
D. S. Stenbaek et al., Brain serotonin 2A receptor binding predicts subjective temporal and mystical effects of psilocybin in healthy humans, J Psychopharmacol, 2021, vol. 35(4): 459-468, doi: 10.1177/0269881120959609.
D. Jancke et al., Bridging the gap between single receptor type activity and whole-brain dynamics, FEBS J, 2022, vol. 289(8): 2067-2084, doi: 10.1111/febs.15855.
M. Horák et al., Bufo alvarius: evidencias literarias y controversias en torno a su uso tradicional, Medicina naturista, 2019, vol. 13(1).
R. L. Carhart-Harris et al., "Can pragmatic research, real-world data and digital technologies aid the development of psychedelic medicine?" J Psychopharmacol, 2022, vol. 36(1): 6-11, doi: 10.1177/02698811211008567.
G. Ona et al., "Can psychedelics be the treatment for the crisis in psychopharmacology?" International Center for Ethnobotanical Education Research & Service, 2019, doi: 10.20944/preprints201901.0249.v1.
M. I. Banks et al., Catalysts for change: the cellular neurobiology of psychedelics, Mol Biol Cell, 2021, vol. 32(12): 1135-1144, doi: 10.1091/mbc.E20-05-0340.
S. G. D. Ruffell et al., Ceremonial Ayahuasca in Amazonian Retreats—Mental Health and Epigenetic Outcomes From a Six-Month Naturalistic Study, Front Psychiatry, 2021, vol. 12, doi: 10.3389/fpsyt.2021.687615.
A. Garcia-Romeu et al., Cessation and reduction in alcohol consumption and misuse after psychedelic use, J Psychopharmacol, 2019, vol. 33(9): 1088-1101, doi: 10.1177/0269881119845793.
K. H. Preller et al., Changes in global and thalamic brain connectivity in LSD-induced altered states of consciousness are attributable to the 5-HT2A receptor, Elife, 2018, vol. 7, doi: 10.7554/eLife.35082.
B. J. Malcolm et al., Changes in Withdrawal and Craving Scores in Participants Undergoing Opioid Detoxification Utilizing Ibogaine, J Psychoactive Drugs, 2018, vol. 50(3): 256-265, doi: 10.1080/02791072.2018.1447175.
L. Lima et al., Characterization of serotonin transporter in goldfish retina by the binding of [3H]paroxetine and the uptake of [3H]serotonin: modulation by light, J Neurochem, 1994, vol. 62(2): 528-35, doi: 10.1046/j.1471-4159.1994.62020528.x.
H. Kaasik et al., Chemical Composition of Traditional and Analog Ayahuasca, J Psychoactive Drugs, 2021, vol. 53(1): 65-75, doi: 10.1080/02791072.2020.1815911.
J. P. Castellanos et al., Chronic pain and psychedelics: a review and proposed mechanism of action, Reg Anesth Pain Med, 2020, vol. 45(7): 486-494, doi: 10.1136/rapm-2020-101273.
L. P. Cameron et al., Chronic, Intermittent Microdoses of the Psychedelic N,N-Dimethyltryptamine (DMT) Produce Positive Effects on Mood and Anxiety in Rodents, ACS Chem Neurosci, 2019, vol. 10(7): 3261-3270, doi: 10.1021/acschemneuro.8b00692.
L. Servillo et al., Citrus genus plants contain N-methylated tryptamine derivatives and their 5-hydroxylated forms, J Agric Food Chem, 2013, vol. 61(21): 5156-62, doi: 10.1021/jf401448q.
S. M. Nayak et al., Classic Psychedelic Coadministration with Lithium, but Not Lamotrigine, is Associated with Seizures: An Analysis of Online Psychedelic Experience Reports, Pharmacopsychiatry, 2021, vol. 54(5): 240-245, doi: 10.1055/a-1524-2794.
C. D. Nichols et al., Classic psychedelics as therapeutics for psychiatric disorders, Handbook of the Behavioral Neurobiology of Serotonin, 2020, pp. 959-966, doi: 10.1016/b978-0-444-64125-0.00049-9.

(56) References Cited

OTHER PUBLICATIONS

N. L. Galvao-Coelho et al., Classic serotonergic psychedelics for mood and depressive symptoms: a meta-analysis of mood disorder patients and healthy participants, Psychopharmacology (Berl), 2021, vol. 238(2): 341-354, doi: 10.1007/s00213-020-05719-1.
S. Muttoni et al., Classical psychedelics for the treatment of depression and anxiety: A systematic review, J Affect Disord, 2019, vol. 258: 11-24, doi: 10.1016/j.jad.2019.07.076.
B. Romeo et al., Clinical and biological predictors of psychedelic response in the treatment of psychiatric and addictive disorders: A systematic review, J Psychiatr Res, 2021, vol. 137: 273-282, doi: 10.1016/j.jpsychires.2021.03.002.
A. M. Sherwood, Clinical Consideration of 5-MeO-DMT, 2019, doi: 10.13140/RG.2.2.24508.69769.
L. Ley et al., Comparative acute effects of mescaline, lysergic acid diethylamide, and psilocybin in a randomized, double-blind, placebo-controlled cross-over study in healthy participants, Neuropsychopharmacology, 2023 doi: 10.1038/s41386-023-01607-2.
G. C. Glatfelter et al., Comparative Pharmacological Effects of Lisuride and Lysergic Acid Diethylamide Revisited, ACS Pharmacology & Translational Science, 2024, doi: 10.1021/acsptsci.3c00192.
C. P. plc, Compass Pathways plc F-1, 2020.
D. Toker et al., Consciousness is supported by near-critical cortical electrodynamics, 2021, doi: 10.1101/2021.06.10.447959.
S. N. Calderon et al., Considerations in assessing the abuse potential of psychedelics during drug development, Neuropharmacology, 2022, doi: 10.1016/j.neuropharm.2022.109352.
A. L. Halberstadt et al., Correlation between the potency of hallucinogens in the mouse head-twitch response assay and their behavioral and subjective effects in other species, Neuropharmacology, 2020, vol. 167, doi: 10.1016/j.neuropharm.2019.107933.
R. V. Lima da Cruz et al., Corrigendum: A Single Dose of 5-MeO-DMT Stimulates Cell Proliferation, Neuronal Survivability, Morphological and Functional Changes in Adult Mice Ventral Dentate Gyrus, Front Mol Neurosci, 2019, vol. 12: 79, doi: 10.3389/fnmol.2019.00079.
L. V. Danyeli et al., Cortical thickness of the posterior cingulate cortex is associated with the ketamine-induced altered sense of self: An ultra-high field MRI study, J Psychiatr Res, 2024, vol. 172: 136-143, doi: 10.1016/j.jpsychires.2024.02.019.
A. C. M. Galvao et al., Cortisol Modulation by Ayahuasca in Patients With Treatment Resistant Depression and Healthy Controls, Front Psychiatry, 2018, vol. 9: 185, doi: 10.3389/fpsyt.2018.00185.
C. t. A. S. Meeting, CPDD 80th Annual Scientific Meeting Program, CPDD 80th Annual Scientific Meeting, 2018.
S. Brown et al., Current and Common Definitions of Treatment-Resistant Depression: Findings from a Systematic Review and Qualitative Interviews, Can J Psychiatry, 2019, vol. 64(6): 380-387, doi: 10.1177/0706743719828965.
A. Garcia-Romeu et al., Current perspectives on psychedelic therapy: use of serotonergic hallucinogens in clinical interventions, Int Rev Psychiatry, 2018, vol. 30(4): 291-316, doi: 10.1080/09540261.2018.1486289.
S. Laabi et al., Deciphering psilocybin: Cytotoxicity, anti-inflammatory effects, and mechanistic insights, Int Immunopharmacol, vol. 130, doi: 10.1016/j.intimp.2024.111753.
J. J. Gattuso et al., Default Mode Network Modulation by Psychedelics: A Systematic Review, Int J Neuropsychopharmacol, 2022, doi: 10.1093/ijnp/pyac074.
K. Garber, Delix Therapeutics: psychedelics without the trip, 2022, https://doi.org/10.1038/d41587-022-00006-0.
M. I. Chambers et al., Detection and Quantification of Psychoactive N,N-Dimethyltryptamine in Ayahuasca Brews by Ambient Ionization High-Resolution Mass Spectrometry, ACS Omega, 2020, vol. 5(44): 28547-28554, doi: 10.1021/acsomega.0c03196.
R. Martin et al., Determination of psilocin, bufotenine, LSD and its metabolites in serum, plasma and urine by SPE-LC-MS/MS, Int J Legal Med, 2013, vol. 127(3): 593-601, doi: 10.1007/s00414-012-0796-1.
R. M. C. Di Martino et al., Deuterium in drug discovery: progress, opportunities and challenges, Nat Rev Drug Discov, 2023, vol. 22(7): 562-584, doi: 10.1038/s41573-023-00703-8.
S. J. Tai et al., Development and Evaluation of a Therapist Training Program for Psilocybin Therapy for Treatment-Resistant Depression in Clinical Research, Front Psychiatry, 2021, vol. 12, doi: 10.3389/fpsyt.2021.586682.
P. A. Scott et al., Differential induction of 5-HT1A-mediated responses in vivo by three chemically dissimilar 5-HT1A agonists, Pharmacol Exp Ther, 1994, vol. 270(1): 198-208.
F. Holze et al., Direct comparison of the acute effects of lysergic acid diethylamide and psilocybin in a double-blind placebo-controlled study in healthy subjects, Neuropsychopharmacology, 2022, doi: 10.1038/s41386-022-01297-2.
F. Holze et al., Distinct acute effects of LSD, MDMA, and D-amphetamine in healthy subjects, Neuropsychopharmacology, 2020, vol. 45(3): 462-471, doi: 10.1038/s41386-019-0569-3.
T. Hirschfeld et al., Dose-response relationships of psilocybin-induced subjective experiences in humans, Journal of Psychopharmacology, 2021, vol. 35(4): 384-397.
M. E. Liechti et al., Dosing Psychedelics and MDMA, Curr Top Behav Neurosci, 2021, doi: 10.1007/7854_2021_270.
Ema, Draft guideline on clinical investigation of medicinal products in the treatment of depression, 2023.
J. Fox et al., Drugs of Abuse and Novel Psychoactive Substances at Outdoor Music Festivals in Colorado, Subst Use Misuse, 2018, vol. 53(7): 1203-1211, doi: 10.1080/10826084.2017.1400067.
L. D. Lord et al., Dynamical exploration of the repertoire of brain networks at rest is modulated by psilocybin, Neuroimage, 2019, vol. 199: 127-142, doi: 10.1016/j.neuroimage.2019.05.060.
J. Acosta-Urquidi, EEG studies of the acute effects of 5-MeO-DMT, WBAC, 2018.
M. A. Critchley et al., Effects in the X-maze anxiety model of agents acting at 5-HT1 and 5-HT2 receptors, Psychopharmacology (Berl), 1987, vol. 93(4): 502-6, doi: 10.1007/BF00207243.
J. Neumann et al., Effects of hallucinogenic drugs on the human heart, Front Pharmacol, 2024, vol. 15, doi: 10.3389/fphar.2024.1334218.
L. P. Cameron et al., Effects of N, N-Dimethyltryptamine on Rat Behaviors Relevant to Anxiety and Depression, ACS Chem Neurosci, 2018, vol. 9(7): 1582-1590, doi: 10.1021/acschemneuro.8b00134.
J. E. Henningfield et al., Psychedelic drug abuse potential assessment research for new drug applications and Controlled Substances Act scheduling, Neuropharmacology, 2022, vol. 218, doi: 10.1016/j.neuropharm.2022.109220.
G. Oña et al., Psychedelic drugs as a long-needed innovation in psychiatry, Qeios, 2020, doi: 10.32388/t3em5e.2.
K. Corrigan et al., Psychedelic perceptions: mental health service user attitudes to psilocybin therapy, Irish Journal of Medical Science (1971-), 2022, vol. 191(3): 1385-1397.
D. Nutt et al., Psychedelic Psychiatry's Brave New World, Cell, 2020, vol. 181(1): 24-28, doi: 10.1016/j.cell.2020.03.020.
K. K. Kaup et al., Psychedelic replications in virtual reality and their potential as a therapeutic instrument: an open-label feasibility study, Front Psychiatry, 2023, vol. 14, doi: 10.3389/fpsyt.2023.1088896.
R. Petranker et al., Psychedelic Research and the Need for Transparency: Polishing Alice's Looking Glass, Front Psychol, 2020, vol. 11, doi: 10.3389/fpsyg.2020.01681.
D. E. McCulloch et al., Psychedelic resting-state neuroimaging: A review and perspective on balancing replication and novel analyses, Neurosci Biobehav Rev, 2022, vol. 138, doi: 10.1016/j.neubiorev.2022.104689.
J. R. Kelly et al., Psychedelic Science in Post-Covid Psychiatry, Ir J Psychol Med, 2020, pp. 1-18, doi: 10.1017/ipm.2020.94.
N. G. Glynos et al., Psychedelic substitution: altered substance use patterns following psychedelic use in a global survey, Frontiers in Psychiatry, 2024, vol. 15, doi: 10.3389/fpsyt.2024.1349565.

(56) References Cited

OTHER PUBLICATIONS

P. Eischens et al., Psychedelic therapy as a complementary treatment approach for alcohol use disorders, Journal of Psychedelic Studies, 2018, vol. 2(1): 36-44, doi: 10.1556/2054.2018.005.
K. Ko et al., Psychedelic therapy for depressive symptoms: A systematic review and meta-analysis, J Affect Disord, 2023, vol. 322: 194-204, doi: 10.1016/j.jad.2022.09.168.
M. Marks et al., Psychedelic therapy: a roadmap for wider acceptance and utilization, Nature Medicine, 2021, vol. 27(10): 1669-1671.
J. R. Kelly et al., Psychedelic Therapy's Transdiagnostic Effects: A Research Domain Criteria (RDoC) Perspective, Front Psychiatry, 2021, vol. 12, doi: 10.3389/fpsyt.2021.800072.
A. K. Davis et al., Psychedelic Treatment for Trauma-Related Psychological and Cognitive Impairment Among US Special Operations Forces Veterans, Chronic Stress (Thousand Oaks), 2020, vol. 4, doi: 10.1177/2470547020939564.
J. J. Breeksema et al., Psychedelic Treatments for Psychiatric Disorders: A Systematic Review and Thematic Synthesis of Patient Experiences in Qualitative Studies, CNS Drugs, 2020, vol. 34(9):925-946, doi: 10.1007/s40263-020-00748-y.
E. E. Schenberg, Psychedelic-Assisted Psychotherapy: A Paradigm Shift in Psychiatric Research and Development, Front Pharmacol, 2018, vol. 9: 733, doi: 10.3389/fphar.2018.00733.
C. Dong et al., Psychedelic-inspired drug discovery using an engineered biosensor, Cell, 2021, vol. 184(10): 2779-2792 e18, doi: 10.1016/j.cell.2021.03.043.
D. J. Heal et al., Psychedelics—Re-opening the doors of perception, Neuropharmacology, 2018, vol. 142: 1-6, doi: 10.1016/j.neuropharm.2018.08.024.
R. L. Carhart-Harris et al., Psychedelics and connectedness Psychopharmacology (Berl), 2018, vol. 235(2): 547-550, doi: 10.1007/s00213-017-4701-y.
F. Scholkmann et al., Psychedelics and fNIRS neuroimaging: exploring new opportunities, Neurophotonics, 2023, vol. 10(1), doi: 10.1117/1.NPh.10.1.013506.
P. J. Teixeira et al., Psychedelics and health behaviour change, J Psychopharmacol, 2022, vol. 36(1): 12-19, doi: 10.1177/02698811211008554.
C. M. H. de Vos et al., Psychedelics and Neuroplasticity: A Systematic Review Unraveling the Biological Underpinnings of Psychedelics, Front Psychiatry, 2021, vol. 12, doi: 10.3389/fpsyt.2021.724606.
C. M. Reiff et al., Psychedelics and Psychedelic-Assisted Psychotherapy, Am J Psychiatry, 2020, vol. 177(5): 391-410, doi: 10.1176/appi.ajp.2019.19010035.
T. Barba et al., Psychedelics and sexual functioning: a mixed-methods study, Sci Rep, 2024, vol. 14(1): 2181, doi: 10.1038/s41598-023-49817-4.
R. L. Carhart-Harris et al., Psychedelics and the essential importance of context, J Psychopharmacol, 2018, vol. 32(7): 725-731, doi: 10.1177/0269881118754710.
C. Thompson et al., Psychedelics as a novel approach to treating autoimmune conditions, Immunol Lett, 2020, vol. 228: 45-54, doi: 10.1016/j.imlet.2020.10.001.
G. Scott et al., Psychedelics as a treatment for disorders of consciousness, Neurosci Conscious, 2019, 1, niz003, doi: 10.1093/nc/niz003.
K. Rasmussen et al., Psychedelics as Standard of Care? Many Questions Remain, Camb Q Healthc Ethics, 2022, vol. 31(4): 477-481, doi: 10.1017/S096318012200010X.
M. Kalfas et al., "Psychedelics for treatment resistant depression: are they game changers?" Expert Opin Pharmacother, 2023, doi: 10.1080/14656566.2023.2281582.
A. Inserra et al., Psychedelics in Psychiatry: Neuroplastic, Immunomodulatory, and Neurotransmitter Mechanisms, Pharmacol Rev, 2021, vol. 73(1): 202-277, doi: 10.1124/pharmrev.120.000056.
O. G. Bosch et al., Psychedelics in the treatment of unipolar and bipolar depression, Int J Bipolar Disord, 2022, vol. 10(1): 18, doi: 10.1186/s40345-022-00265-5.
M. V. Vargas et al., Psychedelics promote neuroplasticity through the activation of intracellular 5-HT2A receptors, Science, 2023, vol. 379(6633): 700-706, doi: 10.1126/science.adf0435.
C. Ly et al., Psychedelics Promote Structural and Functional Neural Plasticity, Cell Rep, 2018, vol. 23(11): 3170-3182, doi: 10.1016/j.celrep.2018.05.022.
R. Nardou et al., Psychedelics reopen the social reward learning critical period Nature, 2023, pp. 1-9.
M. Hibicke et al., Psychedelics, but Not Ketamine, Produce Persistent Antidepressant-like Effects in a Rodent Experimental System for the Study of Depression, ACS Chem Neurosci, 2020, vol. 11(6): 864-871, doi: 10.1021/acschemneuro.9b00493.
R. Milliere et al., Psychedelics, Meditation, and Self-Consciousness, Front Psychol, 2018, vol. 9: 1475, doi: 10.3389/fpsyg.2018.01475.
K. Ko et al., Psychedelics, Mystical Experience, and Therapeutic Efficacy: A Systematic Review, Front Psychiatry, 2022, vol. 13, doi: 10.3389/fpsyt.2022.917199.
N. Gukasyan et al., Psychedelics, placebo effects, and set and setting: Insights from common factors theory of psychotherapy, Transcultural psychiatry, 2022, vol. 59(5): 652-664.
H. Lowe et al., Psychedelics: alternative and potential therapeutic options for treating mood and anxiety disorders, Molecules, 2022, vol. 27(8): 2520.
S. J. Belouin et al., Psychedelics: Where we are now, why we got here, what we must do, Neuropharmacology, 2018, vol. 142: 7-19, doi: 10.1016/j.neuropharm.2018.02.018.
P. J. Eugster et al., Quantification of serotonin and eight of its metabolites in plasma of healthy volunteers by mass spectrometry, Clin Chim Acta, 2022, vol. 535: 19-26, doi: 10.1016/j.cca.2022.08.012.
R. J. Zeifman et al., Rapid and sustained decreases in suicidality following a single dose of ayahuasca among individuals with recurrent major depressive disorder: results from an open-label trial, Psychopharmacology (Berl), 2021, vol. 238(2): 453-459, doi: 10.1007/s00213-020-05692-9.
R. L. Carhart-Harris et al., Rebus and the Anarchic Brain: Toward a Unified Model of the Brain Action of Psychedelics, Pharmacol Rev, 2019, vol. 71(3): 316-344, doi: 10.1124/pr.118.017160.
S. Kopf et al., Recent Developments for the Deuterium and Tritium Labeling of Organic Molecules, Chem Rev, 2022, vol. 122(6): 6634-6718, doi: 10.1021/acs.chemrev.1c00795.
K. F. Kiilerich et al., Repeated low doses of psilocybin increase resilience to stress, lower compulsive actions, and strengthen cortical connections to the paraventricular thalamic nucleus in rats, Mol Psychiatry, 2023, vol. 28(9): 3829-3841, doi: 10.1038/s41380-023-02280-z.
E. James et al., Reply to: 5-MeO-DMT has not been found in traditional ayahuasca preparations and the combination of 5-MeO-DMT with MAOIs is dangerous, Hum Psychopharmacol, 2022, vol. 37(3): e2840, doi: 10.1002/hup.2840.
C. J. Foldi et al., Rethinking Therapeutic Strategies for Anorexia Nervosa: Insights From Psychedelic Medicine and Animal Models, Front Neurosci, 2020, vol. 14: 43, doi: 10.3389/fnins.2020.00043.
R. S. Giovanni Martinotti et al., Review. Hallucinogen Persisting Perception Disorder: Etiology, Clinical Features, and Therapeutic Perspectives, Brain Sciences, 2018, vol. 8(47): 1-18, doi: 10.3390/brainsci803004.
S. K. Morton E et al., Risks and benefits of psilocybin use in people with bipolar disorder: An international web-based survey on experiences of 'magic mushroom' consumption, Journal of Psychopharmacology, 2023, vol. 37(1): 49-60, doi: 10.1177/02698811221131997.
M. Falchi-Carvalho et al., Safety and tolerability of inhaled N,N-Dimethyltryptamine (BMND01 candidate): A phase I clinical trial, Eur Neuropsychopharmacol, 2023, vol. 80: 27-35, doi: 10.1016/j.euroneuro.2023.12.006.
T. Scientific, Safety Data Sheet N,N-Dimethyl-5-methoxytryptamine, 2017.
E. James et al., Safety, tolerability, pharmacodynamic and well being effects of SPL026 (dimethyltryptamine fumarate) in healthy participants: a randomized, placebo-controlled phase 1 trial, Front Psychiatry, 2023, vol. 14, doi: 10.3389/fpsyt.2023.1305796.

(56) References Cited

OTHER PUBLICATIONS

S. Reiche et al., Serotonergic hallucinogens in the treatment of anxiety and depression in patients suffering from a life-threatening disease: A systematic review, Prog Neuropsychopharmacol Biol Psychiatry, 2018, vol. 81: 1-10, doi: 10.1016/j.pnpbp.2017.09.012.
T. F. Varley et al., Serotonergic psychedelics LSD & psilocybin increase the fractal dimension of cortical brain activity in spatial and temporal domains, Neuroimage, 2020, vol. 220, doi: 10.1016/j.neuroimage.2020.117049.
Souza et al., 5-MeO-DMT induces sleep-like LFP spectral signatures in the hippocampus and prefrontal cortex of awake rats, Sci Rep, 2024; 14(1): 11281, DOI: 10.1038/s41598-024-61474-9.
Aday et al., "Psychedelic-assisted psychotherapy: Where is the psychotherapy research?" Psychopharmacology, 2024; pp. 1-10.
Kishon et al., A rapid narrative review of the clinical evolution of psychedelic treatment in clinical trials, Npj Ment Health Res, 2024; 3(1): 33; DOI: 10.1038/s44184-024-00068-9.
Reddit Forum, Greatmoosey—my first 5meodmt experience, Sep. 28, 2019; www.reddit.com/r/5MeODMT/comments/dai2dp/my_first_5meodmt_experience_12mg_vaporized/?share_id=2OegQw7bxUmdqaFM0in_&utm_content=2&utm_medium=ios_app&utm name=ioscss&utm source=share&utm term=10".
Reddit Forum, Honeycomb—Intro topic 50868, Feb. 27, 2019; www.forums.5meodmt.org/index.php/topic,50868.msg55861.html#msg55861.
Reddit Forum, DeletinMySocialMedia—Bufo 5-MEO-DMT has practically cured me of my anxiety, insomnia and of childhood traumas, Jun. 9, 2021; www.reddit.com/r/5MeODMT/comments/nvi049/bufo_5meodmt_has_practically_cured_me_of_my/.
Reddit Forum, Repulsive-Yam-3084—My journey with 5MEODMT, Mar. 2, 2022; www.reddit.eom/r/5MeODMT/comments/t592jk/myJourney_with_5meodmt/.
Lima, On the anxiolytic effects of 5-MeO-DMT in the mouse brain and behaviour, 2022; www://repositorio.ufrn.br/bitstream/123456789/48565/1/Dosefeitosansioliticos Lima 2022.pdf.
Third party observation filed in PCT/EP2023/057857 (WO2023186816), Jun. 25, 2024.
ISR issued in WIPO Patent Application No. PCT/EP2024/050139 (WO2024146917), dated Mar. 13, 2024.
Information on Search Strategy issued in WIPO Patent Application No. PCT/EP2024/050139 (WO2024146917), dated Jul. 11, 2024.
Written Opinion issued in WIPO Patent Application No. PCT/EP2024/050139 (WO2024146917), dated Jul. 11, 2024.
Office Action issued in MX/a/2021/009941 (WO2020/169850) dated Apr. 23, 2024, translation.
ISR issued in WIPO Patent Application No. PCT/EP2023/057870, dated Jul. 14, 2023.
ISR issued in WIPO Patent Application No. PCT/EP2023/057871, dated Jun. 27, 2023.
ISR issued in WIPO Patent Application No. PCT/EP2023/057842, dated Jul. 12, 2023.
ISR issued in WIPO Patent Application No. PCT/EP2023/057845, dated Jul. 12, 2023.
ISR issued in WIPO Patent Application No. PCT/EP2023/057867, dated Sep. 19, 2023.
ISR issued in WIPO Patent Application No. PCT/EP2023/057868, dated Sep. 19, 2023.
ISR issued in WIPO Patent Application No. PCT/EP2023/057857, dated Jul. 12, 2023.
ISR issued in WIPO Patent Application No. PCT/EP2023/057875, dated Jul. 5, 2023.
ISR issued in WIPO Patent Application No. PCT/EP2023/057873, dated Jul. 13, 2023.
ISR issued in WIPO Patent Application No. PCT/EP2023/057874, dated Jun. 29, 2023.
ISR issued in WIPO Patent Application No. PCT/EP2023/057827, dated Jul. 13, 2023.
ISR issued in WIPO Patent Application No. PCT/EP2023/057828, dated Jul. 13, 2023.
ISR issued in WIPO Patent Application No. PCT/EP2023/057876, dated Jul. 7, 2023.
ISR issued in WIPO Patent Application No. PCT/EP2023/057879, dated Jul. 17, 2023.
ISR issued in WIPO Patent Application No. PCT/EP2023/057877, dated Jun. 29, 2023.
ISR issued in WIPO Patent Application No. PCT/EP2023/057878, dated Jul. 7, 2023.
ISR issued in WIPO Patent Application No. PCT/EP2023/057883, dated Jul. 13, 2023.
ISR issued in WIPO Patent Application No. PCT/EP2023/057885, dated Jul. 7, 2023.
Written Opinion issued in WIPO Patent Application No. PCT/EP2023/057870, Oct. 5, 2023.
Written Opinion issued in WIPO Patent Application No. PCT/EP2023/057871, Oct. 5, 2023.
Written Opinion issued in WIPO Patent Application No. PCT/EP2023/057842, Oct. 5, 2023.
Written Opinion issued in WIPO Patent Application No. PCT/EP2023/057845, Oct. 5, 2023.
Written Opinion issued in WIPO Patent Application No. PCT/EP2023/057867, Oct. 5, 2023.
Written Opinion issued in WIPO Patent Application No. PCT/EP2023/057868, Oct. 5, 2023.
Written Opinion issued in WIPO Patent Application No. PCT/EP2023/057857, Oct. 5, 2023.
Written Opinion issued in WIPO Patent Application No. PCT/EP2023/057875, Oct. 5, 2023.
Written Opinion issued in WIPO Patent Application No. PCT/EP2023/057873, Oct. 5, 2023.
Written Opinion issued in WIPO Patent Application No. PCT/EP2023/057874, Oct. 5, 2023.
Written Opinion issued in WIPO Patent Application No. PCT/EP2023/057827, Oct. 5, 2023.
Written Opinion issued in WIPO Patent Application No. PCT/EP2023/057828, Oct. 5, 2023.
Written Opinion issued in WIPO Patent Application No. PCT/EP2023/057876, Oct. 5, 2023.
Written Opinion issued in WIPO Patent Application No. PCT/EP2023/057879, Oct. 5, 2023.
Written Opinion issued in WIPO Patent Application No. PCT/EP2023/057877, Oct. 5, 2023.
Written Opinion issued in WIPO Patent Application No. PCT/EP2023/057878, Oct. 5, 2023.
Written Opinion issued in WIPO Patent Application No. PCT/EP2023/057883, Oct. 5, 2023.
Written Opinion issued in WIPO Patent Application No. PCT/EP2023/057885, Oct. 5, 2023.
ISR issued in International Patent Application No. PCT/EP2020/067113, Jul. 28, 2020, translation.
Geyer M A et al., "Behavioural and pharmacological studies of pharmahuasca in rodents", European Neuropsychopharmacology, vol. 26, 2016, XP029787110, ISSN: 0924-977X, DOI: 10.1016/S0924-977X(16) 30889-6 examples 7-10, S120.
Alan K. Davis et al., "5-methoxy-N, N-dimethyltryptamine (5-MeO-DMT) used in a naturalistic group setting is associated with unintended improvements in depression and anxiety", American Journal of Drug and Alcohol Abuse, vol. 45, No. 2, Mar. 1, 2019, pp. 161-169.
Uthaug et al., "Prospective examination of synthetic 5-methoxy-N,N-dimethyltryptamine inhalation: effects on salivary IL-6, cortisol levels, affect, and non-judgment", Psychopharmacology, Springer Verlag, Berlin DE, vol. 237, No. 3, Dec. 10, 2019, pp. 773-785.
ISR issued in WIPO Patent Application No. PCT/EP2020/054803, Jun. 24, 2020.
IPRP issued in WIPO Patent Application No. PCT/EP2020/054803, Aug. 10, 2020.
3rd Party Observation and Additional Comments filed in PCT/EP2020/054803, Jun. 28, 2021, English translation.
3rd Party Observation and Additional Comments filed in PCT/EP2020/054803. Jun. 29, 2021, English translation.
Palhano-Fontes F. et al., "Rapid antidepressant effects of the psychedelic ayahuasca in treatment-resistant depression: a randomised

(56) References Cited

OTHER PUBLICATIONS placebo-controlled trial", Psychological Medicine, Cambridge University Press, pp. 655-663 Jun. 15, 2018.
"Integrating with Depression", https://forums.5meodmt.org/index.php?topic=50972.0, Oct. 1, 2019.
"Testosterone for depression and anxiety", https://reddit.com/r/depressionregimens/comments/dw9qb0/testosterone_for_depression_and_anxiety, Nov. 14, 2019.
ISR issued in WIPO Patent Application No. PCT/EP2020/054804, May 29, 2020.
IPRP issued in WIPO Patent Application No. PCT/EP2020/054804, Aug. 10, 2020.
Palhano-Fontes et al., "A randomized placebo-controlled trial on the antidepressant effects of the psychedelic ayahuasca in treatment-resistant depression," https://www.biorxiv.org/content/10.1101/103531v2, Aug. 15, 2017.
Third-Party Observation filed in EP3927337, Jun. 28, 2022.
Third-Party Observation filed in EP3927337, Jun. 21, 2021.
2nd Third-Party Observation filed in EP3927337, Jun. 21, 2021.
Third-Party Observation filed in EP3927338, Aug. 22, 2021.
Third-Party Observation filed in EP3927338, Jun. 28, 2022.
Third-Party Observation and Additional Comments filed in PCT/EP20/54804, Jun. 28, 2021.
Yu AM. "Indolealkylamines: biotransformations and potential drug-drug interactions." AAPS J. 2008;10(2):242-253.
Zimmerman M, Martinez JH, Attiullah N, Friedman M, Toba C, Boerescu DA. "The remission from depression questionnaire as an outcome measure in the treatment of depression." Depress Anxiety. 2014;31(6):533-538.
Carhart-Harris, "Serotonin, psychedelics and psychiatry." World Psychiatry 17:3, pp. 358-359, Oct. 2018.
McClure-Begley et al., "The promises and perils of psychedelic pharmacology for psychiatry." Nature Reviews Drug Discovery, vol. 21, pp. 463-473 (2022).
1st Third-Party Submission filed in U.S. Appl. No. 17/431,626, filed Jun. 16, 2022.
2nd Third-Party Submission filed in U.S. Appl. No. 17/431,626, filed Jun. 16, 2022.
3rd Third-Party Submission filed in U.S. Appl. No. 17/431,626, filed Jun. 16, 2022.
Schenberg, Translation and cultural adaptation of the States of Consciousness Questionnaire (SOCQ) and statistical validation of the Mystical Experience Questionnaire (MEQ30) in Brazilian Portuguese, vol. 44(1) pp. 1-5, 2017, Archives of Clinical Psychiatry.
Shulgin et al., Tihkal: Tryptamines I Have Known and Loved: The Chemistry Continues, 1997, Transform Press.
Hermann, Psychiatric Comorbidity in Chronic Epilepsy: Identification, Consequences, and Treatment of Major Depression, vol. 41(2) pp. 31-41, 2005, Epilepsia.
Erowid, 5-MeO-DMT Dosage, Retrieved from Erowid 1999, Retrieved from Web Archive Apr. 7, 2000. https://web.archive.Org/web/20000407105145/https://erowid.org/chemicals/5meo_dmt/5meo_dmt_dose.shtml.
Herrmann,The Sunnybrook Stroke Study: a prospective study of depressive symptoms and 7 functional outcome, vol. 29(3) pp. 618-624, 1998, Stroke.
Mohebbi, Patient centric measures for a patient centric era Agreement and convergent between ratings on the Patient Global Impression of Improvement (PGI-I) scale and the Clinical Global Impressions—Improvement (CGI-S) scale in bipolar and major depressive disorder, vol. 53 pp. 17-22, 2018, European Psychiatry.
Muller, Differentiating moderate and severe depression using the Montgomery-Asberg depression rating scale (MADRS), vol. 77 pp. 255-260, 2003, Journal of Affective Disorders.
Santos, Long-term effects of ayahuasca in patients with recurrent depression: a 5-year qualitative follow-up, vol. 45(1) pp. 22-24, 2018, Archives of Clinical Psychiatry.
Ingebrethsen, Electronic cigarette aerosol particle size distribution measurements, vol. 24(14) pp. 976-984, 2012, Inhalation Toxicology.
Sellers EM, Leiderman DB. "Psychedelic Drugs as Therapeutics: No Illusions About the Challenges." Clin Pharmacol Ther. 2018;103(4):561-564.
Sellers EM, Romach MK, Leiderman DB. "Studies with psychedelic drugs in human volunteers." Neuropharmacology. 2018;142:116-134.
Sessa B. "The 21st century psychedelic renaissance: heroic steps forward on the back of an elephant." Psychopharmacology (Berl). 2018;235(2):551-560.
Shearman GT, Tolcsvai L. "Effect of the selective 5-HT3 receptor antagonists ICS 205-930 and MDL 72222 on 5-HTP-induced head shaking and behavioral symptoms induced by 5-methoxy-N,N,dimethyltryptamine in rats: comparison with some other 5-HT receptor antagonists." Psychopharmacology (Berl). 1987;92(4):520-523.
Shen HW, Jiang XL, Winter JC, Yu AM. "Psychedelic 5-methoxy-N,N-dimethyltryptamine: metabolism, pharmacokinetics, drug interactions, and pharmacological actions." Curr Drug Metab. 2010;11(8):659-666.
Shen HW, Jiang XL, Yu AM. "Development of a LC-MS/MS method to analyze 5-methoxy-N,N-dimethyltryptamine and bufotenine, and application to pharmacokinetic study." Bioanalysis. 2009;1(1):87-95.
Shen HW, Jiang XL, Yu AM. "Nonlinear pharmacokinetics of 5-methoxy-N,N-dimethyltryptamine in mice." Drug Metab Dispos. 2011;39(7):1227-1234.
Shen HW, Wu C, Jiang XL, Yu AM. "Effects of monoamine oxidase inhibitor and cytochrome P450 2D6 status on 5-methoxy-N,N-dimethyltryptamine metabolism and pharmacokinetics." Biochem Pharmacol. 2010;80(1):122-128.
Shephard RA, Broadhurst PL. "Hyponeophagia and arousal in rats: effects of diazepam, 5-methoxy-N,N-dimethyltryptamine, d-amphetamine and food deprivation." Psychopharmacology (Berl). 1982;78(4):368-372.
Shulgin A. "Psychotomimetic Drugs," 5-MeO-DMT comment. 1970.
Shulgin AS, A. Erowid Online Books TIHKAL—#38 5-MEO-DMT; 2015.
Simonovic M, Meltzer HY. "Repeated administration of 5-methoxy-N,N-dimethyltryptamine to male rats potentiates stimulation of prolactine secretino by serotonin agonists." European Journal of Pharmacology. 1979;58(4):399-405.
Simonovic M, Meltzer HY. "Biphasic effect of 5-methoxy-N,N-dimethyltryptamine on rat prolactin secretion." Brain Research. 1983;272(2):269-275.
Singleton C. "Increased responsiveness to 5-methoxy-N, N-dimethyltryptamine in mice on a high tryptophan diet. Neuropharmacology." 1979;18(6):569-572.
Sitaram BR, Lockett L, Blackman GL, McLeod WR. "Urinary excretion of 5-methoxy-N,N-dimethyltryptamine, N,N-dimethyltryptamine and their N-oxides in the rat." Biochemical Pharmacology. 1987;36(13):2235-2237.
Sitaram BR, Lockett L, Talomsin R, Blackman GL, McLeod WR. "In vivo metabolism of 5-methoxy-N, N-dimethyltryptamine and N,N-dimethyltryptamine in the rat." Biochemical Pharmacology. 1987;36(9):1509-1512.
Sitaram BR, McLeod WR. "Observations on the metabolism of the psychotomimetic indolealkylamines: Implications for future clinical studies." Biological Psychiatry. 1990;28(10):841-848.
Sklerov J, Levine B, Moore KA, King T, Fowler D. "A fatal intoxication following the ingestion of 5-methoxy-N,N-dimethyltryptamine in an ayahuasca preparation." J Anal Toxicol. 2005;29(8):838-841.
Skolnick P, Weissman BA, Youdim MB. "Monoaminergic involvement in the pharmacological actions of buspirone." Br J Pharmacol. 1985;86(3):637-644.
Smant G, Goverse A, Stokkermans JP, De Boer JM, Pomp HR, Zilverentant JF, Overmars HA, Helder J, Schots A, Bakker J. "Potato root diffusate-induced secretion of soluble, basic proteins originating from the subventral esophageal glands of potato cyst nematodes." Phytopathology. 1997;87(8):839-845.
Smythies JR, Antun F. "Binding of tryptamine and allied compounds to nucleic acids."
Nature. 1969;223(5210):1061-1063.

(56) References Cited

OTHER PUBLICATIONS

Spencer DG, Jr., Glaser T, Traber J. "Serotonin receptor subtype mediation of the interoceptive discriminative stimuli induced by 5-methoxy-N,N-dimethyltryptamine." Psychopharmacology (Berl). 1987;93(2):158-166.
Stoff DM, GorcLick DA, Bozewicz T, Bridger WH, Gillin JC, Wyatt RJ. "The indole hallucinogens, N,N-dimethyltryptamine (DMT) and 5-methoxy-N,N-dimethyltryptamine (5-MeO-DMT), have different effects from mescaline on rat shuttlebox avoidance." Neuropharmacology. 1978;17(12):1035-1040.
Stolz JF, Marsden CA, Middlemiss DN. "Effect of chronic antidepressant treatment and subsequent withdrawal on [3H]-5-hydroxytryptamine and [3H]-spiperone binding in rat frontal cortex and serotonin receptor mediated behaviour." Psychopharmacology (Berl). 1983;80(2):150-155.
Strassman RJ. "Human psychopharmacology of N,N-dimethyltryptamine." Behavioural Brain Research. 1995;73(1-2):121-124.
Strassman RJ, Qualls CR. "Dose-response study of N,N-dimethyltryptamine in humans. I. Neuroendocrine, autonomic, and cardiovascular effects." Arch Gen Psychiatry. 1994;51(2):85-97.
Strassman RJ, Qualls CR, Berg LM. "Differential tolerance to biological and subjective effects of four closely spaced doses of N,N-dimethyltryptamine in humans." Biological Psychiatry. 1996;39(9):784-795.
Strassman RJ, Qualls CR, Uhlenhuth EH, Kellner R. "Dose-response study of N,N-dimethyltryptamine in humans. II. Subjective effects and preliminary results of a new rating scale." Arch Gen Psychiatry. 1994;51(2):98-108.
Studerus E, Gamma A, Vollenweider FX. "Psychometric evaluation of the altered states of consciousness rating scale (OAV)." PLoS One. 2010;5(8):e12412.
Susser E, Keyes K, Mascayano F. "Healthy pregnancy and prevention of psychosis." World Psychiatry. 2018;17(3):357-358.
Svenningsson P, Tzavara ET, Qi H, Carruthers R, Witkin JM, Nomikos GG, Greengard P. "Biochemical and behavioral evidence for antidepressant-like effects of 5-HT6 receptor stimulation." J Neurosci. 2007;27(15):4201-4209.
Szabo A, Kovacs A, Frecska E, Rajnavolgyi E. "Psychedelic N,N-dimethyltryptamine and 5-methoxy-N,N-dimethyltryptamine modulate innate and adaptive inflammatory responses through the sigma-1 receptor of human monocyte-derived dendritic cells." PLoS One. 2014;9(8):e106533.
Tagliazucchi E, Roseman L, Kaelen M, Orban C, Muthukumaraswamy SD, Murphy K, Laufs H, Leech R, McGonigle J, Crossley N, Bullmore E, Williams T, Bolstridge M, Feilding A, Nutt DJ, Carhart-Harris R. "Increased Global Functional Connectivity Correlates with LSD-Induced Ego Dissolution." Curr Biol. 2016;26(8):1043-1050.
Thier P, Wassle H. "Indoleamine-mediated reciprocal modulation of on-centre and off-centre ganglion cell activity in the retina of the cat." J Physiol. 1984;351:613-630.
Thomas G, Lucas P, Capler NR, Tupper KW, Martin G. "Ayahuasca-assisted therapy for addiction: results from a preliminary observational study in Canada." Curr Drug Abuse Rev. 2013;6(1):30-42.
Timmermann C, Roseman L, Williams L, Erritzoe D, Martial C, Cassol H, Laureys S, Nutt D, Carhart-Harris R. "DMT Models the Near-Death Experience." Front Psychol. 2018;9:1424.
Tittarelli R, Mannocchi G, Pantano F, Romolo FS. "Recreational use, analysis and toxicity of tryptamines." Curr Neuropharmacol. 2015;13(1):26-46.
Toshihiro Takahashi, Kazuhiro T, Tatsuo I, Kazuhiko Y, Ren I, Kiichi I, Shigeo N. "11C-labelling of indolealkylamine alkaloids and the comparative study of their tissue distributions." The International Journal of Applied Radiation and Isotopes. 1985;36(12):965-969.
Tricklebank MD, Forler C, Middlemiss DN, Fozard JR. "Subtypes of the 5-HT receptor mediating the behavioural responses to 5-methoxy-N,N-dimethyltryptamine in the rat." European Journal of Pharmacology. 1985;117(1):15-24.
Trulson ME, Jacobs BL. "Effects of 5-methoxy-N,N-dimethyltryptamine on behavior and raphe unit acitivity in freely moving cats." European Journal of Pharmacology. 1979;54(1-2):43-50.
Trulson ME, Keltch GF. "Development of tolerance to repeated administration of 5-methoxy-N, N-dimethyltryptamine in rats." European Journal of Pharmacology. 1985;108(1):33-37.
Turton S, Nutt DJ, Carhart-Harris RL. "A qualitative report on the subjective experience of intravenous psilocybin administered in an FMRI environment." Curr Drug Abuse Rev. 2014;7(2):117-127.
Uthaug MV, van Oorsouw K, Kuypers KPC, van Boxtel M, Broers NJ, Mason NL, Toennes SW, Riba J, Ramaekers JG. "Sub-acute and long-term effects of ayahuasca on affect and cognitive thinking style and their association with ego dissolution". Psychopharmacology (Berl). 2018.
Van den Buuse M, Ruimschotel E, Martin S, Risbrough VB, Halberstadt AL. "Enhanced effects of amphetamine but reduced effects of the hallucinogen, 5-MeO-DMT, on locomotor activity in 5-HT(1A) receptor knockout mice: implications for schizophrenia." Neuropharmacology. 2011;61(1-2):209-216.
Vollenweider FX, Kometer M. "The neurobiology of psychedelic drugs: implications for the treatment of mood disorders." Nat Rev Neurosci. 2010;11(9):642-651.
Vollenweider FX, Vollenweider-Scherpenhuyzen MF, Babler A, Vogel H, Hell D. "Psilocybin induces schizophrenia-like psychosis in humans via a serotonin-2 agonist action." Neuroreport. 1998;9(17):3897-3902.
Wada Y, Hasegawa H, Nakamura M, Yamaguchi N. "Behavioral and electroencephalographic effects of a serotonin receptor agonist (5-methoxy-N,N-dimethyltryptamine) in a feline model of photosensitive epilepsy." Neuroscience Letters. 1992;138(1):115-118.
Wang MJ, Liu JT, Chen HM, Lin JJ, Lin CH. "Comparison of the separation of nine tryptamine standards based on gas chromatography, high performance liquid chromatography and capillary electrophoresis methods." J Chromatogr A. 2008;1181(1-2):131-136.
Weil AT, Davis W. "Bufo alvarius: a potent hallucinogen of animal origin." Journal of Ethnopharmacology. 1994;41(1-2):1-8.
Winstock AR, Kaar S, Borschmann R. "Dimethyltryptamine (DMT): prevalence, user characteristics and abuse liability in a large global sample." J Psychopharmacol. 2014;28(1):49-54.
Winter JC, Amorosi DJ, Rice KC, Cheng K, Yu AM."Stimulus control by 5-methoxy-N,N-dimethyltryptamine in wild-type and CYP2D6-humanized mice." Pharmacol Biochem Behav. 2011;99(3):311-315.
Winter JC, Filipink RA, Timineri D, Helsley SE, Rabin RA. "The Paradox of 5-Methoxy-N,N-Dimethyltryptamine." Pharmacology Biochemistry and Behavior. 2000;65(1):75-82.
Winter JC, Rice KC, Amorosi DJ, Rabin RA., "Psilocybin-induced stimulus control in the rat." Pharmacol Biochem Behav. 2007;87(4):472-480.
Winther A. "LSD—verdens mest potente stof er tilbage." Anne Winther Ink Journalistik & Kommunikation; 2018.
Yakel JL, Trussell LO, Jackson MB. "Three serotonin responses in cultured mouse hippocampal and striatal neurons." The Journal of Neuroscience. 1988;8(4):1273-1285.
Yoshida S, Kuga T. "Two kinds of modification by 5-methoxy-N,N-dimethyltryptamine of contractile responses to electrical stimulation of isolated guinea-pig vas deferens." Jpn J Pharmacol. 1987;43(4):341-349.
Young R, Rosecrans JA, Glennon RA. "Behavioral effects of 5-methoxy-N,N-dimethyltryptamine and dose-dependent antagonism by BC-105." Psychopharmacology (Berl). 1983;80(2):156-160.
Young R, Rosecrans JA, Glennon RA. "Further studies on the dose-dependent stimulus properties of 5-methoxy-N,N-dimethyltryptamine." Pharmacology Biochemistry and Behavior. 1986;25(6):1207-1210.
Carhart-Harris, R. L.; Kaelen, M.; Whalley, M. G.; Bolstridge, M.; Feilding, A.; Nutt, D. J., "LSD enhances suggestibility in healthy volunteers," Psychopharmacology (Berl), 2015;232(4):785-94.
Cayman Chemical, "5-methoxy DMT Product Information," 2015.
Gonzalez, D.; Torrens, M.; Farre, M., "Acute Effects of the Novel Psychoactive Drug 2C-B on Emotions," Biomed Res Int, 2015;2015:643878.

(56) References Cited

OTHER PUBLICATIONS

Halberstadt, A. L., "Recent advances in the neuropsychopharmacology of serotonergic hallucinogens," Behavioural brain research, 2015;277:99-120.
Moreira, L. A.; Murta, M. M.; Gatto, C. C.; Fagg, C. W.; dos Santos, M. L., "Concise synthesis of N,N-dimethyltryptamine and 5-methoxy-N,N-dimethyltryptamine starting with bufotenine from Brazilian *Anadenanthera* ssp," Nat Prod Commun, 2015;10(4):581-4.
Oliveira-Lima, A. J.; Santos, R.; Hollais, A. W.; Gerardi-Junior, C. A.; Baldaia, M. A.; Wuo-Silva, R.; Yokoyama, T. S.; Costa, J. L.; Malpezzi-Marinho, E. L.; Ribeiro-Barbosa, P. C.; Berro, L. F.; Frussa-Filho, R.; Marinho, E. A., Effects of ayahuasca on the development of ethanol-induced behavioral sensitization and on a post-sensitization treatment in mice, Physiol Behav, 2015;142:28-36.
Riga, M. S. B., A.; Artigas, F.; Celeda, P., "The serotonergic hallucinogen 5-Methoxy-N,N dimethyltriptamine (5-MeO-DMT) disrupts cortical function. Reversal by antipsychotic drugs," 2015.
Schindler, E. A.; Gottschalk, C. H.; Weil, M. J.; Shapiro, R. E.; Wright, D. A.; Sewell, R. A., "Indoleamine Hallucinogens in Cluster Headache: Results of the Clusterbusters Medication Use Survey," J Psychoactive Drugs, 2015;47(5):372-81.
Schmid, Y.; Enzler, F.; Gasser, P.; Grouzmann, E.; Preller, K. H.; Vollenweider, F. X.; Brenneisen, R.; Muller, F.; Borgwardt, S.; Liechti, M. E., "Acute Effects of Lysergic Acid Diethylamide in Healthy Subjects," Biol Psychiatry, 2015;78(8):544-53.
Sessa, B.; Fischer, F. M., "Underground MDMA-, LSD- and 2-CB-assisted individual and group psychotherapy in Zurich: Outcomes, implications and commentary," Drug Science, Policy and Law, 2015;2.
Thoricatha, W., "At the Crossroads of Ibogaine and 5-MeO-DMT, An Interview with Dr Polanco," Psychedelic Times, 2015.
Barsuglia, J., "Overview of Crossroads Treatment Center, Current Research and UCSD FMRI Study," 2016.
Carbonaro, T. M.; Gatch, M. B., "Neuropharmacology of N,N-dimethyltryptamine," Brain Res Bull, 2016;126(Pt 1):74-88.
Catlow, B. J.; Jalloh, A.; Sanchez-Ramos, J., "Hippocampal Neurogenesis," Neuropathology of Drug Addictions and Substance Misuse, 2016:821-831.
Das, S.; Barnwal, P.; Ramasamy, A.; Sen, S.; Mondal, S., "Lysergic acid diethylamide: a drug of 'use'?" Ther Adv Psychopharmacol, 2016;6(3):214-28.
Dos Santos, R. G.; Osorio, F. L.; Crippa, J. A.; Riba, J.; Zuardi, A. W.; Hallak, J. E., "Antidepressive, anxiolytic, and antiaddictive effects of ayahuasca, psilocybin and lysergic acid diethylamide (LSD): a systematic review of clinical trials published in the last 25 years," Ther Adv Psychopharmacol, 2016;6(3):193-213.
Garcia-Romeu, A.; Kersgaard, B.; Addy, P. H., "Clinical applications of hallucinogens: A review," Exp Clin Psychopharmacol, 2016;24(4):229-68.
Incognita, T., "Integration project," 2016.
Incognita, T., "Feasability Study 2016: Bio-Assay of Bufo Alvarius Toad Secretions," 2016.
Millière, R. "Narrative Reports of Drug-Induced Ego Dissolution: A Quantitative Analysis," ICPR, 2016.
Mithoefer, M. C.; Grob, C. S.; Brewerton, T. D., "Novel psychopharmacological therapies for psychiatric disorders: psilocybin and MDMA," The Lancet Psychiatry, 2016;3(5):481-488.
Nexus, D., "5-MeO-DMT Vaporization," 2016.
Orion, D., "Exploring the Sacred Power of 5-MeO-DMT and the Psychedelic Toad Podcast with Dr. Gerardo Sandoval," Psychedelic Times, 2016.
Palamar, J. J.; Barratt, M. J.; Ferris, J. A.; Winstock, A. R., "Correlates of new psychoactive substance use among a self-selected sample of nightclub attendees in the United States," Am J Addict, 2016;25(5):400-7.
Peeters, F. P.; Ruhe, H. G.; Wichers, M.; Abidi, L.; Kaub, K.; van der Lande, H. J.; Spijker, J.; Huibers, M. J.; Schene, A. H., "The Dutch Measure for quantification of Treatment Resistance in Depression (DM-TRD): an extension of the Maudsley Staging Method," J Affect Disord, 2016;205:365-371.
Pokorny, T.; Preller, K. H.; Krachenmann, R.; Vollenweider, F. X., "Modulatory effect of the 5-HT1A agonist buspirone and the mixed non-hallucinogenic 5-HT1A/2A agonist ergotamine on psilocybin-induced psychedelic experience," Eur Neuropsychopharmacol, 2016;26(4):756-66.
Preller, K. H.; Pokorny, T.; Hock, A.; Kraehenmann, R.; Stampfli, P.; Seifritz, E.; Scheidegger, M.; Vollenweider, F. X., "Effects of serotonin 2A/1A receptor stimulation on social exclusion processing," Proc Natl Acad Sci U S A, 2016;113(18):5119-24.
Pytka, K.; Podkowa, K.; Rapacz, A.; Podkowa, A.; Zmudzka, E.; Olczyk, A.; Sapa, J.; Filipek, B., "The role of serotonergic, adrenergic and dopaminergic receptors in antidepressant-like effect," Pharmacol Rep, 2016;68(2):263-74.
Roger, R., "What Is the Difference between 5-MeO-DMT and DMT? Choosing a DMT Therapy," Psychedelic Times, 2016.
Sanches, R. F.; de Lima Osorio, F.; Dos Santos, R. G.; Macedo, L. R.; Maia-de-Oliveira, J. P.; Wichert-Ana, L.; de Araujo, D. B.; Riba, J.; Crippa, J. A.; Hallak, J. E., "Antidepressant Effects of a Single Dose of Ayahuasca in Patients With Recurrent Depression: A SPECT Study," J Clin Psychopharmacol, 2016;36(1):77-81.
Sutherland, R.; Peacock, A.; Whittaker, E.; Roxburgh, A.; Lenton, S.; Matthews, A.; Butler, K.; Nelson, M.; Burns, L.; Bruno, R., "New psychoactive substance use among regular psychostimulant users in Australia, 2010-2015," Drug Alcohol Depend, 2016;161:110-8.
Thoricatha, W., "Psychedelic Research with Ibogaine and 5-MeO-DMT an Interview with Dr. Joseph Barsuglia," Psychedelic Times, 2016.
Varlet, V., "Drug Vaping: From the Dangers of Misuse to New Therapeutic Devices," Toxics, 2016;4(4).
Barsuglia, J. D., A. K., "Characterization of Mystical Experiences Occasioned by 5-MeO-DMTContaining Toad Bufotoxin and Comparison with Prior Psilocybin Studies," 3rd International Psychedelic Science Conference, 2017.
Cerilliant, "Safety Data Sheet 5-Methoxy-N,N-Dimethyltryptamine," 2017.
De Veen, B. T.; Schellekens, A. F.; Verheij, M. M.; Homberg, J. R., "Psilocybin for treating substance use disorders?," Expert Rev Neurother, 2017;17(2):203-212.
Dolder, P. C.; Schmid, Y.; Steuer, A. E.; Kraemer, T.; Rentsch, K. M.; Hammann, F.; Liechti, M. E., "Pharmacokinetics and Pharmacodynamics of Lysergic Acid Diethylamide in Healthy Subjects," Clin Pharmacokinet, 2017;56(10):1219-1230.
Dos Santos, R. G.; Bouso, J. C.; Hallak, J. E. C., "The antiaddictive effects of ibogaine: A systematic literature review of human studies," Journal of Psychedelic Studies, 2017;1(1):20-28.
Teafaerie, "Breakthrough in Technology (DMT Made Easy)—DMT & 5-MeO-DMT (exp66957)," erowid.org Nov. 9, 2007, erowid.org/exp/66957.
Fabregat-Safont, D.; Barneo-Munoz, M.; Martinez-Garcia, F.; Sancho, J. V.; Hernandez, F.; Ibanez, M., "Proposal of 5-methoxy-N-methyl-N-isopropyltryptamine consumption biomarkers through identification of in vivo metabolites from mice," J Chromatogr A, 2017;1508:95-105.
Jerome, L., Investigator's Brochure—Psilocybin, 2017.
Kyzar, E. J.; Nichols, C. D.; Gainetdinov, R. R.; Nichols, D. E.; Kalueff, A. V., "Psychedelic Drugs in Biomedicine," Trends Pharmacol Sci, 2017;38(11):992-1005.
Letheby, C.; Gerrans, P., "Self unbound: ego dissolution in psychedelic experience," Neurosci Conscious, 2017;2017(1):nix016.
Liechti, M. E., "Modern Clinical Research on LSD," Neuropsychopharmacology, 2017;42(11):2114-2127.
Liechti, M. E.; Dolder, P. C.; Schmid, Y., "Alterations of consciousness and mystical-type experiences after acute LSD in humans," Psychopharmacology (Berl), 2017;234(9-10):1499-1510.
Malcolm, B., "Ayahuasca: Spiritual Pharmacology & Drug Interactions," Aware Project, 2017.
Milliere, R., "Looking for the Self: Phenomenology, Neurophysiology and Philosophical Significance of Drug-induced Ego Dissolution," Front Hum Neurosci, 2017;11:245.

(56) References Cited

OTHER PUBLICATIONS

Nichols, D. E.; Johnson, M. W.; Nichols, C. D., "Psychedelics as Medicines: An Emerging New Paradigm," Clin Pharmacol Ther, 2017;101(2):209-219.
Office Action issued in EP 20710060.3, Dec. 16, 2022.
ISR issued in WIPO Patent Application No. PCT/EP2020/067113, Jul. 28, 2020.
ISR issued in WIPO Patent Application No. PCT/EP2021/054502, Apr. 29, 2021.
IPRP issued in WIPO Patent Application No. PCT/EP2021/054502, Aug. 30, 2022.
Third Party Submission filed in U.S. Appl. No. 17/431,626, filed Sep. 14, 2022.
Third Party Observation filed in U.S. Appl. No. 17/431,634, filed Oct. 13, 2022.
Voineskos, D. et a., "Management of Treatment-Resistant Depression: Challenges and Strategies," Neuropsychiatric Disease and Treatment, vol. 16, pp. 221-234 (2020).
Abdulqader A. Alhaider MH, George L. Wilcox Intrathecal 5-methoxy-N,N-dimethyltryptamine in mice modulates 5-HT 1 and 5-HT 3 receptors. European Journal of Pharmacology. 1993;249(2):151-160.
Acosta-Urquidi J., "QEEG studies of the acute effects of the visionary tryptamine DMT." Cosmos and History: The Journal of Natural and Social Philosophy. 2015;11(2):115-129.
Adell A, Sarna GS, Hutson PH, Curzon G., "An in vivo dialysis and behavioural study of the release of 5-HT by p-chloroamphetamine in reserpine-treated rats." Br J Pharmacol. 1989;97(1):206-212.
Agurell S, Holmstedt B, Lindgren JE., "Metabolism of 5-methoxy-N,N dimethyltryptamine-14C in the rat." Biochemical Pharmacology. 1969;18(12):2771-2781.
Ahlborg U, Holmstedt B, Lindgren J. "Fate and Metabolism of Some Hallucinogenic Indolealkylamines." 1968;6:213-229.
Anand A, Li Y, Wang Y, Lowe MJ, Dzemidzic M. "Resting state corticolimbic connectivity abnormalities in unmedicated bipolar disorder and unipolar depression." Psychiatry Res. 2009;171(3):189-198.
Andersson M, Persson M, Kjellgren A. "Psychoactive substances as a last resort—a qualitative study of self-treatment of migraine and cluster headaches." Harm Reduct J. 2017;14(1):60.
Araujo AM, Carvalho F, Bastos Mde L, Guedes de Pinho P, Carvalho M. "The hallucinogenic world of tryptamines: an updated review." Arch Toxicol. 2015;89(8):1151-1173.
Archer T, Danysz W, Jonsson G, Minor BG, Post C. "5-Methoxy-N,N-dimethyltryptamine-induced analgesia is blocked by alpha-adrenoceptor antagonists in rats." Br J Pharmacol. 1986;89(2):293-298.
Archer T, Minor BG, Post C. "Blockade and reversal of 5-Methoxy-N, N-Dimethyltryptamine-induced analgesia following noradrenaline depletion." Brain Research. 1985;333(1):55-61.
Archer T, Tandberg B, Renyi L, Ross SB. "Antagonism of 5-methoxy-N,N-dimethyltryptamine-induced changes in postdecapitation convulsions in rats by repeated treatment with drugs enhancing 5-hydroxytryptamine neurotransmission." J Pharm Pharmacol. 1985;37(9):648-650.
B. Holmstedt JEL, T. Plowman, L. Rivier, R. E. Schultes and O. Tovar. "Indole Alkaloids in Amazonian Myristicaceae: Field and Laboratory Research." Botanical Museum Leaflets, Harvard University, vol. 28, No. 3 (Sep. 1980), pp. 215-234.
Backus LI, Sharp T, Grahame-Smith DG. "Behavioural evidence for a functional interaction between central 5-HT2 and 5-HT1A receptors." Br J Pharmacol. 1990;100(4):793-799.
Barker SA, Littlefield-Chabaud MA, David C. "Distribution of the hallucinogens N,N-dimethyltryptamine and 5-methoxy-N,N-dimethyltryptamine in rat brain following intraperitoneal injection: application of a new solid-phase extraction LC-APcI-MS-MS-isotope dilution method." Journal of Chromatography B: Biomedical Sciences and Applications. Journal of Chromatography B, 2001;751(1):37-47.
Barker SA, McIlhenny EH, Strassman R. "A critical review of reports of endogenous psychedelic N, N-dimethyltryptamines in humans: 1955-2010." Drug Test Anal. 2012;4(7-8):617-635.
Barrett FS, Bradstreet MP, Leoutsakos JS, Johnson MW, Griffiths RR. "The Challenging Experience Questionnaire: Characterization of challenging experiences with psilocybin mushrooms." J Psychopharmacol. 2016;30(12):1279-1295.
Barrett FS, Johnson MW, Griffiths RR. "Validation of the revised Mystical Experience Questionnaire in experimental sessions with psilocybin." J Psychopharmacol. 2015;29(11):1182-1190.
Barsuglia DJ. "The Variations of 5-MeO-DMT Mystical Experiences and Considerations for the Future." Paper presented at: World Bufo Alvarius Congress, 2018.
Barsuglia J, Davis AK, Palmer R, Lancelotta R, Windham-Herman AM, Peterson K, Polanco M, Grant R, Griffiths RR. "Intensity of Mystical Experiences Occasioned by 5-MeO-DMT and Comparison With a Prior Psilocybin Study." Front Psychol. 2018;9:2459.
Barsuglia JP, Polanco M, Palmer R, Malcolm BJ, Kelmendi B, Calvey T. "A case report SPECT study and theoretical rationale for the sequential administration of ibogaine and 5-MeO-DMT in the treatment of alcohol use disorder." Prog Brain Res. 2018;242:121-158.
Baxter C, Slaytor M. "Biosynthesis and turnover of N,N-dimethyltryptamine and 5-methoxy-N,N-dimethyltryptamine in Phalaris tuberosa." Phytochemistry. 1972;11(9):2767-2773.
Behar J, Biancani P. "Neural control of the sphincter of Oddi. A physiological role of 5-hydroxytryptamine in the regulation of basal sphincter of Oddi motor activity in the cat." J Clin Invest. 1983;72(2):551-559.
Benington F, Morin, R. D., & Clark Jr, L. C., "5-methoxy-N, N-dimethyltryptamine, a possible endogenous psychotoxin." The Alabama journal of medical sciences. 1965;2(4):397-403.
Berge O-g, Chacho D, Hole K. "Inhibitory effect of 5-methoxy-N,N-dimethyltryptamine on the synaptosomal uptake of 5-hydroxytryptamine." European Journal of Pharmacology. 1983;90(2-3):293-296.
Berger G, Maziere M, Marazano C, Comar D. "Carbon 11 labeling of the psychoactive drug o-methyl-bufotenine and its distribution in the animal organism." Eur J Nucl Med. 1978;3(2):101-104.
Blinderman CD. "Psycho-existential distress in cancer patients: A return to "entheogens"." J Psychopharmacol. 2016;30(12):1205-1206.
Bogenschutz MP, Ross S. "Therapeutic Applications of Classic Hallucinogens." Curr Top Behav Neurosci. 2017.
Bourke CA, Carrigan MJ, Dixon RJ. "Experimental evidence that tryptamine alkaloids do not cause Phalaris aquatica sudden death syndrome in sheep." Aust Vet J. 1988;65(7):218-220.
Bouso JC, Doblin R, Farre M, Alcazar MA, Gomez-Jarabo G. "MDMA-assisted psychotherapy using low doses in a small sample of women with chronic posttraumatic stress disorder." J Psychoactive Drugs. 2008;40(3):225-236.
Bouso JC, Gonzalez D, Fondevila S, Cutchet M, Fernandez X, Ribeiro Barbosa PC, Alcazar-Corcoles MA, Araujo WS, Barbanoj MJ, Fabregas JM, Riba J. "Personality, psychopathology, life attitudes and neuropsychological performance among ritual users of Ayahuasca: a longitudinal study." PLoS One. 2012;7(8):e42421.
Bradley PB, Briggs I. "Further studies on the mode of action of psychotomimetic drugs: antagonism of the excitatory actions of 5-hydroxytryptamine by methylated derivatives of tryptamine." Br J Pharmacol. 1974;50(3):345-354.
Brandt SD, Martins CPB. "Analytical methods for psychoactive N,N-dialkylated tryptamines." TrAC Trends in Analytical Chemistry. 2010;29(8):858-869.
Brierley DI, Davidson C. "Developments in harmine pharmacology—implications for ayahuasca use and drug-dependence treatment." Prog Neuropsychopharmacol Biol Psychiatry. 2012;39(2):263-272.
Brown RT, Nicholas CR, Cozzi NV, Gassman MC, Cooper KM, Muller D, Thomas CD, Hetzel SJ, Henriquez KM, Ribaudo AS, Hutson PR. "Pharmacokinetics of Escalating Doses of Oral Psilocybin in Healthy Adults." Clin Pharmacokinet. 2017;56(12):1543-1554.

(56) References Cited

OTHER PUBLICATIONS

Brown T, Shao W, Ayub S, Chong D, Cornelius C. "A Physician's Attempt to Self-Medicate Bipolar Depression with N,N-Dimethyltryptamine (DMT)." J Psychoactive Drugs. 2017;49(4):294-296.
Bruno R, Matthews AJ, Dunn M, Alati R, McIlwraith F, Hickey S, Burns L, Sindicich N. "Emerging psychoactive substance use among regular ecstasy users in Australia." Drug Alcohol Depend. 2012;124(1-2):19-25.
Brush DE, Bird SB, Boyer EW. "Monoamine Oxidase Inhibitor Poisoning Resulting from Internet Misinformation on Illicit Substances." Journal of Toxicology: Clinical Toxicology. 2004;42(2):191-195.
Callaway JC, Grob CS, McKenna DJ, Nichols DE, Shulgin A, Tupper KW. "A demand for clarity regarding a case report on the ingestion of 5-methoxy-N, N-dimethyltryptamine (5-MeO-DMT) in an Ayahuasca preparation." J Anal Toxicol. 2006;30(6):406-407; author reply 407.
Callaway JC, McKenna DJ, Grob CS, Brito GS, Raymon LP, Poland RE, Andrade EN, Andrade EO, Mash DC. "Pharmacokinetics of Hoasca alkaloids in healthy humans." Journal of Ethnopharmacology. 1999;65(3):243-256.
Callaway JC, Raymon LP, Hearn WL, McKenna DJ, Grob CS, Brito GS, Mash DC. Quantitation of N,N-Dimethyltryptamine and Harmala Alkaloids in Human Plasma after Oral Dosing with Ayahuasca. Journal of Analytical Toxicology. 1996;20(6):492-497.
Cancela LM, Volosin M, Molina VA. "Gangliosides attenuate stress-induced changes on body weight, motor activity and on the behavioral response to 5-methoxy-N,N-dimethyltryptamine." Brain Research Bulletin. 1996;40(2):105-110.
Carbonaro TM, Bradstreet MP, Barrett FS, MacLean KA, Jesse R, Johnson MW, Griffiths RR. "Survey study of challenging experiences after ingesting psilocybin mushrooms: Acute and enduring positive and negative consequences." J Psychopharmacol. 2016;30(12):1268-1278.
Cardenas CG, Del Mar LP, Cooper BY, Scroggs RS. "5HT4Receptors Couple Positively to Tetrodotoxin-Insensitive Sodium Channels in a Subpopulation of Capsaicin-Sensitive Rat Sensory Neurons." The Journal of Neuroscience. 1997;17(19):7181-7189.
Carhart-Harris R, Nutt D. "Was it a vision or a waking dream?" Front Psychol. 2014;5:255.
Carhart-Harris RL, Bolstridge M, Day CMJ, Rucker J, Watts R, Erritzoe DE, Kaelen M, Giribaldi B, Bloomfield M, Pilling S, Rickard JA, Forbes B, Feilding A, Taylor D, Curran HV, Nutt DJ. "Psilocybin with psychological support for treatment-resistant depression: six-month follow-up." Psychopharmacology (Berl). 2018;235(2):399-408.
Carhart-Harris RL, Bolstridge M, Rucker J, Day CMJ, Erritzoe D, Kaelen M, Bloomfield M, Rickard JA, Forbes B, Feilding A, Taylor D, Pilling S, Curran VH, Nutt DJ. "Psilocybin with psychological support for treatment-resistant depression: an open-label feasibility study." The Lancet Psychiatry. 2016;3(7):619-627.
Carhart-Harris RL, Erritzoe D, Haijen E, Kaelen M, Watts R. "Psychedelics and connectedness." Psychopharmacology (Berl). 2018;235(2):547-550.
Carhart-Harris RL, Erritzoe D, Williams T, Stone JM, Reed LJ, Colasanti A, Tyacke RJ, Leech R, Malizia AL, Murphy K, Hobden P, Evans J, Feilding A, Wise RG, Nutt DJ. "Neural correlates of the psychedelic state as determined by fMRI studies with psilocybin." Proc Natl Acad Sci U S A. 2012;109(6):2138-2143.
Carhart-Harris RL, Goodwin GM. "The Therapeutic Potential of Psychedelic Drugs: Past, Present, and Future." Neuropsychopharmacology. 2017;42(11):2105-2113.
Carhart-Harris RL, Kaelen M, Bolstridge M, Williams TM, Williams LT, Underwood R, Feilding A, Nutt DJ. "The paradoxical psychological effects of lysergic acid diethylamide (LSD)." Psychol Med. 2016;46(7):1379-1390.
Carhart-Harris RL, Leech R, Hellyer PJ, Shanahan M, Feilding A, Tagliazucchi E, Chialvo DR, Nutt D. "The entropic brain: a theory of conscious states informed by neuroimaging research with psychedelic drugs." Front Hum Neurosci. 2014;8:20.
Carhart-Harris RL, Leech R, Williams TM, Erritzoe D, Abbasi N, Bargiotas T, Hobden P, Sharp DJ, Evans J, Feilding A, Wise RG, Nutt DJ. "Implications for psychedelic-assisted psychotherapy: functional magnetic resonance imaging study with psilocybin." Br J Psychiatry. 2012;200(3):238-244.
Carhart-Harris RL, Muthukumaraswamy S, Roseman L, Kaelen M, Droog W, Murphy K, Tagliazucchi E, Schenberg EE, Nest T, Orban C, Leech R, Williams LT, Williams TM, Bolstridge M, Sessa B, McGonigle J, Sereno MI, Nichols D, Hellyer PJ, Hobden P, Evans J, Singh KD, Wise RG, Curran HV, Feilding A, Nutt DJ. "Neural correlates of the LSD experience revealed by multimodal neuroimaging." Proc Natl Acad Sci U S A. 2016;113(17):4853-4858.
Carhart-Harris RL, Nutt DJ. "Serotonin and brain function: a tale of two receptors." J Psychopharmacol. 2017;31(9):1091-1120.
Carhart-Harris RL, Roseman L, Bolstridge M, Demetriou L, Pannekoek JN, Wall MB, Tanner M, Kaelen M, McGonigle J, Murphy K, Leech R, Curran HV, Nutt DJ. "Psilocybin for treatment-resistant depression: fMRI-measured brain mechanisms." Sci Rep. 2017;7(1):13187.
CheckIt! 5-MeO-DMT www.checkyourdrugs.at Summary; 2017.
Chemical C. 5-MeO-DMT Safety Data Sheet; 2015.
Chen BH, Liu JT, Chen WX, Chen HM, Lin CH. "A general approach to the screening and confirmation of tryptamines and phenethylamines by mass spectral fragmentation." Talanta. 2008;74(4):512-517.
Commissaris RL, Davis M. "Opposite effects of N,N-dimethyltryptamine (DMT) and 5-methoxy-N,N-dimethyltryptamine (5-MeODMT) on acoustic startle: Spinal vs brain sites of action." Neuroscience & Biobehavioral Reviews. 1982;6(4):515-520.
Office Action issued in CN 202080030317.3 (WO2020/169850), dated Aug. 15, 2024, translation.
Corrected Notice of Allowability issued in U.S. Appl. No. 18/604,747 dated Sep. 11, 2024 (pages reflecting non-considered IDS omitted for brevity).
European Search Report on EP4431494 (WO2020254584) dated Aug. 16, 2024.
European Search Opinion on EP4431494 (WO2020254584) dated Aug. 16, 2024.
European Search Strategy on EP4431494 (WO2020254584) dated Aug. 16, 2024.
Preller et al., Effective connectivity changes in LSD-induced altered states of consciousness in humans, Proceedings of the National Academy of Sciences, 2019, 116(7): 2743-2748.
Hutten et al., Inter-individual variability in neural response to low doses of LSD, Transl Psychiatry, 2024, 14(1): 288, doi: 10.1038/s41398-024-03013-8.
Yaden et al., Clinically relevant acute subjective effects of psychedelics beyond mystical experience, Nature Reviews Psychology, 2024, doi: 10.1038/s44159-024-00345-6.
Holze et al., Serotonergic Psychedelics: A Comparative Review of Efficacy, Safety, Pharmacokinetics, and Binding Profile, Biological Psychiatry: CNNI, 2024, 9: 472-489, doi: 10.1016/j.bpsc.2024.01.007.
Luan et al., Psychological and physiological effects of extended DMT, Journal of Psychopharmacology, 2024, 38(1): 56-67.
Palhano-Fontes et al., Rapid antidepressant effects of the psychedelic ayahuasca in treatment-resistant depression: a randomized placebo-controlled trial, Psychological Medicine, 2018, 49: 655-663.
Preller et al., The Fabric of Meaning and Subjective Effects in LSD-Induced States Depend on Serotonin 2A Receptor Activation, Current Biology, 2017, 27: 451-457.
Copa et al., Predicting the outcome of psilocybin treatment for depression from baseline fMRI functional connectivity, J Affect Disord, 2024, 353: 60-69, doi: 10.1016/j.jad.2024.02.089.
Siegel et al., Psilocybin desynchronizes the human brain, Nature, 2024, 632(8023):131-138, 10.1038/s41586-024-07624-5.
R. Corne et al., "Neurotrophic mechanisms of psychedelic therapy," Biol Aujourd'hui, 2019, 2013(3-4): 121-129.
G. P. Schmitz et al., "5-HT2A SNPs Alter the Pharmacological Signaling of Potentially Therapeutic Psychedelics," ACS Chem Neurosci, 2022, 13 (16): 2386-2398.

(56) References Cited

OTHER PUBLICATIONS

L. P. Cameron et al., "5-HT2ARs Mediate Therapeutic Behavioral Effects of Psychedelic Tryptamines," ACS chemical neuroscience vol. 14,3 (2023): 351-358. doi: 10.1021/acschemneuro.2c00718.
C. Chemical, "5-hydroxy DMT (hydrochloride) Product Information," 2020.
5meoDMT.org, "5-MeO-DMT : HCL to FB Conversion Method for Optimization of Yield," 2018.
A. Ragnhildstveit et al., "5-MeO-DMT for post-traumatic stress disorder: a real-world longitudinal case study," Frontiers in Psychiatry, vol. 14, Nov. 23, 2023, doi:10.3389/fpsyt.2023.1271152.
R. Lancelotta, "5-MeO-DMT has not been found in traditional ayahuasca preparations and the combination of 5-MeO-DMT with MAOIs is dangerous," Hum Psychopharmacol, vp/. 37(3): e2839, doi: 10.1002/hup.2839.
S. J. Jefferson et al., "5-MeO-DMT modifies innate behaviors and promotes structural neural plasticity in mice," bioRxiv, 2022.11.03. 515044, doi; 10.1101/2022.11.03.515044.
B. Bauer, "5-MeO-DMT, Toad Secretions, and the Entourage Effect," Psychedelic Science Review, 2019.
R. Fuentes, "5-Meo-DMT/ N, N-DMT for Addiction Treatment" 2021.
T. Conclave, "5-MEO-DMT: A Recommended Model for Best Practices" 2018.
H. M. Dourron et al., "5-MeO-DMT: An atypical psychedelic with unique pharmacology, phenomenology & risk?" Psychopharmacology (Berl), 2023, doi: 10.1007/s00213-023-06517-1.
D. Bank, "5-methoxy-N,N-dimethyltryptamine," 2018.
C. B. Germann, "5-methoxy-N,N-dimethyltryptamine: An ego-dissolving endogenous neurochemical catalyst of creativity," 2019, doi: 10.1101/578435.
T.T. Wave, 9 Things You Need to Know About 5-MeO-DMT, 2018.
J. Haarsma et al., "A continuum hypothesis of psychotomimetic rapid antidepressants," Brain Neurosci Adv, 2021, doi: 10.1177/23982128211007772.
N. K. Savalia et al., "A Dendrite-Focused Framework for Understanding the Actions of Ketamine and Psychedelics," Trends Neurosci, 2021, vol. 44(4): 260-275.
A. O. Ermakov et al., "A narrative synthesis of research with 5-MeO-DMT," J Psychopharmacol, 2021, doi: 10.1177/02698811211050543.
L. P. Cameron et al., "A non-hallucinogenic psychedelic analogue with therapeutic potential," Nature, 2021, vol. 589(7842):474-479, doi: 10.1038/s41586-020-3008-z.
F. G. Sleight et al., "A novel ego dissolution scale: A construct validation study," Conscious Cogn, 2023, vol. 109, doi: 10.1016/j.concog.2023.103474.
J. Reckweg et al., "A Phase 1, Dose-Ranging Study to Assess Safety and Psychoactive Effects of a Vaporized 5-Methoxy-N, N-Dimethyltryptamine Formulation (GH001) in Healthy Volunteers," Frontiers in Pharmacology, 2021, vol. 12, doi: 10.3389/fphar.2021.760671.
J. T. Reckweg et al., "A phase ½ trial to assess safety and efficacy of a vaporized 5-methoxy-N,N-dimethyltryptamine formulation (GH001) in patients with treatment-resistant depression," Frontiers in Psychiatry, 2023, vol. 14, doi: 10.3389/fpsyt.2023.1133414.
R. B. Sauras Quetcuti, "A psychotic episode after ayahuasca and secretion of Bufo Alvarius toad consumption: A case report," 2021.
J. J. Palamar, et al., "A qualitative descriptive analysis of effects of psychedelic phenethylamines and tryptamines," Human Psychopharmacology: Clinical and Experimental, 2020, vol. 35(1): e2719.
S. N. Calderon et al., "A regulatory perspective on the evaluation of hallucinogen drugs for human use," Neuropharmacology,2018, vol. 142: 135-142, doi: 10.1016/j.neuropharm.2017.11.028.
J. H. Halpern et al., "A Review of Hallucinogen Persisting Perception Disorder (HPPD) and an Exploratory Study of Subjects Claiming Symptoms of HPPD," Curr Top Behav Neurosci, 2018, vol. 36: 333-360, doi: 10.1007/7854_2016_457.
T. Froese et al., "A role for enhanced functions of sleep in psychedelic therapy?" Adaptive Behavior, 2018, vol. 26(3): 129-135.
H. Vargas-Perez et al., "A single administration of the hallucinogen, 4-acetoxy-dimethyltryptamine, prevents the shift to a drug-dependent state and the expression of withdrawal aversions in rodents," Eur J Neurosci, vol. 45(11): 1410-1417.
R. V. Lima da Cruz , "A Single Dose of 5-MeO-DMT Stimulates Adult Neurogenesis in Mouse Dentate Gyrus," 2018.
F. Holze et al., "Acute dose-dependent effects of lysergic acid diethylamide in a double-blind placebo-controlled study in healthy subjects," Neuropsychopharmacology, 2021, vol. 46(3): 537-544, doi: 10.1038/s41386-020-00883-6.
S. B. Vogt et al., Acute effects of intravenous DMT in a randomized placebo-controlled study in healthy participants, 2023, Transl Psychiatry, vol. 13(1):172, doi: 10.1038/s41398-023-02477-4.
A. M. Becker et al., "Acute Effects of Psilocybin After Escitalopram or Placebo Pretreatment in a Randomized, Double-Blind, Placebo-Controlled, Crossover Study in Healthy Subjects," Clin Pharmacol Ther, 2022, vol. 111(4):886-895, doi: 10.1002/cpt.2487.
P. Caliceti et al., "Advances in Drug Delivery and Biomaterials: Facts and Vision," Pharmaceutics, 2019, vol. 11(1), doi: 10.3390/pharmaceutics11010048.
J. J. Breeksema et al., "Adverse events in clinical treatments with serotonergic psychedelics and MDMA: A mixed-methods systematic review," J Psychopharmacol, 2022, doi: 10.1177/02698811221116926.
E. Dakwar, "Amphibious anti-depressants and other wonders," Am J Drug Alcohol Abuse, 2019, vol. 45(2):115-116, doi 10.1080/00952990.2019.1580288.
J. Lu, "An analog of psychedelics restores functional neural circuits disrupted by unpredictable stress," Mol Psychiatry, 2021, vol. 26(11): 6237-6252, doi: 10.1038/s41380-021-01159-1.
Zamnesia, "An Interview With Octavio Rettig," 2018.
T. Calvey et al., "An introduction to psychedelic neuroscience," Prog Brain Res, 2018, vol. 242: 1-23, doi: 10.1016/bs.pbr.2018.09.013.
S. Pharmacist, "Antidepressant & Psychedelic Drug Interaction Chart," 2021.
S. Pharmacist, "Antidepressant and Psychedelic Combinations: A Guide to Risks & Discontinuation Times," 2019.
V. A. Nygart et al., "Antidepressant effects of a psychedelic experience in a large prospective naturalistic sample," J Psychopharmacol, 2022, vol. 36(8): 932-942, doi: 10.1177/02698811221101061.
M. G. da Silva et al., "Anti-inflammatory activity of ayahuasca: therapeutical implications in neurological and psychiatric diseases," Behav Brain Res, 2021, vol. 400, doi: 10.1016/j.bbr.2020.113003.
J. Winne et al., "Anxiety-like behavior induced by salicylate depends on age and can be prevented by a single dose of 5-MeO-DMT," Exp Neurol, 2020, vol. 326, doi: 10.1016/j.expneurol.2020.113175.
A. K. Louie et al., "Are Psychedelics Something New in Teaching Psychopharmacology?" Acad Psychiatry, 2020, doi: 10.1007/s40596-020-01294-x.
F. Sampedro et al., "Assessing the Psychedelic After-Glow" in Ayahuasca Users: Post-Acute Neurometabolic and Functional Connectivity Changes Are Associated with Enhanced Mindfulness Capacities, Int J Neuropsychopharmacol,2017, vol. 20(9):698-711, doi: 10.1093/ijnp/pyx036.
N. Gukasyan et al., "Attenuation of psilocybin mushroom effects during and after SSRI/SNRI antidepressant use," J Psychopharmacol, 2023, doi: 10.1177/02698811231179910.
P. S. Hendricks, "Awe: a putative mechanism underlying the effects of classic psychedelic-assisted psychotherapy," Int Rev Psychiatry, 2018, vol. 30(4): 331-342, doi: 10.1080/09540261.2018.1474185.
J. Goncalves et al., Ayahuasca Beverages: Phytochemical Analysis and Biological Properties, Antibiotics (Basel), 2020, vol. 9(11), doi:10.3390/antibiotics9110731.
J. C. Callaway et al., Ayahuasca preparations and serotonin reuptake inhibitors: a potential combination for severe adverse interactions, J Psychoactive Drugs, 1998, vol. 30(4): 367-9, doi: 10.1080/02791072.1998.10399712.
H. Kaasik et al., Ayahuasca Users in Estonia: Ceremonial Practices, Subjective Long-Term Effects, Mental Health, and Quality of Life, J Psychoactive Drugs, 2020, vol. 52(3): 255-263, doi: 10.1080/02791072.2020.1748773.

(56) References Cited

OTHER PUBLICATIONS

L. P. Cameron et al., Beyond the 5-HT(2A) Receptor: Classic and Nonclassic Targets in Psychedelic Drug Action, J Neurosci, 2023, vol. 43(45): 7472-7482, doi: 10.1523/JNEUROSCI.1384-23.2023.
H. Vigerelli et al., Biological Effects and Biodistribution of Bufotenine on Mice, Biomed Res Int, 2018, doi: 10.1155/2018/1032638.
J. G. Dean et al., Biosynthesis and Extracellular Concentrations of N,N-dimethyltryptamine (DMT) in Mammalian Brain, Sci Rep, 2019, vol. 9(1): 9333,, doi: 10.1038/s41598-019-45812-w.
Office Action issued in CR2021-000437 (WO2020/169850), dated Nov. 18, 2024, translation.
Office Action issued in BZ 1021.21 (WO2020/169851), dated Nov. 11, 2024.
Third party observation filed in EP4373807 (WO2023002005), dated Nov. 27, 2024.
Notice of Opposition filed in EP4313945 (WO2023186834) dated Dec. 4, 2024.
Decision T0777/08 of the Boards of Appeal of the European Patent Office, May 24, 2011.
Otto, "X-Ray Powder Diffraction: Why Not Use CuKβ Radiation?" Journal of Analytical Sciences Methods and Instrumentation, Sep. 12, 2018, vol. 8, pp. 37-47.
Byrn, "Pharmaceutical Solids: A Strategic Approach to Regulatory Considerations," Pharmaceutical Research, vol. 12, No. 7, 1995.
Tetrahydrofuran, Wikipedia, https://web.archive.Org/web/20210503064409/https://en.wikipedia.org/wiki/Tetrahydrofuran, Archived version of how the webpage appeared on May 3, 2021.
Repke et al., Psilocin analogs. 1. Synthesis of 3[2(dialkylamino)ethyl] and 3[2(cycloalkylamino)ethyl] indol4ols, Journal of Heterocyclic Chemistry, 1977, 14: 71-74.
Poon et al., Synthesis of psilocin labelled with 14C and 3H, Journal of Labelled Compounds and Radiopharmaceuticals, 1986, vol. 23, No. 2, pp. 167-174.
Nichols et al., Improvements to the Synthesis of Psilocybin and a Facile Method for Preparing the O-Acetyl Prodrug of Psilocin, Synthesis, 1999 (06):935-938.
Kargbo et al., Direct Phosphorylation of Psilocin Enables Optimized cGMP Kilogram-Scale Manufacture of Psilocybin, ACS Omega, 2020, 5, 27, 16959-16966.
Sherwood et al., An Improved, Practical, and Scalable Five-Step Synthesis of Psilocybin Synthesis, Synthesis, 2020; 52(05): 688-694.
Speeter-Anthony, The Action of Oxalyl Chloride on Indoles a New Approach to Tryptamines, J. Am. Chem. Soc., 1954, 76, 23, 6208-6210.
Xu et al., Synthesis of deuterium labeled standards of 5-methoxy-N,N-dimethyltryptamine (5-MeO-DMT), J Label Compd. Radiopharm, 2006, vol. 49, Issue 10, pp. 897-902.
Rochester, Solvents and Polarity, https://web.archive.Org/web/20210302032809/https://www.chem.rochester.edu/notvoodoo/pages/reagents.php?page=solvent_polarity, Archived version of how the webpage appeared on Mar. 2, 2021.
Methyl tert-butyl ether, Wikipedia, https://web.archive.Org/web/20210514020733/https://en.wikipedia.org/wiki/Methyl_tert-butyl_ether, Archived version of how the webpage appeared on May 14, 2021.
K. P. Kuypers et al., Microdosing psychedelics: More questions than answers? An overview and suggestions for future research, J Psychopharmacol, 2019, vol. 33(9): 1039-1057, doi: 10.1177/0269881119857204.
T. Conclave, Mission, Vision, Commitments and Agreements, 2018.
R. N. de Almeida et al., Modulation of Serum Brain-Derived Neurotrophic Factor by a Single Dose of Ayahuasca: Observation From a Randomized Controlled Trial, Front Psychol, 2019, vol. 10: 1234, doi: 10.3389/fpsyg.2019.01234.
P. Cumming et al., Molecular and Functional Imaging Studies of Psychedelic Drug Action in Animals and Humans, Molecules, 2021, vol. 26(9).
R. Sutherland et al., Motivations for new psychoactive substance use among regular psychostimulant users in Australia, Int J Drug Policy, 2017, vol. 43: 23-32, doi: 10.1016/j.drugpo.2016.12.021.
MSDS Online Search Results 5-MeO-DMT, 2018.
F. Kummrow, Mutagenicity of Ayahuasca and Their Constituents to the *Salmonella*/Microsome Assay, Environ Mol Mutagen, 2019, vol. 60(3): 269-276, doi: 10.1002/em.22263.
S. A. Barker, N, N-Dimethyltryptamine (DMT), an Endogenous Hallucinogen: Past, Present, and Future Research to Determine Its Role and Function, Front Neurosci, 2018, vol. 12: 536, doi: 10.3389/fnins.2018.00536.
E. Eckernas et al., N,N-dimethyltryptamine affects EEG response in a concentration dependent manner—a pharmacokinetic/pharmacodynamic analysis, CPT Pharmacometrics Syst Pharmacol, 2023.
C. Pallavicini et al., Neural and subjective effects of inhaled N,N-dimethyltryptamine in natural settings, J Psychopharmacol, 2021, doi: 10.1177/0269881120981384.
C. Timmermann et al., Neural correlates of the DMT experience assessed with multivariate EEG, Sci Rep, 2019, vol. 9(1):16324, doi: 10.1038/s41598-019-51974-4.
E. A. Schindler et al., Neuroendocrine associations underlying the persistent therapeutic effects of classic serotonergic psychedelics, Frontiers in pharmacology, 2018, vol. 9: 177.
L. Rodriguez et al., New Insights into the Chemical Composition of Ayahuasca, ACS Omega, 2022, vol. 7(14): 12307-12317, doi: 10.1021/acsomega.2c00795.
F. Schifano et al., New psychoactive substances (NPS) and serotonin syndrome onset: A systematic review, Exp Neurol, 2021, vol. 339, doi: 10.1016/j.expneurol.2021.113638.
N. Allen et al., "Non-Peer-reviewed—LSD increases sleep duration the night after microdosing," medRxiv, 2023, https://doi.org/10.1101/2023.06.27.23291970.
OmTerra, OmTerra Psychedelic Therapy Education, Advocacy and Outreach, The Midwest Psychedelic Therapy Symposium, 2018.
P. J. Vis et al., On Perception and Consciousness in HPPD: A Systematic Review, Front Neurosci, 2021, vol. 15, doi: 10.3389/fnins.2021.675768.
A. K. Davis et al., Open-label study of consecutive ibogaine and 5-MeO-DMT assisted-therapy for trauma-exposed male Special Operations Forces Veterans: prospective data from a clinical program in Mexico, The American Journal of Drug and Alcohol Abuse, 2023, vol. 49(5): 587-596.
OPIS, OPIS policy paper calls for legalisation of psilocybin for treatment of cluster headaches, 2020.
E. Eckernäs et al., Optimized infusion rates for N,N-dimethyltryptamine to achieve a target psychedelic intensity based on a modeling and simulation framework, CPT Pharmacometrics Syst Pharmacol, 2023, doi: 10.1002/psp4.13037.
D. A. Dornbierer et al., Overcoming the clinical challenges of traditional ayahuasca: a first-in-human trial exploring novel routes of administration of N,N-Dimethyltryptamine and harmine, Front Pharmacol, 2023, vol. 14, doi: 10.3389/fphar.2023.1246892.
A. Garcia-Romeu et al., Persisting Reductions in Cannabis, Opioid, and Stimulant Misuse After Naturalistic Psychedelic Use: An Online Survey, Front Psychiatry, 2019, vol. 10: 955, doi: 10.3389/fpsyt.2019.00955.
C. Grumann et al., Pharmacokinetics and subjective effects of 1P-LSD in humans after oral and intravenous administration, Drug Test Anal, 2020, vol. 12(8): 1144-1153, doi: 10.1002/dta.2821.
M. Good et al., Pharmacokinetics of DMT Fumarte in Humans, 2022, doi: 10.22541/au.165237523.39763980/v1.
M. Good et al., Pharmacokinetics of N,N-dimethyltryptamine in Humans, Eur J Drug Metab Pharmacokinet, 2023, p. 1-17, doi: 10.1007/s13318-023-00822-y.
D. W. Lawrence et al., Phenomenology and content of the inhaled N, N-dimethyltryptamine (N, N-DMT) experience, Sci Rep, 2022, vol. 12(1): 8562, doi: 10.1038/s41598-022-11999-8.
E. Eckernas et al., Population pharmacokinetic/pharmacodynamic modelling of the psychedelic experience induced by N,N-dimethyltryptamine—implications for dose considerations, Clin Transl Sci, 2022, doi: 10.1111/cts.13410.

(56) References Cited

OTHER PUBLICATIONS

J. D. Sexton et al., Population Survey Data Informing the Therapeutic Potential of Classic and Novel Phenethylamine, Tryptamine, and Lysergamide Psychedelics, Front Psychiatry, 2019, vol. 10: 896, doi: 10.3389/fpsyt.2019.00896.
R. R., Porn actor Nacho Vidal, arrested for the death of a photographer in a ritual with poison toad, El Espanol, 2020.
M. J. Spriggs et al., Positive effects of psychedelics on depression and wellbeing scores in individuals reporting an eating disorder, Eat Weight Disord, 2021, vol. 26(4): 1265-1270, doi: 10.1007/s40519-020-01000-8.
C. Jairaj et al., "Postpartum depression: A role for psychedelics?" J Psychopharmacol, 2022, vol. 36(8): 920-931, doi: 10.1177/02698811221093793.
R. J. Zeifman et al., Post-Psychedelic Reductions in Experiential Avoidance Are Associated With Decreases in Depression Severity and Suicidal Ideation, Front Psychiatry, 2020, vol. 11: 782, doi: 10.3389/fpsyt.2020.00782.
H. D. Aicher et al., Potential therapeutic effects of an ayahuasca-inspired N,N-DMT and harmine formulation: a controlled trial in healthy subjects, Front Psychiatry, 2023, vol. 14, doi: 10.3389/fpsyt.2023.1302559.
P. G. Johnstad, Powerful substances in tiny amounts: An interview study of psychedelic microdosing, Nordisk Alkohol Nark, 2018, vol. 35(1): 39-51, doi: 10.1177/1455072517753339.
K. Ko et al., Predicting the Intensity of Psychedelic-Induced Mystical and Challenging Experience in a Healthy Population: An Exploratory Post-Hoc Analysis, Neuropsychiatric Disease and Treatment, 2023, vol. 19: 2105-2113, doi: 10.2147/ndt.S426193.
O. Simonsson et al., Prevalence and associations of classic psychedelic-related seizures in a population-based sample, Drug Alcohol Depend, 2022, vol. 239, doi: 10.1016/j.drugalcdep.2022.109586.
Sterling, Proposal for the physical characterisation of 5-Methoxy-N,N-dimethyltryptamine (5-MeODMT), 2020.
S. B. Armstrong, Prospective associations of psychedelic treatment for co-occurring alcohol misuse and posttraumatic stress symptoms among United States Special Operations Forces Veterans, Mil Psychol, 2024, vol. 36(2): 184-191 doi: 10.1080/08995605.2022.2156200.
C. W. Thomas et al., Psilocin acutely alters sleep-wake architecture and cortical brain activity in laboratory mice, Transl Psychiatry, 2022, vol. 12(1): 77, doi: 10.1038/s41398-022-01846-9.
C. I. V. Bird et al., Psilocybin and MDMA for the treatment of trauma-related psychopathology, Int Rev Psychiatry, 2021, vol. 33(3): 229-249, doi: 10.1080/09540261.2021.1919062.
Psilocybin as a Novel Pharmacotherapy for Treatment-Refractory Anorexia Nervosa, OBM Neurobiology, 2021, vol. 05(02): 1-1, doi: 10.21926/obm.neurobiol.2102102.
R. L. Carhart-Harris et al., Psilocybin for treatment-resistant depression: fMRI-measured brain mechanisms, Sci Rep, 2017, vol. 7(1): 13187, doi: 10.1038/s41598-017-13282-7.
N. L. Mason et al., Psilocybin induces acute and persisting alterations in immune status in healthy volunteers: An experimental, placebo-controlled study, Brain Behav Immun, 2023, vol. 114: 299-310, doi: 10.1016/j.bbi.2023.09.004.
K. H. Preller et al., Psilocybin Induces Time-Dependent Changes in Global Functional Connectivity, Biol Psychiatry, 2020, vol. 88(2): 197-207, doi: 10.1016/j.biopsych.2019.12.027.
O. Jefsen et al., Psilocybin lacks antidepressant-like effect in the Flinders Sensitive Line rat, Acta Neuropsychiatr, 2019, vol. 31(4): 213-219, doi: 10.1017/neu.2019.15.
J. Marschall et al., Psilocybin microdosing does not affect emotion-related symptoms and processing: A preregistered field and lab-based study, J Psychopharmacol, 2022, vol. 36(1): 97-113, doi: 10.1177/02698811211050556.
E. James et al., Psilocybin occasioned mystical-type experiences, Hum Psychopharmacol, 2020, vol. 35(5): e2742, doi: 10.1002/hup.2742.
C. T. Golden et al., Psilocybin reduces low frequency oscillatory power and neuronal phase-locking in the anterior cingulate cortex of awake rodents, Sci Rep, 2022, vol. 12(1): 12702, doi: 10.1038/s41598-022-16325-w.
R. B. Kargbo, Psilocybin Therapeutic Research: The Present and Future Paradigm, ACS Med Chem Lett, 2020, vol. 11(4):399-402, doi: 10.1021/acsmedchemlett.0c00048.
M. K. Doss et al., Psilocybin therapy increases cognitive and neural flexibility in patients with major depressive disorder, Transl Psychiatry, 2021, vol. 11(1): 574, doi: 10.1038/s41398-021-01706-y.
R. Strumila et al., Psilocybin, a Naturally Occurring Indoleamine Compound, Could Be Useful to Prevent Suicidal Behaviors, Pharmaceuticals (Basel), 2021, vol. 14(12), doi: 10.3390/ph14121213.
L. Roseman, Psilocybin-assisted therapy for depression, 2017.
N. M. Rieser et al., Psilocybin-induced changes in cerebral blood flow are associated with acute and baseline inter-individual differences, Sci Rep, 2023, vol. 13(1): 17475, doi: 10.1038/s41598-023-44153-z.
M. Balaet, Psychedelic Cognition—The Unreached Frontier of Psychedelic Science, Front Neurosci, 2022, vol. 16, doi: 10.3389/fnins.2022.832375.
Third Party Submission filed in U.S. Appl. No. 18/675,614, filed Sep. 26, 2024.
Third Party Submission filed in U.S. Appl. No. 18/675,614, filed Sep. 27, 2024.
Third Party Submission filed in U.S. Appl. No. 18/675,614, filed Oct. 16, 2024.
Office Action issued in HN 2021-001978 (WO2020/169850) dated Sep. 4, 2024, translation.
Office Action issued in HN 2021-001979 (WO2020/169851) dated Oct. 8, 2024.
Office Action issued in DOP0008/2021 (WO2020/169851) dated Sep. 9, 2024, translation.
Office Action issued in DOP0009/2021 (WO2020/169850) dated Sep. 9, 2024, translation.
Office Action issued in CO2021/0010882 (WO2020/169850) dated Sep. 12, 2024, translation.
Office Action issued in CO2021/0010883 (WO2020/169851) dated Sep. 12, 2024, translation.
Hermann, Psychiatric Comorbidity in Chronic Epilepsy: Identification, Consequences, and Treatment of Major Depression, Epilepsia, 2005, 41(2):31-41.
Erowid, Cranial Chomping 5-MeO-DMT, 2003, https://erowid.org/experiences/exp.php?ID=26469, Retrieved Jun. 7, 2007.
Mohebbi, Patient centric measures for a patient centric era: Agreement and convergent between ratings on the Patient Global Impression of Improvement (PGI-I) scale and the Clinical Global Impressions—Improvement (CGI-S) scale in bipolar and major depressive disorder, European Psychiatry, 2018, 53:17-22.
Santos, Long-term effects of ayahuasca in patients with recurrent depression: a 5-year qualitative follow-up, Archives of Clinical Psychiatry, 2018, 45(1):22-24.
Muller, Differentiating moderate and severe depression using the Montgomery-Asberg depression rating scale (MADRS), Journal of Affective Disorders, 2003, 77:255-260.
Olin, Mortality and Suicide Risk in Treatment-Resistant Depression: An Observational Study of the Long-Term Impact of Intervention, PLOS One, 2012, 7(10): e48002.
Schifano, New Psychoactive Substances (NPS), Psychedelic Experiences and Dissociation: Clinical and Clinical Pharmacological Issues, Current Addiction Reports, 2019, 6:140-152.
Schenberg, Translation and cultural adaptation of the States of Consciousness Questionnaire (SOCQ) and statistical validation of the Mystical Experience Questionnaire (MEQ30) in Brazilian Portuguese, Archives of Clinical Psychiatry, 2017, 44(1):1-5.
Office Action issued in JP2022-549753 (WO2021/170614), dated Mar. 4, 2025, translation.
Diagnostic and Statistical Manual of Mental Disorders Fifth Edition ("DSM-5"), American Psychiatric Association, 2013, pp. 1-25, 155-188, 271-281.
Letter to the Central Commissie Mensgebonden Onderzoek (CCMO)) dated Jun. 4, 2019 concerning clinical trial GH001-MDD-102.

(56) References Cited

OTHER PUBLICATIONS

Pages 1 and 19 of clinical trial application form dated Jun. 3, 2019 concerning clinical trial GH001-MDD-102.
Letter to the Central Commissie Mensgebonden Onderzoek (CCMO) submitting substantial amendment to Part B of the study dated Oct. 13, 2020 concerning clinical trial GH001-MDD-102.
Pages 1 and 19 of the updated clinical trial application form dated Oct. 20, 2020 concerning clinical trial GH001-MDD-102.
Jan. 2025 version of the EudraCT & EU CTR FAQs.
Dr. Gerardo Sandoval Isaac: 1+ Reviews, Retreats & 2025 Schedule, www.retreat.guru/teachers/756-59/dr-g, retrieved Mar. 4, 2025.
Johnson et al., Classic psychedelics: An integrative review of epidemiology, therapeutics, mystical experience, and brain network function, Pharmacology & Therapeutics, 2018, 197 (2019) 83-102.
GH Research, a Randomized, Double-Blind, Placebo-Controlled, Phase 2b Trial with an Open-Label Extension to Determine the Safety and Efficacy of GH001 in Patients with Treatment-Resistant Depression GH001-TRD-201, 2025.
Goodwin et al., Single-Dose Psilocybin for a Treatment-Resistant Episode of Major Depression, NEJM, 2022, 387(18), 1637.
Supplementary Appendix to Goodwin et al., Single-Dose Psilocybin for a Treatment-Resistant Episode of Major Depression, NEJM, 2022, 387(18), 1637.
Kamal et al., Role of Psychedelics in Treatment-Resistant Depression, Psychiatr Clin North Am, 2023, 46(2): 291-305, doi: 10.1016/j.psc.2023.02.004.
Layzell et al., Discovery and In Vitro Characterization of SPL028: Deuterated N,N-Dimethyltryptamine, ACS Med Chem Lett, 2023, 14(9): 1216-1223, doi: 10.1021/acsmedchemlett.3c00143.
Gumpper et al., The structural diversity of psychedelic drug actions revealed, Nat Commun, 2025, 16(1): 2734, doi: 10.1038/s41467-025-57956-7.
Nutt, Drug development in psychiatry: 50 years of failure and how to resuscitate it, Lancet Psychiatry, 2025, 12(3): 228-238, doi: 10.1016/S2215-0366(24)00370-5.
De Miranda et al., Investigating novel pharmacological strategies for treatment-resistant depression: focus on new mechanisms and approaches, Expert Opin Drug Discov, 2025, pp. 1-15, doi: 10.1080/17460441.2025.2460674.
Hinkle et al., Adverse Events in Studies of Classic Psychedelics: A Systematic Review and Meta-Analysis, JAMA Psychiatry, 2024, 81(12): 1225-1235, doi: 10.1001/jamapsychiatry.2024.2546.
Dickinson, S. L. et al., "The effects of lesions produced by 5,7-dihydroxytryptamine on 5-hydroxytryptamine-mediated behaviour induced by amphetamine in large doses in the rat," Neuropharmacology, 1984;23(4):423-9.
Glennon, R. A. et al., "Evidence for 5-HT2 involvement in the mechanism of action of hallucinogenic agents," *Life Sci*, 1984;35(25):2505-11.
Green, A. R. et al., "The behavioural effects of RU 24969, a suggested 5-HT1 receptor agonist in rodents and the effect on the behaviour of treatment with antidepressants," *Neuropharmacology*, 1984;23(6):655-61.
Larson, A. A., "Acute and chronic effects of LSD and 5-MeODMT on raphe-evoked dorsal root potentials in the cat," *Life Sci*, 1984;34(12):1193-201.
Lucki, I. et al., "Differential actions of serotonin antagonists on two behavioral models of serotonin receptor activation in the rat," *J Pharmacol Exp Ther*, 1984;228(1):133-9.
MacRae, W.D. et al. "Justicia pectoralis: a study of the basis for its use as a hallucinogenic snuff ingredient," *J Ethnopharmacol*, 1984;12(1):93-111.
Nisbet, A.P. et al., "Increased behavioural response to 5-methoxy-N,N-dimethyltryptamine but not to RU-24969 after intraventricular 5,7-dihydroxytryptamine administration," *Eur J Pharmacol*, 1984;104(1-2):177-80.
Ormsbee, H. S., 3$^{rd}$ et al., "Serotonin regulation of the canine migrating motor complex," *J Pharmacol Exp Ther*, 1984;231(2):436-40.
Räisänen, M.J., "The presence of free and conjugated bufotenin in normal human urine," *Life Sciences*, 1984;34(21):2041-2045.
Rasmussen, K. et al., "Activity of serotonin-containing neurons in nucleus centralis superior of freely moving cats," *Exp Neurol*, 1984;83(2):302-17
Strassman, R. J. et al., "Adverse reactions to psychedelic drugs. A review of the literature," *J Nerv Ment Dis*, 1984;172(10):577-95.
Trulson, M. E. et al., "Activity of serotonin-containing nucleus centralis superior (*Raphe medianus*) neurons in freely moving cats," *Exp Brain Res*, 1984;54(1):33-44.
Trulson, M. E. et al., "Differential effects of hallucinogenic drugs on the activity of serotonin-containing neurons in the nucleus centralis superior and nucleus raphe pallidus in freely moving cats," *J Pharmacol Exp Ther*, 1984;228(1):94-102.
Vesikari, T., "Increased "Take" Rate of Oral Rotavirus Vaccine in Infants after Milk Feeding," *The Lancet*, 1984;324(8404).
Clarke, K. A. et al. "Potentiation of motoneurone excitability by combined administration of 5-HT agonist and TRH analogue," *Neuropeptides*, 1985;6(3):269-82.
Davis, M. et al., "Antagonism of apomorphine-enhanced startle by alpha 1-adrenergic antagonists," *Eur J Pharmacol*, 1985;108(3):233-41.
Trulson, M.E et al., "Ascorbic acid antagonizes the behavioural effects of LSD in cats," *J Pharm Pharmacol*, 1985;37(12):930-1.
Ushijima, I. et al., "Neuronal mechanisms involved in drug-induced jumping behavior in mice," *Eur J Pharmacol*, 1985;112(2):225-9.
Youdim, M. B. et al., "Serotonergic involvement in pharmacological action of the anxiolytic-sedatives thalidomide and supidimide," *Eur J Pharmacol*, 1985;119(1-2):39-46.
Adrien, J. et al., "Ontogenesis of unit activity in the raphe dorsalis of the behaving kitten: its relationship with the states of vigilance," *Brain Res*, 1986;366(1-2):10-21.
Archer, T. et al., "Noradrenergic-serotonergic interactions and nociception in the rat," *Eur J Pharmacol*, 1986;120(3):295-307.
Carlsson, M. et al., "A central serotonin receptor agonist, 8-hydroxy-2-(di-n-propylamino) tetralin, has different effects on prolactin secretion in male and female rats," *Acta Pharmacol Toxicol* (*Copenh*), 1986;58(4):297-302.
Cunningham, K. A. et al., "Discriminative stimulus properties of the serotonin agonist MK 212," *Psychopharmacology* (*Berl*), 1986;90(2):193-7.
Danysz, W. et al., "Spinal noradrenergic neurotransmission and the analgesia induced by brief footshock," *Brain Res*, 1986;365(1):169-73.
Dickinson, S. L. et al., "5-Hydroxytryptamine-mediated behaviour in male and female rats," *Neuropharmacology*, 1986;25(7):771-6.
Goodwin, G. M. et al., "The effects of a 5-HT1 receptor ligand isapirone (TVX Q 7821) on 5-HT synthesis and the behavioural effects of 5-HT agonists in mice and rats," *Psychopharmacology* (*Berl*), 1986;89(3):382-7.
Goodwin, G. M. et al., "Lithium decreases 5-HT1A and 5-HT2 receptor and alpha 2-adrenoceptor mediated function in mice," *Psychopharmacology* (*Berl*), 1986;90(4):482-7.
Graeff, F. G. et al., "Modulation of the brain aversive system by GABAergic and serotonergic mechanisms," *Behav Brain Res*, 1986;21(1):65-72.
Gray, J. A. et al., "The effects of the GABA-mimetic drugs, progabide and baclofen, on the biochemistry and function of 5-hydroxytryptamine and noradrenaline," *Neuropharmacology*, 1986;25(7):711-6.
Gudelsky, G. A. et al., "Suppression of the hypo- and hyperthermic responses to 5-HT agonists following the repeated administration of monoamine oxidase inhibitors," *Psychopharmacology* (*Berl*), 1986;90(3):403-7.
Gudelsky, G. A. et al., "Thermoregulatory responses to serotonin (5-HT) receptor stimulation in the rat. Evidence for opposing roles of 5-HT2 and 5-HT1A receptors," *Neuropharmacology*, 1986;25(12):1307-13.
Heal, D. J. et al., "The influence of central noradrenergic function on 5-HT2-mediated head-twitch responses in mice: possible implications for the actions of antidepressant drugs," *Psychopharmacology* (*Berl*), 1986;89(4):414-20.

(56) References Cited

OTHER PUBLICATIONS

Kennett, G. A. et al., "Female rats are more vulnerable than males in an animal model of depression: the possible role of serotonin," *Brain Res*, 1986;382(2):416-21.
Dickinson, S. L. et al., "Reduced-5-hydroxytryptamine-dependent behavior in rats following chronic corticosterone treatment," *Brain Res*, 1985;345(1):10-8.
Drummond, G. I. et al., "Stimulation of adenylate cyclase in the heart of Aplysia californica by biogenic amines" *Comp Biochem Physiol C Comp Pharmacol Toxicol*, 1985;80(1):129-33.
Fornal, C. et al., "Activity of serotonin-containing neurons in nucleus raphe magnus in freely moving cats," *Exp Neurol*, 1985;88(3):590-608.
Gudelsky, G. A. et al., "Altered responses to serotonergic agents in Fawn-Hooded rats," *Pharmacol Biochem Behav*, 1985;22(3):489-92.
Heal, D. J. e al., "Intracerebroventricular administration of 5,7-dihydroxytryptamine to mice increases both head-twitch response and the number of cortical 5-HT2 receptors," *Neuropharmacology*, 1985;24(12):1201-5.
Kennett, G. A. et al., "Central serotonergic responses and behavioural adaptation to repeated immobilisation: the effect of the corticosterone synthesis inhibitor metyrapone," *Eur J Pharmacol*, 1985;119(3):143-52.
Kennett, G. A. et al., "Enhancement of some 5-HT-dependent behavioural responses following repeated immobilization in rats," *Brain Res*, 1985;330(2):253-63.
Lalonde, R. et al., "Chronic phenytoin and the stereotyped motor response induced by 5-methoxy-N,N-dimethyltryptamine in rats," *Brain Res*, 1985;326(2):388-91.
Martin, P. et al., "Dissociation of head twitches and tremors during the study of interactions with 5-hydroxytryptophan in mice," *J Pharmacol Methods*, 1985;13(3):193-200.
Mas, M. et al., "Stimulation of spinal serotonergic receptors facilitates seminal emission and suppresses penile erectile reflexes," *Brain Res*, 1985;342(1):128-34.
McLeod, W. R. et al., "Bufotenine reconsidered," *Acta Psychiatr Scand*, 1985;72(5):447-50.
Metz, A. et al., "The administration of baclofen to mice increases 5-HT2-mediated head-twitch behaviour and 5-HT2 receptor number in frontal cortex," *Neuropharmacology*, 1985;24(4):357-60.
Moser, P. C. et al., "Circadian variation in behavioural responses to central 5-HT receptor stimulation in the mouse," *Psychopharmacology* (*Berl*), 1985;86(1-2):223-7.
Nielsen, E. B., "Discriminative stimulus properties of lysergic acid diethylamide in the monkey," *J Pharmacol Exp Ther*, 1985;234(1):244-9.
Nielsen, E. B. et al., "The effect of drugs on the acquisition of stimulus control in a conditioned suppression procedure," *Psychopharmacology* (*Berl*), 1985;85(1):80-6.
Nielsen, E. B. et al., "Antagonism of the LSD cue by putative serotonin antagonists: relationship to inhibition of in vivo [3H]spiroperidol binding," *Behav Brain Res*, 1985;16(2-3):171-6.
Pugh, M. T. et al., "Effects of the putative D-1 antagonist SCH 23390 on stereotyped behaviour induced by the D-2 agonist RU24213," *Psychopharmacology* (*Berl*), 1985;87(3):308-12.
Sawyer, S. F. et al., "Antidromic activation of dorsal raphe neurons from neostriatum: physiological characterization and effects of terminal autoreceptor activation," *Brain Res*, 1985;332(1):15-28.
Schutz, M. T. et al., "Anti-aversive role of serotonin in the dorsal periaqueductal grey matter," *Psychopharmacology* (*Berl*), 1985;85(3):340-5.
Seeman, G. et al., "Indolealkylamines and prolactin secretion a structure-activity study in the central nervous system of the rat," *Neuropharmacology*, 1985;24(12):1195-1200.
Sills, M. A. et al., "Development of selective tolerance to the serotonin behavioral syndrome and suppression of locomotor activity after repeated administration of either 5-MeODMT or mCPP," *Life Sci*, 1985;36(26):2463-9.
Spampinato, U. et al., "Serotonin agonists reduce dopamine synthesis in the striatum only when the impulse flow of nigro-striatal neurons is intact," *J Neurochem*, 1985;45(3):980-2.
Costain DW, Green AR. "beta-Adrenoceptor antagonists inhibit the behavioural responses of rats to increased brain 5-hydroxytryptamine." Br J Pharmacol. 1978;64(2):193-200.
Cowen PJ, Grahame-Smith DG, Green AR, Heal DJ. "beta-Adrenoceptor agonists enhance 5-hydroxytryptamine-mediated behavioural responses." Br J Pharmacol. 1982;76(2):265-270.
Cox KEM, S.A.; Barsuglia, J.P.; Lancelotta, R; Davis, A.K. "Subjective improvements in substance use problems following 5-MeO-DMT use in an international sample" 2018.
Cuadra GR, Molina VA. "Behavioral reactivity following 5-MeODMT administration in 5,7-DHT-pretreated killer rats." Pharmacology Biochemistry and Behavior. 1990;36(2):287-290.
Da Motta LG, de Morais JA, Tavares A, Vianna LMS, Mortari MR, Amorim RFB, Carvalho RR, Paumgartten FJR, Pic-Taylor A, Caldas ED. "Maternal and developmental toxicity of the hallucinogenic plant-based beverage ayahuasca in rats." Reprod Toxicol. 2018;77:143-153.
Dakic V, Minardi Nascimento J, Costa Sartore R, Maciel RM, de Araujo DB, Ribeiro S, Martins-de-Souza D, Rehen SK. "Short term changes in the proteome of human cerebral organoids induced by 5-MeO-DMT." Sci Rep. 2017;7(1):12863.
Danysz W, Jonsson G, Minor BG, Post C, Archer T. "Spinal and locus coeruleus noradrenergic lesions abolish the analgesic effects of 5-methoxy-N,N-dimethyltryptamine." Behavioral and Neural Biology. 1986;46(1):71-86.
Danysz W, Minor BG, Post C, Archer T. "Chronic treatment with antidepressant drugs and the analgesia induced by 5-methoxy-N,N-dimethyltryptamine: attenuation by desipramine." Acta Pharmacol Toxicol (Copenh). 1986;59(2):103-112.
Davies MA, Setola V, Strachan RT, Sheffler DJ, Salay E, Hufeisen SJ, Roth BL. "Pharmacologic analysis of non-synonymous coding h5-$HT_{2A}$ SNPs reveals alterations in atypical antipsychotic and agonist efficacies." Pharmacogenomics J. 2006;6(1):42-51.
Davis AK, Barsuglia JP, Lancelotta R, Grant RM, Renn E. "The epidemiology of 5-methoxy—N,N-dimethyltryptamine (5-MeO-DMT) use: Benefits, consequences, patterns of use, subjective effects, and reasons for consumption." J Psychopharmacol. 2018:269881118769063.
Cox et al., "5-MeO-DMT and subjective improvements in post-traumatic stress disorder." 2018.
Davis AKL, R. L.; Barsuglia, J. P.; Grant, R; Renn, E. "5-Methoxy-N,N-Dimethyltryptamine (5-MeO-DMT): Patterns of use, motives for consumption, and acute subjective effects." Paper presented at: 12th Annual Bayview Research Symposium, 2017.
Davis AKL, R. L. "The healing potential of 5-MeO-DMT: Results from two survey studies." Midwest Psychedelic Therapy Symposium. Madison, Wisconsin; 2018.
De Araujo DB, Ribeiro S, Cecchi GA, Carvalho FM, Sanchez TA, Pinto JP, de Martinis BS, Crippa JA, Hallak JE, Santos AC. "Seeing with the eyes shut: neural basis of enhanced imagery following Ayahuasca ingestion." Hum Brain Mapp. 2012;33(11):2550-2560.
De Smet PAGM. "A multidisciplinary overview of intoxicating enema rituals in the western hemisphere." Journal of Ethnopharmacology. 1983;9(2-3):129-166.
DEA. "Schedules of Controlled Substances: Placement of 5-Methoxy-N,NDimethyltryptamine into Schedule I of the Controlled Substances Act" 2010.
Deakin JF, Green AR. "The effects of putative 5-hydroxytryptamine antagonists on the behaviour produced by administration of tranylcypromine and L-tryptophan or tranylcypromine and L-DOPA to rats." Br J Pharmacol. 1978;64(2):201-209.
Dickinson SL, Tulloch IF, Gadie B. "Effects of idazoxan on 5-hydroxytryptamine-mediated behaviour in the mouse and rat." J Psychopharmacol. 1991;5(3):187-195.
Dinger J, Woods C, Brandt SD, Meyer MR, Maurer HH. "Cytochrome P450 inhibition potential of new psychoactive substances of the tryptamine class." Toxicol Lett. 2016;241:82-94.
Dos Santos RG. "A critical evaluation of reports associating ayahuasca with life-threatening adverse reactions." J Psychoactive Drugs. 2013;45(2):179-188.

(56) References Cited

OTHER PUBLICATIONS

Dos Santos RG, Balthazar FM, Bouso JC, Hallak JE. "The current state of research on ayahuasca: A systematic review of human studies assessing psychiatric symptoms, neuropsychological functioning, and neuroimaging." J Psychopharmacol. 2016;30(12):1230-1247.
Dos Santos RG, Bouso JC, Hallak JEC. "Ayahuasca, dimethyltryptamine, and psychosis: a systematic review of human studies." Ther Adv Psychopharmacol. 2017;7(4):141-157.
Dos Santos RG, Osorio FL, Crippa JAS, Hallak JEC. "Classical hallucinogens and neuroimaging: A systematic review of human studies: Hallucinogens and neuroimaging." Neurosci Biobehav Rev. 2016;71:715-728.
Dos Santos RG, Valle M, Bouso JC, Nomdedeu JF, Rodriguez-Espinosa J, McIlhenny EH, Barker SA, Barbanoj MJ, Riba J. "Autonomic, neuroendocrine, and immunological effects of ayahuasca: a comparative study with d-amphetamine." J Clin Psychopharmacol. 2011;31(6):717-726.
Drug Enforcement Administration (DEA) DoJ. Schedules of Controlled Substances: Placement of 5-Methoxy-N,N-Dimethyltryptamine Into Schedule I of the Controlled Substances Act; 2009.
Drug Enforcement Administration (DEA) DoJ. Final Rule—Schedules of Controlled Substances: Placement of 5-Methoxy-N,N-Dimethyltryptamine into Schedule I of the Controlled Substances Act; 2010.
Duvvuri V, Risbrough VB, Kaye WH, Geyer MA. "5-HT1A receptor activation is necessary for 5-MeODMT-dependent potentiation of feeding inhibition." Pharmacol Biochem Behav. 2009;93(3):349-353.
E Sanders MTB. "Distribution, metabolism and excretion of bufotenine in the rat with preliminary studies of its O-methyl derivative." J Pharmacol Exp Ther. 1967.
Eide PK, Hole K. "Acute and chronic treatment with selective serotonin uptake inhibitors in mice: effects on nociceptive sensitivity and response to 5-methoxy-N, N-dimethyltryptamine." Pain. 1988;32(3):333-340.
Erowid. Ask Erowid: 5-MeO-DMT Reactions; https://www.erowid.org/ask/ask.php?ID=2860; 2001.
Erowid. 5-MeO-DMT Dosage; 2015; https://erowid.org/chemicals/5meo_dmt/5meo_dmt_dose.shtml.
Erowid. More 5-MeO-DMT Information; https://erowid.org/chemicals/5meo_dmt/5meo_dmt_info3.shtml; 2015.
Erowid. 5-MeO-DMT Timeline; https://erowid.org/chemicals/5meo_dmt/5meo_dmt_timeline.php; 2015.
Erritzoe D, Richards WA. "Lessons to be learned from early psychedelic therapy in Denmark." Nord J Psychiatry. 2017;71(7):487-488.
Erritzoe D, Roseman L, Nour MM, MacLean K, Kaelen M, Nutt DJ, Carhart-Harris RL. "Effects of psilocybin therapy on personality structure." Acta Psychiatr Scand. 2018.
Erspamer V, Vitali T, Roseghini M, Cei JM. 5-Methoxy- and 5-hydroxy-indolealkylamines in the skin of Bufo alvarius. *Experientia*. 1965;21(9):504.
Evans JP, Grahame-Smith DG, Green AR, Tordoff AF. "Electroconvulsive shock increases the behavioural responses of rats to brain 5-hydroxytryptamine accumulation and central nervous system stimulant drugs." Br J Pharmacol. 1976;56(2):193-199.
Evenden JL. "The effect of 5-HT1A receptor agonists on locomotor activity in the guinea-pig." Br J Pharmacol. 1994;112(3):861-866.
F Benington RDM, L C Clark Jr. "5-methoxy-N, N-dimethyltryptamine, a possible endogenous psychotoxin." The Alabama Journal of Medical Sciences. 1965.
Fabregas JM, Gonzalez D, Fondevila S, Cutchet M, Fernandez X, Barbosa PC, Alcazar-Corcoles MA, Barbanoj MJ, Riba J, Bouso JC. "Assessment of addiction severity among ritual users of ayahuasca. Drug Alcohol Depend." 2010;111(3):257-261.
FDA. PDAC Meeting—"Cognitive Dysfunction and MDD;" 2016.
Fone KC, Johnson JV, Bennett GW, Marsden CA. "Involvement of 5-HT2 receptors in the behaviours produced by intrathecal administration of selected 5-HT agonists and the TRH analogue (CG 3509) to rats." Br J Pharmacol. 1989;96(3):599-608.
Fone KC, Robinson AJ, Marsden CA. "Characterization of the 5-HT receptor subtypes involved in the motor behaviours produced by intrathecal administration of 5-HT agonists in rats." Br J Pharmacol. 1991;103(2):1547-1555.
Forsstrom T, Tuominen J, Karkkainen J. "Determination of potentially hallucinogenic N-dimethylated indoleamines in human urine by HPLC/ESI-MS-MS." Scand J Clin Lab Invest. 2001;61(7):547-556.
Fowler CJ, Ahlgren PC, Brannstrom G. "GH4ZD10 cells expressing rat 5-HT1A receptors coupled to adenylyl cyclase are a model for the postsynaptic receptors in the rat hippocampus." Br J Pharmacol. 1992;107(1):141-145.
Francis Schlemmer R, Davis JM. "A primate model for the study of hallucinogens. Pharmacology Biochemistry and Behavior." 1986;24(2):381-392.
Friedman E, Cooper TB, Dallob A. "Effects of chronic antidepressant treatment on serotonin receptor activity in mice." European Journal of Pharmacology. 1983;89(1-2):69-76.
Fuxe K, Holmstedt B, Jonsson G. "Effects of 5-methoxy-N,N-dimethyltryptamine on central monoamine neurons." European Journal of Pharmacology. 1972;19(1):25-34.
G.M. Goodwin RJD, A.J. Wood, A.R. Green. "Lithium decreases 5-HT1A and 5-HT 2 receptor and a2-adrenoreceptor mediated function in mice." Psychopharmacology. 1986.
Gable RS. "Risk assessment of ritual use of oral dimethyltryptamine (DMT) and harmala alkaloids." Addiction. 2007;102(1):24-34.
Galeffi C, Messana I, Bettolo GBM. "N,N-Dimethyl-5-Methoxytryptamine, a Component of a Dart Poison of the Yanoáma Indians." Journal of Natural Products. 2004;46(4):586-587.
Gallagher CH, Koch JH, Moore RM, Steel JD. "Toxicity of Phalaris Tuberosa for Sheep." Nature. 1964;204:542-545.
Gallimore AR. "Restructuring consciousness—the psychedelic state in light of integrated information theory." Front Hum Neurosci. 2015;9:346.
Gallimore AR, Strassman RJ. "A Model for the Application of Target-Controlled Intravenous Infusion for a Prolonged Immersive DMT Psychedelic Experience." Front Pharmacol. 2016;7:211.
Garcia-Romeu A, Griffiths RR, Johnson MW. "Psilocybin-occasioned mystical experiences in the treatment of tobacco addiction." Curr Drug Abuse Rev. 2014;7(3):157-164.
Gasser P., "Research Update: Psychedelic Group Therapy in Switzerland." MAPS; 2017.
Gasser P, Holstein D, Michel Y, Doblin R, Yazar-Klosinski B, Passie T, Brenneisen R., "Safety and efficacy of lysergic acid diethylamide-assisted psychotherapy for anxiety associated with life-threatening diseases". J Nerv Ment Dis. 2014;202(7):513-520.
Gaujac A, Martinez ST, Gomes AA, de Andrade SJ, Pinto AdC, David JM, Navickiene S, de Andrade JB. "Application of analytical methods for the structural characterization and purity assessment of N,N-dimethyltryptamine, a potent psychedelic agent isolated from Mimosa tenuiflora inner barks." Microchemical Journal. 2013;109:78-83.
Gessner PK, Page IH. "Behavioral effects of 5-methoxy-N:N-dimethyltryptamine, other tryptamines, and LSD." American Journal of Physiology—Legacy Content. 1962;203(1):167-172.
Office Action issued in BZ1022.21 (WO2020/169850), dated May 6, 2024.
Office Action issued in JP2021-575424 (WO2020/254584), dated May 7, 2024, translation.
Office Action issued in BR112021025526.5 (WO2020/254584), dated Apr. 26, 2024, partial translation.
Notice of Allowance issued in U.S. Appl. No. 18/604,747 dated May 8, 2024.
Office Action issued in CN 202180016407.1 (WO2021/170614) dated Nov. 30, 2023, translation.
Office Action issued in EA202192319 (WO2020/169851), dated Mar. 27, 2023, translation.
Office Action issued in CN202080045130.0 (WO2020/254584) dated Dec. 18, 2023, translation.
Office Action issued in JP2021-549427 (WO2020/169850), dated Jan. 30, 2024, translation.

(56) References Cited

OTHER PUBLICATIONS

Office Action issued in JP2021-549460 (WO2020/169851), dated Jan. 30, 2024, translation.
Office Action issued in CN202080030434.X (WO2020/169851), dated Mar. 21, 2024, translation.
Office Action issued in EA202292427 (WO2021/170614) dated Mar. 27, 2023, translation.
Office Action issued in EA202192318 (WO2020/169850) dated Mar. 24, 2023, translation.
Office Action issued in CN202080030317.3 (WO2020/169850) dated Mar. 6, 2024, translation.
Third party observation filed in EP4353314 (WO2020169850), dated Jun. 6, 2024.
Third party observation filed in EP4349407 (WO2020169850), dated Jun. 6, 2024.
European Search Report on EP4353314 (WO2020169850) dated Jun. 5, 2024.
European Search Opinion on EP4353314 (WO2020169850) dated Jun. 5, 2024.
European Search Strategy on EP4353314 (WO2020169850) dated Jun. 5, 2024.
European Search Report on EP4349407 (WO2020169850) dated Jun. 3, 2024.
European Search Opinion on EP4349407(WO2020169850) dated Jun. 3, 2024.
European Search Strategy on EP4349407(WO2020169850) dated Jun. 3, 2024.
Search Strategy issued in WIPO Patent Application No. PCT/EP2020/054803, Aug. 27, 2020.
Notice of Opposition filed in EP3927337 dated May 21, 2024.
Office Action issued in DOP2021000175 (WO2020/169851), dated Mar. 21, 2024, translation.
Office Action issued in SV2021-006313 (WO2020/169850) dated Nov. 27, 2022, translation.
Office Action issued in SV2021-006312 (WO2020/169851) dated Nov. 24, 2022, translation.
Office Action issued in MX/a/2021/009942 (WO2020/169851), dated Nov. 6, 2023, translation.
Pachter et al., Indole Alkaloids of *Acer saccharinum* (the Silver Maple), Dictyoloma incanescens, Piptadenia colubrina, and Mimosa hostilis, Journal of Organic Chemistry, 1959, 24(9), 1285-1287.
Bryson et al., RE104: Synthesis and Activity of a Novel Serotonergic Psychedelic Prodrug of 4-Hydroxy-N,N-diisopropyltryptamine, ACS Chem Neurosci, 2024, doi: 10.1021/acschemneuro.4c00058.
Rorsted et al., Discovery and Structure-Activity Relationships of 2,5-Dimethoxyphenylpiperidines as Selective Serotonin 5-HT(2A) Receptor Agonists, J Med Chem, 2024, 67 (9): 7224-7244, doi: 10.1021/acs.jmedchem.4c00082.
Johns Hopkins Medicine Newsroom website page "Fast-Acting Psychedelic Associated With Improvements in Depression/Anxiety," www.hopkinsmedicine.org/news/newsroom/news-releases/2019/03/fast-acting-psychedelic-associated-with-improvements-in-depressionanxiety from Mar. 18, 2019.
Archived version of the Mayo Clinic website page "Depression (major depressive disorder)", as it appeared on Jan. 17, 2019: www.web.archive.org/web/20190117042807/https://www.mayoclinic.org/diseases-conditions/depression/symptoms-causes/syc-20356007.
Archived version of the National Institute of Mental Health (NIMH) website page "Depression" as it appeared on Feb. 9, 2019: www.web.archive.org/web/20190209050443/https://www.nimh.nih.gov/health/topics/depression/index.shtml.
Kupfer et al., Major depressive disorder: new clinical, neurobiological, and treatment perspectives. Lancet. Mar. 17, 2012;379(9820):1045-55. doi: 10.1016/S0140-6736(11)60602-8. Epub Dec. 19, 2011. PMID: 22189047; PMCID: PMC3397431.
Forum post by user 'Handshake' dating from Nov. 30, 2017, available from www.forums.5meodmt.org/index.php/topic.50611.msg54941.html#msg54941.
Summary of: Warren et al., Structural pharmacology and therapeutic potential of 5-methoxytryptamines, Nature, 2024, 630, 8015, 237-246, Doi: 10.1038/s41586-024-07403-2.
Office Action issued in IL285539 (WO2020/169851), dated Apr. 30, 2024, translation.
Office Action issued in IL285537 (WO2020/169850), dated Apr. 30, 2024, translation.
Kwong, L. L. et al., "Differential interactions of "prosexual" drugs with 5-hydroxytryptamine1A and alpha 2-adrenergic receptors," *Behav Neurosci*, 1986;100(5):664-8.
Larson, A. A. et al., "Action of hallucinogens on raphe-evoked dorsal root potentials (DRPs) in the cat," *Pharmacol Biochem Behav*, 1986;24(2):347-50.
Lenahan, S. E. et al., "Evidence for multiple serotonergic influences on LH release in ovariectomized rats and for modulation of their relative effectiveness by estrogen," *Neuroendocrinology*, 1986;44(1):89-94.
Lima, L. et al., "Reserpine and the monoaminergic regulation of adrenal dopamine beta-hydroxylase activity," *Neuroscience*, 1986;17(1):235-45.
Martin, P. et al., "Comparative study of the effects of stimulation or blockade of beta-adrenoceptors on the head-twitches induced in mice by 5-hydroxytryptophan versus 5-methoxy-N, N-dimethyltryptamine," *J Pharmacol*, 1986;17(2):119-25.
Metz, A. et al., "In mice repeated administration of electroconvulsive shock or desmethylimipramine produces rapid alterations in 5-HT2-mediated head-twitch responses and cortical 5-HT2 receptor number," *Eur J Pharmacol*, 1986;126(1-2):159-62.
Minor, B. G. et al., "5-HT agonist induced analgesia modulated by central but not peripheral noradrenaline depletion in rats," *J Neural Transm*, 1986;66(3-4):243-59.
Peroutka, S. J. et al., "Canine basilar artery contractions mediated by 5-hydroxytryptamine1A receptors," *J Pharmacol Exp Ther*, 1986;237(3):901-6.
Peters, D. A. "Prenatal stress increases the behavioral response to serotonin agonists and alters open field behavior in the rat," *Pharmacol Biochem Behav*, 1986;25(4):873-7.
Post, C. et al., "Analgesia induced by 5-hydroxytryptamine receptor agonists is blocked or reversed by noradrenaline-depletion in rats," *Brain Res*, 1986;363(1):18-27.
Renyi, L., "The effect of selective 5-hydroxytryptamine uptake inhibitors on 5-methoxy-N, N-dimethyltryptamine-induced ejaculation in the rat," *British journal of pharmacology*, 1986;87(4):639-648.
Rényi, L., "The effects of monoamine oxidase inhibitors on the ejaculatory response induced by 5-methoxy-N, N-dimethyltryptamine in the rat," British journal of pharmacology, 1986;88(4):827-835.
Renyi, L., "Long lasting supersensitivity to 5-HT mediated behaviour following monoamine depletion in the rat brain," *Acta Pharmacol Toxicol* (*Copenh*), 1986;59(4):298-302.
Renyi, L. et al., "The inhibition of the cage-leaving response—a model for studies of the serotonergic neurotransmission in the rat," *J Neural Transm*, 1986;65(3-4):193-210.
Singh, L. et al., "Involvement of noradrenaline in potentiation of the head-twitch response by GABA-related drugs," *Psychopharmacology* (*Berl*), 1986;88(3):315-9.
Smith, L. M. et al., "Differential effects of 5-hydroxytryptamine1a selective drugs on the 5-HT behavioral syndrome," *Pharmacol Biochem Behav*, 1986;24(6):1513-9.
Yamawaki, S. et al., "Effect of long-term lithium treatment on serotonin syndrome in rats," *Yakubutsu Seishin Kodo*, 1986;6(2):247-52.
Yanai, K. et al., "In vivo kinetics and displacement study of a carbon-11-labeled hallucinogen, N,N-[11C]dimethyltryptamine," *Eur J Nucl Med*, 1986;12(3):141-6.
Archer, T., "5-Hydroxytryptamine antagonists and the 5-methoxy-N,N-dimethyltryptamine-induced changes of postdecapitation convulsions," *Pharmacol Toxicol*, 1987;60(1):37-42.
Archer, T. et al., "(+)-8-OH-DPAT and 5-MeODMT induced analgesia is antagonised by noradrenaline depletion," *Physiol Behav*, 1987;39(1):95-102.

(56) References Cited

OTHER PUBLICATIONS

Bennett, G. W. et al., "Thyrotrophin releasing hormone—5-hydroxytryptamine interactions in the brain studied using chronic immunization and chemical lesioning techniques," *J Recept Res*, 1987;7(1-4):555-79.
Cohen, A. I. et al., "Tryptamine and some related molecules block the accumulation of a light-sensitive pool of cyclic AMP in the dark-adapted, dark-incubated mouse retina," *J Neurochem*, 1987;48(3):729-37.
Critchley, M. A. et al., "Effects in the X-maze anxiety model of agents acting at 5-HT1 and 5-HT2 receptors," *Psychopharmacology* (*Berl*), 1987;93(4):502-6.
Cunningham, K. A. et al., "Discriminative stimulus properties of 8-hydroxy-2-(di-n-propylamino)tetralin (8-OHDPAT): implications for understanding the actions of novel anxiolytics," *Eur J Pharmacol*, 1987;138(1):29-36.
Dabire, H. et al., "Comparison of effects of some 5-HT1 agonists on blood pressure and heart rate of normotensive anaesthetized rats," *Eur J Pharmacol*, 1987;140(3):259-66.
Donohoe, T. P. et al., "Blockade of dopamine receptors explains the lack of 5-HT stereotypy on treatment with the putative 5-HT1A agonist LY165163," *Psychopharmacology* (*Berl*), 1987;93(1):82-6.
Feuerstein, T. J. et al., "The serotonin (5-HT) autoreceptor in the hippocampus of the rabbit: role of 5-HT biophase concentration," *Neuropharmacology*, 1987;26(8):1071-80.
Fileccia, R. et al., "5-Hydroxytryptamine involvement in the intrinsic control of oesophageal EMG activity," *Arch Int Physiol Biochim*, 1987;95(4):281-8.
Gilbert, R. J. et al., "Subtypes of muscarinic receptors in vagal inhibitory pathway to the lower esophageal sphincter of the opossum," *Dig Dis Sci*, 1987;32(10):1130-5.
Gudelsky, G. A. et al., "Selective desensitization of serotonin (5-HT) receptor-mediated hyperthermia by mianserin and other 5-HT antagonists," *Neuropharmacology*, 1987;26(7A):707-12.
Hallberg, H., "Blockade of central beta-adrenoceptors attenuates tremor induced by 5-hydroxytryptamine (5-HT)-receptor activation in rats," *Acta Physiol Scand*, 1987;129(3):421-8.
Jaffe, E. H. et al., "Dopamine and noradrenaline content in fish retina: modulation by serotonin," *J Neurosci Res*, 1987;18(2):345-51.
Kennett, G. A. et al, "Single administration of 5-HT1A agonists decreases 5-HT1A presynaptic, but not postsynaptic receptor-mediated responses: relationship to antidepressant-like action," *Eur J Pharmacol*, 1987;138(1):53-60.
Molina, V. et al., "Inhibition of mouse killing behavior by serotonin-mimetic drugs: effects of partial alterations of serotonin neurotransmission," *Pharmacol Biochem Behav*, 1987;27(1):123-31.
Nabeshima, T. et al., "Development of tolerance and supersensitivity to phencyclidine in rats after repeated administration of phencyclidine," *Eur J Pharmacol*, 1987;135(1):23-33.
Nabeshima, T. et al., "Phencyclidine-induced head-weaving observed in mice after ritanserin treatment," *Eur J Pharmacol*, 1987;139(2):171-8.
Nabeshima, T. et al., "Phencyclidine-induced head-twitch response in rats treated chronically with methysergide," *Eur J Pharmacol*, 1987;133(3):319-28.
Nabeshima, T. et al., "Phencyclidine-induced head-twitch responses as 5-HT2 receptor-mediated behavior in rats," *Neurosci Lett*, 1987;76(3):335-8.
Nabeshima, T. et al., "Potentiation in phencyclidine-induced serotonin-mediated behaviors after intracerebroventricular administration of 5,7-dihydroxytryptamine in rats," *J Pharmacol Exp Ther*, 1987;243(3):1139-46.
Nagano, N. et al., "Sensitivity of spinal reflexes to TRH and 5-HT in 5,6-dihydroxytryptamine-treated rats," *Eur J Pharmacol*, 1987;139(3):315-21.
Offord, S. J. et al., "Differential effects of nialamide and clomipramine on serotonin efflux and autoreceptors," *Pharmacol Biochem Behav*, 1987;26(3):593-600.
Ono, H. et al., "5-Hydroxytryptamine agonistic action of methysergide and the absence of supersensitivity to 5-HT agonists in spinal flexor reflexes in rats," *Neuropharmacology*, 1987;26(9):1371-5.
Pranzatelli, M. R. et al., "3-Acetylpyridine lesions and four serotonergic behavioral syndromes in the rat," *Brain Res Bull*, 1987;18(2):159-63.
Saito, R. et al., "The effect of neurotransmitters on cataleptic behavior induced by PG D2 in rats," *Pharmacol Biochem Behav*, 1987;26(3):543-6.
Singh, L. et al., "Behavioural evidence for an interdependence between GABAA receptors and beta 2-adrenoceptors," *Eur J Pharmacol*, 1987;135(3):419-21.
Sitaram, B. R. et al., "Gas chromatographic-mass spectroscopic characterisation of the psychotomimetic indolealkylamines and their in vivo metabolites," *J Chromatogr*, 1987;422:13-23.
Sitaram, B. R. et al., "Study of metabolism of psychotomimetic indolealkylamines by rat tissue extracts using liquid chromatography," *Biochem Pharmacol*, 1987;36(9):1503-8.
Soblosky, J. S. et al., "Evidence for 5-HT1A binding sites in chick embryo brain and discrimination by 5-methoxytryptamine," *Biochem Int*, 1987;14(5):797-803.
Spencer, D. G., Jr. et al., "The interoceptive discriminative stimuli induced by the novel putative anxiolytic TVX Q 7821: behavioral evidence for the specific involvement of serotonin 5-HT1A receptors," *Psychopharmacology* (*Berl*), 1987;91(1):25-9.
Traversa, U. et al., "Effects of an atypical barbiturate (valofan) on spontaneous and stimulated locomotor activity and on brain serotonin metabolism in mice," *Farmaco Sci*, 1987;42(10):755-66.
Winter, J. C. et al., "The effects of 8-hydroxy-2-(di-n-propylamino)tetralin and other serotonergic agonists on performance in a radial maze: a possible role for 5-HT1A receptors in memory," *Pharmacol Biochem Behav*, 1987;27(4):625-8.
Berger, A. et al., "Hypotensive spinal serotonergic effect. Are S1 or S2 receptors involved?" *Hypertension*, 1988;11(2 Pt 2):I182-5.
Dumuis, A. et al., "Pharmacology of 5-hydroxytryptamine-1A receptors which inhibit cAMP production in hippocampal and cortical neurons in primary culture," *Mol Pharmacol*, 1988;33(2):178-86.
Dumuis, A. et al., "A nonclassical 5-hydroxytryptamine receptor positively coupled with adenylate cyclase in the central nervous system," *Mol Pharmacol*, 1988;34(6):880-887.
Duncan, M. J.; Takahashi, J. S.; Dubocovich, M. L., "2-[125I]iodomelatonin binding sites in hamster brain membranes: pharmacological characteristics and regional distribution," *Endocrinology*, 1988;122(5):1825-33.
Office Action issued in DOP2021-0176 (WO2020/169850), dated Mar. 6, 2023, translation.
Office Action issued in DOP2021-0176 (WO2020/169850), dated Mar. 21, 2024, translation.
Office Action issued in CR20210437 (WO2020/169850), dated Mar. 4, 2024, translation.
Office Action issued in CL2022-02303 (WO2021/170614), dated Jun. 6, 2024, translation.
Quilty et al., The structure of the Montgomery-Asberg depression rating scale over the course of treatment for depression, International Journal of Methods in Psychiatric Research, Aug. 19, 2013, 22(3).
Liu Yan et al., Treatment of treatment-resistant major depression, Jilin Science and Technology Press, Jun. 30, 2017, pp. 521-524.
Wang Juyue et al., Synthesis and Spectral Analysis of 5-R-N, N-Dimethyl Tryptamines Derivatives, Chinese Journal of Spectroscopy Laboratory, Mar. 31, 2011, 28(2), pp. 715-717.
Notice of residual solvent guidelines for medicines, Chief notice of chief administrative judge of Health, Ministry of Health, Ministry of Health, Medicine, Notification No. 307, Mar. 30, 1998.
Office Action issued in MX/a/2021/009942 (WO2020/169851), dated Apr. 10, 2024.
Office Action issued in MX/a/2021/009941 (WO2020/169850) dated Apr. 23, 2024.
Office Action issued in CA 3130406 (WO2020/169850), dated Feb. 12, 2025.
Office Action issued in CA 3130180 (WO2020/169851), dated Feb. 12, 2025.

(56) References Cited

OTHER PUBLICATIONS

Office Action issued in CO NC2021/0010883 (WO2020/169851), dated Feb. 11, 2025, translation.
Office Action issued in CR 2022-0000417 (WO2021/170614), dated Feb. 12, 2025, translation.
Office Action issued in JP 2022-549753 (WO2021/170614), dated Mar. 4, 2025.
Office Action issued in CO NC2021/0010882 (WO2020/169850), dated Feb. 25, 2025, translation.
Piccinini et al., "Transient destabilization of whole brain dynamics induced by N,N-Dimethyltryptamine (DMT)", Communications Biology, 2025, 8(1), doi: 10.1038/s42003-025-07576-0.
Griffiths et al., "Survey of subjective God encounter experiences: Comparisons among naturally occurring experiences and those occasioned by the classic psychedelics psilocybin, LSD, ayahuasca, or DMT", PLoS One, 2019, 14(4): e0214377, doi: 10.1371/journal.pone.0214377.
Office Action issued in MX/a/2022/010417 (WO2021/170614), dated Jun. 4, 2025.
Office Action issued in PA 93611-01 (WO2020/169850) dated Jun. 10, 2025, translation.
Office Action issued in CR2021-000437 (WO2020/169850), dated Jun. 27, 2025.
Reply from Opponent to Submission of Proprietor in EP3927337 (WO2020169850), dated Jul. 9, 2025.
Notice of Opposition filed in EP3927338 (WO2020169851), dated Jul. 15, 2025.
Reply from Opponent to Submission of Proprietor in EP4313945 (WO2023186834), dated Jul. 9, 2025.
Summons to Attend Oral Proceedings and Preliminary Opinion EP4313945 (WO2023186834), dated Jul. 18, 2025.
Erowid Online Books : "TIHKAL—The Continuation" by Alexander and Ann Shulgin, 1997 retrieved from https://www.erowid.org/library/books_online/tihkal/tihkal.shtml.
Shadani et al., Potential Differences in Psychedelic Actions Based on Biological Sex, Endocrinology, 2024, 165(8), doi: 10.1210/endocr/bqae083.
Souza et al., Validation of an analytical method for the determination of the main ayahuasca active compounds and application to real ayahuasca samples from Brazil, J Chromatogr B Analyt Technol Biomed Life Sci, 2019, 1124: 197-203, doi: 10.1016/j.jchromb.2019.06.014.
GH Research , GH Research Announces Primary Endpoint Met in Phase 2b Trial with GH001 in TRD Demonstrating—15.5 Point Placebo-adjusted MADRS Reduction, Feb. 3, 2025, retrieved from https://investor.ghres.com/news-releases/news-release-details/gh-research-announces-primary-endpoint-met-phase-2b-trial-gh001.
Thase, The multifactorial presentation of depression in acute care, 2013, retrieved from https://www.psychiatrist.com/pcc/multifactorial-presentation-depression-acute-care-2/ on Jul. 6, 2025.
Thase, using biomarkers to predict treatment response in major depressive disorder: evidence from past and present studies, Dialogues Clin Neurosci., Dec. 2014;16(4):539-44. doi: 10.31887/DCNS.2014.16.4/mthase.
Thase, Speaker at 26 Int. Symposium Controversies in Psychiatry, Apr. 27, 2019.
Jeffrey J Rakofsky et al., The prevalence and severity of depressive symptoms along the spectrum of unipolar depressive disorders: a post hoc analysis, J Clin Psychiatry, Nov. 2013;74(11):1084-91. doi: 10.4088/JCP.12m08194.
Johnson & Johnson, "Janssen Announces U.S. FDA Approval of Spravato® (esketamine) CIII Nasal Spray to Treat Depressive Symptoms in Adults with Major Depressive Disorder with Acute Suicidal Ideation or Behavior," Aug. 3, 2020, retrieved from https://www.jnj.com/media-center/press-releases/janssen-announces-u-s-fda-approval-of-spravato-esketamine-ciii-nasal-spray-to-treat-depressive-symptoms-in-adults-with-major-depressive-disorder-with-acute-suicidal-ideation-or-behavior.
February 2025 Psychedelic Patent Update: Terran Secures New Overlapping IP; Porta Sophia Becomes USPTO Information Source, Psychedelic Alpha, Mar. 27, 2025, retrieved from https://psychedelicalpha.com/news/february-2025-psychedelic-patent-update-terran-secures-new-overlapping-ip-porta-sophia-becomes-uspto-information-source.
Second declaration of Mark Seelig as filed in EP3927337, dated Jul. 7, 2025.
Evidence that Dr Thase is a scientific advisor for GH Research, Retrieved on Jul. 7, 2025 from https://www.ghres.com/company/scientific-advisors/michael-thase-md#:~:text=Prof.%20Michael%20Thase%20is%20Professor%20of%20Psychiatry%20and,School%20of%20Medicine%20of%20the%20University%20of%20Pennsylvania.
Extract from IUPAC Gold Book—Definition of "salt," Retrieved from https://goldbook.iupac.org/terms/view/S05447; cited in Reply from Opponent to Submission of Proprietor in EP4313945 (WO2023186834), dated Jul. 9, 2025.
Letter of Dr Joanne Kirkwood addressed to Scorpio IP Limited dated Jul. 2, 2025.
IPRP issued in WIPO Patent Application No. PCT/EP2024/050139 (WO2024146917), dated Jul. 3, 2025.
Office Action issued in CA 3,144,038 (WO2020/254584), dated Jun. 30, 2025.
Office Action issued in CR 2021-000436 (WO2020/169851), dated Jul. 10, 2025, translation.
Office Action issued in MX/a/2025/002567 (WO2020/169850), dated Jul. 28, 2025, translation.
Office Action issued in CO NC2021/0010882 (WO2020/169850), dated Aug. 1, 2025.
Office Action issued in MX/a/2022/010417 (WO2021/170614), dated Jun. 4, 2025, translation.
Office Action issued in CR 2021-000437 (WO2020/169850), dated Jun. 27, 2025, translation.
Office Action issued in CO NC2021/0010882 (WO2020/169850), dated Aug. 1, 2025, translation.
Office Action issued in CO NC2021/0010883 (WO2020/169851), dated Aug. 11, 2025, translation.
Office Action issued in CL 2021-02173 (WO2020/169851), dated Aug. 5, 2025, translation.
Office Action issued in CL 2021-02174 (WO2020/169850), dated Aug. 5, 2025, translation.
Office Action issued in KR 10-2021-7030216 (WO2020/169851), mailed on Aug. 29, 2025, translation.
Office Action issued in KR 10-2021-7030215 (WO2020/169850), mailed on Aug. 29, 2025, translation.
Office Action issued in IL285539 (WO2020/169851), dated Sep. 9, 2025, translation.
Office Action issued in IL285537 (WO2020/169850), dated Sep. 9, 2025, translation.
Timmermann et al., Exploring 5-MeO-DMT as a pharmacological model for deconstructed consciousness, Neurosci Conscious., Apr. 19, 2025 (1):niaf007. doi: 10.1093/nc/niaf007.
Johnson et al., Potential Therapeutic Effects of Psilocybin, Neurotherapeutics, Apr. 30, 2018, 32(7), pp. 779-792, doi: 10.1007/s13311-017-0542-y.
Office Action issued in KR 10-2022-7001747 (WO2020/254584), mailed on Apr. 15, 2025, translation.
Office Action issued in AU 2020296286 (WO2020/254584), dated May 8, 2025.
Third Party Submission filed in U.S. Appl. No. 18/290,976, on May 13, 2025.
Wikipedia, Diethyl Ether, https://web.archive.Org/web/20210502053557/http://en.wikipedia.org/wiki/Diethyl_ether [Archived version of how the webpage appeared on May 2, 2021].
Office Action issued in U.S. Appl. No. 18/675,614, dated May 5, 2025.
Nestler et al., Epigenetic Regulation in the Nervous System, Elsevier Science, 2012: 53-57.
APA Dictionary of Psychology, American Psychological Association, https://dictionary.apa.org/suicidality, published on Apr. 14, 2018.
McCormack et al., Is Bigger Better? An Argument for Very Low Starting Doses, Canadian Medical Association, Jan. 11, 2011, 183(1).

(56) References Cited

OTHER PUBLICATIONS

Barrett et al.. Qualitative and Quantitative Features of Music Reported to Support Peak Mystical Experiences during Psychedelic Therapy Sessions, Frontiers in Psychology, Jul. 25, 2017, 8, 1238, doi: 10.3389/fpsyg.2017.01238.
Information on search strategy for ISR on WO2025083212 dated Jan. 23, 2025.
International Search Report on WO2025083212 mailed Jan. 23, 2025.
Written Opinion of the International Searching Authority on WO2025083212 dated Jan. 23, 2025.
Annex for EP4313945—data from salt and polymorph screens: 5-MeO-DMT, submitted May 8, 2025.
X'Pert PRO X-ray Diffraction System; User's Guide; Sixth Edition (© 2007); introduction and Chapter 6: "X-ray Mirrors," 2007, p. 6.1 to 6.36.
Jurczak et al., "Pharmaceutical Hydrates Analysis-Overview of Methods and Recent Advances," Pharmaceutics, 2020, 12, 959; doi:10.3390/pharmaceutics12100959.
Aulton et al., Aulton's Pharmaceutics, the Design and Manufacture of Medicines, Fifth Edition (2018), ISBN 978-0-7020-7005-1; Introduction and Chapter 2: Dissolution and solubility (pp. 18 to 36).
Woolfson, An Introduction to X-ray Crystallography, Second Edition, Cambridge University Press, 1997.
Romeo et al., The intensity of the psychedelic experience is reliably associated with clinical improvements: A systematic review and meta-analysis, Neurosci Biobehav Rev, 2025, 172: 106086, doi: 10.1016/j.neubiorev.2025.106086.
Falchi-Carvalho et al., Rapid and sustained antidepressant effects of vaporized N,N-dimethyltryptamine: a phase 2a clinical trial in treatment-resistant depression, Neuropsychopharmacology, 2025, doi: 10.1038/s41386-025-02091-6.
Falchi-Carvalho et al., Supplemental Information to Rapid and sustained antidepressant effects of vaporized N,N-dimethyltryptamine: a phase 2a clinical trial in treatment-resistant depression, Neuropsychopharmacology, 2025, doi: 10.1038/s41386-025-02091-6.
Good et al., Pharmacokinetics of N, N-dimethyltryptamine in humans, European Journal of Drug Metabolism and Pharmacokinetics2023, 48(3): 311-327.
Watts et al., Patients' accounts of increased 'connection' and 'acceptance' after psilocybin for treatment-resistant depression, Journal of Humanistic Psychology, 2017.
Supplementary Materials to Watts et al., Patients' accounts of increased 'connection' and 'acceptance' after psilocybin for treatment-resistant depression, Journal of Humanistic Psychology, 2017.
GH Research, Clinical Trials, www.ghres.com/our-work/clinical-trials, as retrieved May 22, 2025.
Office Action issued in BR112022015758.4 (WO2021/170614), dated May 7, 2025.
Office Action issued in PE 001360-2021/DIN (WO2020/169850), dated Sep. 5, 2025, translation.
Office Action issued in PE 001359-2021/DIN (WO2020/169851), dated Sep. 3, 2025, translation.
Submission from Opponent to Proprietor in EP3927337 (WO2020169850), dated Sep. 3, 2025.
U.S. National Library of Medicine Depression screening: Medlineplus medical test., MedlinePlus, Dec. 15, 2022, retrieved from https://medlineplus.gov/lab-tests/depression-screening/.
Raskin, "Are There Viable Alternatives to the DSM-5?" Psychology Today United Kingdom, May 22, 2019 retrieved from https://www.psychologytoday.com/us/blog/making-meaning/201905/are-there-viable-alternatives-to-the-dsm-5.
Demyttenaere et al., The Impact of (the Concept of) Treatment-Resistant Depression: An Opinion Review, Int J Neuropsychopharmacol., Feb. 1, 2019;22(2):85-92. doi: 10.1093/ijnp/pyy052.
Dr. Michael Thase on the Prevalence of Stigma Surrounding Major Depressive Disorder (Video), AJMC, Psych Congress Nov. 19, 2018.
Holtzheimer et al., Deep Brain Stimulation for Treatment-Resistant Depression, Am J Psychiatry, Dec. 2010; 167(12):1437-1444.
Zagorski, Experts Debate What's Next for DBS for Depression, Psych News, vol. 55, No. 6, doi: 10.1176/appi.pn.2020.3b15 (2020).
Deep brain stimulation for depression hits a(nother) roadblock, Queensland Brain Institute, Aug. 20, 2015, updated May 18, 2017, retrieved from https://qbi.uq.edu.au/blog/2017/02/deep-brain-stimulation-depression-hits-another-roadblock.
Thase, "How should efficacy be evaluated in randomized clinical trials of treatments for depression?" J Clin Psychiatry, 1999;60 Suppl 4:23-31; discussion 32. PMID: 10086480.
Kwan et al., The ABCs of psychedelics: a preclinical roadmap for drug discovery, Trends Pharmacol Sci., 2025, doi: 10.1016/j.tips.2025.07.017.
Hager, The shifting fortunes of corporate psychedelia, Finance and Society, 2025, 1-23, doi: 10.1017/fas.2025.10014.
Blackburne et al. Complex slow waves in the human brain under 5-MeO-DMT, Cell Rep 2025, 44(8): 116040, doi: 10.1016/j.celrep.2025.116040.
Koch, The void and the brain, Cell Rep, 2025, 44(8): 116072, doi: 10.1016/j.celrep.2025.116072.
Bonniwell et al., Serotonin 5-HT(2C) Receptor Signaling Analysis Reveals Psychedelic Biased Agonism, ACS Chem Neurosci, 2025, doi: 10.1021/acschemneuro.5c00647.
Riba et al., Subjective effects and tolerability of the South American psychoactive beverage Ayahuasca in healthy volunteers, Psychopharmacology (Berl), 2001, 154(1): 85-95, doi: 10.1007/s002130000606.
Patent application document for EP 19158774 filed on Feb. 22, 2019.
Patent application document for EP 19158806 filed on Feb. 22, 2019.
Reply from Proprietor in EP3927337 (WO2020169850), dated Oct. 17, 2025.
Office Action issued in AU 2020225410 (WO2020/169850), dated Oct. 13, 2025.
Office Action issued in AU 2020225766 (WO2020/169851), dated Oct. 13, 2025.
Summons to oral proceedings and preliminary opinion in EP3927337 (WO2020169850), dated Nov. 5, 2025.
Reply from the proprietor to the notice of opposition in EP3927338 (WO2020169851), dated Nov. 21, 2025.
Fantegrossi et al., "Transient reinforcing effects of phenylisopropylamine and indolealkylamine hallucinogens in rhesus monkeys," Behav Pharmacol, 2004, 15(2): 149-57, doi: 10.1097/00008877-200403000-00007.
Lema, "Contemporary Uses of Vilca (Anadenanthera colubrina var cebil): A Major Ritual Plant in the Andes," Plants (Basel), 2024, 13(17), doi: 10.3390/plants13172398.
Torres, "The use of psychoactive plants by ancient indigenous populations of the North Andes," Journal of Psychedelic Studies, 2019, 3(2): 198-211, doi: 10.1556/2054.2018.015.
Rodd et al., "Yopo, ethnicity and social change: a comparative analysis of Piaroa and Cuiva yopo use," J Psychoactive Drugs, 2011, 43(1): 36-45, doi: 10.1080/02791072.2011.566499.
Marek et al., "A novel psychedelic 5-HT(2A) receptor agonist GM-2505: The pharmacokinetic, safety, and pharmacodynamic profile from a randomized trial healthy volunteer," J Psychopharmacol, 2025, 16:2698811251378512, doi: 10.1177/02698811251378512.
Morales-Garcia et al., "The alkaloids of Banisteriopsis caapi, the plant source of the Amazonian hallucinogen Ayahuasca, stimulate adult neurogenesis in vitro," Sci Rep, 2017; 7(1): 5309, doi: 10.1038/s41598-017-05407-9.
Padawer-Curry et al., "Psychedelic 5-HT(2A) receptor agonism alters neurovascular coupling and differentially affects neuronal and hemodynamic measures of brain function," Nat Neurosci, 2025, doi: 10.1038/s41593-025-02069-z.
Ortiz Bernal et al., "Reactivations Associated with the Use of 5-MeO-DMT Among Spanish-Speaking Individuals: Prevalence,

(56) References Cited

OTHER PUBLICATIONS

Predictors, and Emotional Valence," J Psychoactive Drugs, 2025, pp. 1-11, doi: 10.1080/02791072.2025.2577305.
Millon et al., "Safety and tolerability of multiple sublingual microdoses of 5-MeO-DMT in adults with moderate symptoms of depression and/or anxiety: a randomized, double-blind, placebo-controlled study," Neuropsychopharmacology, 2025, 50(11): 1715-1723, doi: 10.1038/s41386-025-02167-3, with supplemental materials including Cardiologic, Biochemical, and Neuropsychological Measurements.
Johnson & Johnson, "Janssen Announces U.S. FDA Approval of Spravato™ (esketamine) CIII Nasal Spray for Adults with Treatment-Resistant Depression (TRD) Who Have Cycled Through Multiple Treatments Without Relief," Mar. 5, 2019, retrieved from https://www.jnj.com/media-center/press-releases/janssen-announces-u-s-fda-approval-of-spravatotm-esketamine-ciii-nasal-spray-for-adults-with-treatment-resistant-depression-trd-who-have-cycled-through-multiple-treatments-without-relief.
Johnson & Johnson, "Janssen Announces U.S. FDA Approval of Spravato® (esketamine) CIII Nasal Spray to Treat Depressive Symptoms in Adults with Major Depressive Disorder with Acute Suicidal Ideation or Behavior," Aug. 3, 2020, retrieved from https://www.jnj.com/media-center/press-releases/janssen-announces-u-s-fda-approval-of-spravato-esketaminc-ciii-nasal-spray-to-treat-depressive-symptoms-in-adults-with-major-depressive-disorder-with-acute-suicidal-ideation-or-behavior.
Devlin et al., "Psychoactive effects of GH001 in patients with treatment-resistant depression: Results from a Phase 2b, double-blind, randomised controlled trial," Oct. 11-14, 2025.
Atai Corporate Presentation, "Pioneering the development of highly effective mental health treatments to transform patient outcomes," Oct. 2025, retrieved from https://ir.atai.com/newsevents/presentations.
Singh et al., "A double-blind, randomized, placebo-controlled, dose frequency study of intravenous ketamine in patients with treatment-resistant depression," Am J Psychiatry, 179:8, Aug. 2016, pp. 816-826.
Zarate et al., "A randomized trial of an N-methyl-D-aspartate antagonist in treatment-resistant major depression," Arch Gen Psychiatry, vol. 63, Aug. 2006 (reprinted), pp. 856-864.
GH Research, Redacted excerpt from "The Clinical Study Report for GH001-TRD-102," Appendix 16, Oct. 17, 2022.
FDA, "Major Depressive Disorder: Developing Drugs for Treatment Guidance for Industry," Jun. 2018.
Kramer et al., Psychedelics produce enduring behavioral effects and functional plasticity through mechanisms independent of structural plasticity, Neuropsychopharmacology, 2025, doi: 10.1038/s41386-025-02272-3.
Palhano-Fontes, Response to the letter to the editor: Compressed design, inflated conclusions? A cautionary note on vaporized DMT trials, Eur Neuropsychopharmacol, 2025, 100: 40-41, doi: 10.1016/j.curoneuro.2025.09.008.
Z. Lei, "Compressed design, inflated conclusions? A cautionary note on vaporized DMT trials," Eur Neuropsychopharmacol, 2025, 99: 13, doi: 10.1016/j.euroneuro.2025.07.008.
Ramaekers et al., Not all psychedelics are created equal. Nature Mental Health, 2025, doi: 10.1038/s44220-025-00551-y.
Davidson J et al., The Montgomery-Asberg Depression Rating Scale: reliability and validity, Acta Psychiatr Scand. May 1986;73(5):544-8. doi: 10.1111/j.1600-0447.1986.tb02723.x. PMID: 3751660.
Third Party Submission filed in U.S. Appl. No. 18/851,329, on Nov. 24, 2025.
Third Party Submission filed in U.S. Appl. No. 18/850,394, on Nov. 24, 2025.
Third Party Submission filed in U.S. Appl. No. 18/851,322, on Nov. 14, 2025.
Third Party Submission filed in U.S. Appl. No. 18/851,356, on Nov. 20, 2025.
Third Party Submission filed in U.S. Appl. No. 18/679,917, on Oct. 18, 2025.
Abel, Prevalence of maternal mental illness among children and adolescents in the UK between 2005 and 2017: a national retrospective cohort analysis, Lancet Public Health, 2019, 4(6): 291-300.
Busner, The Clinical Global Impressions scale: errors in understanding and use, Comprehensive Psychiatry 2009, 50(3): 257-262.
Leonard, Postpartum perceived stress explains the association between perceived social support and depressive symptoms, Women's Health Issues,2020, 30(4): 231-239.
Bergfeld, Treatment-resistant depression and suicidality, Journal of Affective Disorders, 2018, 235: 362-367.
Muller et al., Moderate and severe depression: Gradations of the Montgomery-Asberg Depression Rating Scale, Journal of Affective Disorders, 2000, 60(2): 137-140.
Zimmerman et al., Severity classification on the Hamilton Depression Rating Scale, Journal of Affective Disorders, 2013, 150(2): 384-388.
Wayback Machine, Volcano—Storz & Bickel website from 2019, retrieved on Dec. 2, 2025 from https://web.archive.org/web/20190825072737/https://www.storz-bickel.com/us/en/volcano/.
Our Mission at Vapormed, retrieved on Dec. 2, 2025 from www.vapormed.com/en/about-us (6 pages).
Operating instructions for the Volcano Classic, pp. 46-87, downloaded from https://www.storz-bickel.com/en-us/downloads on Dec. 2, 2025.
Operating instructions for the Volcano Hybrid, pp. 46-87, downloaded from https://www.storz-bickel.com/en-us/downloads on Dec. 2, 2025.
Operating instructions for Volcano Digit, pp. 50-95, downloaded from https://www.storz-bickel.com/en-us/downloads on Dec. 2.
Operating instructions for Volcano Medic 2, downloaded on Dec. 2, 2025 from https://cdn.shopify.com/s/files/1/0514/2023/3890/files/volcano-medic-2-instructions-en.pdf?v=1658190045 66 pages.
Rabinowitz et al., Ultra-Fast Absorption of Amorphous Pure Drug Aerosols via Deep Lung Inhalation, Journal of Pharmaceutical Sciences, vol. 95, No. 11, Nov. 2006, pp. 2438-2451.
Dinh et al., In vitro acrosol characterization of Staccato Loxapine, International Journal of Pharmaceutics 403 (2011) 101-108.
Dominguez-Clave et al., "Ayahuasca: Pharmacology, neuroscience and therapeutic potential," Brain Res Bull, 2016, 126, Pt 1: 89-101, doi: 10.1016/j.brainresbull.2016.03.002.
Rivier et al., "Ayahuasca," the South American hallucinogenic drink: An ethnobotanical and chemical investigation, Economic Botany, 1972, 26(2): 101-129, doi: 10.1007/bf02860772.
McKenna et al., "Monoamine Oxidase Inhibitors in South American hallucinogenic Plants: Tryptamine and β-Carboline Constituents of Ayahuasca," Journal of Ethnopharmacology, 1984, 10(2):195-223. doi: 10.1016/0378-8741(84)90003-5. PMID: 6587171.
Agurell et al., "Alkaloid Content of Banisteriopsis Rusbyana," Am J Pharm Sci Support Public Health, Sep.-Oct. 1968;140(5):148-51. PMID: 5698439.
Executed Declaration under 37 C.F.R. § 1.132 of Dr. Laurent Rivier dated Nov. 5, 2025.
Third Party Submission filed in U.S. Appl. No. 18/851,294, on Dec. 2, 2025.
Office Action issued in BR112022015758.4 (WO2021/170614), dated May 7, 2025, translation.
Office Action issued in CN202180016407.1 (WO2021/170614), dated May 28, 2025, translation.
Office Action issued in HN 2021-001978 (WO2020/169850) dated Jun. 10, 2025, translation.
Office Action issued in U.S. Appl. No. 17/801,389, dated Jun. 3, 2025 [P66767].
Office Action issued in IL295758 (WO2021/170614) dated Jun. 8, 2025, translation.
Reply to Notice of Opposition filed in EP3927337, dated Jun. 3, 2025.
A. Wsol, Cardiovascular safety of psychedelic medicine: current status and future directions, Pharmacological Reports, 2023, 75 (6): 1362-1380.
D. E. Nichols, Hallucinogens, Pharmacol Ther, 2004, 101 (2): 131-81.

(56) References Cited

OTHER PUBLICATIONS

R. Khare, Unlocking the Therapeutic Potential of DMT's: Molecular Modelling Insights into Neuropharmacological Mechanisms and Clinical Prospects, Letters in Applied NanoBioScience, 2024, 13(2), 99.
J. T. Reckweg et al., Evaluation of the peak experience scale as a rapid assessment tool for the strength of a psychoactive experience with 5-MeO-DMT, Frontiers in Psychology, 2025, 16, doi: 10.3389/fpsyg.2025.1543640.
O. Suzuki et al., Characterization of eight biogenic indoleamines as substrates for type A and type B monoamine oxidase, Biochemical Pharmacology, 1981, 30 (11): 1353-1358.
O'Brien, The Pharmacological Basis of Therapeutics—Goodman and Gilman's, 2015.
R. A. Glennon, & Rosecrans, J. A., Speculations on the mechanism of action of hallucinogenic indolealkylamines, Neuroscience & Biobehavioral Reviews, 1981, 5(2): 10.
J C Gillin et al., The psychedelic model of schizophrenia: the case of N,N-dimethyltryptamine, The American Journal of Psychiatry, 1976, 133(2): 6.
V. P. Acero et al., From molecules to meaning: unpacking the antidepressant mechanisms of psychedelic drugs, Expert Rev Clin Pharmacol, 2025, pp. 1-18.
Y. Zhang et al., The molecular mechanisms through which psilocybin prevents suicide: evidence from network pharmacology and molecular docking analyses, Transl Psychiatry, 2025, 15(1): 202.
A. M. Wingert et al., Serotonergic psychedelics for depression: A comprehensive overview, Int Rev Neurobiol, 2025, 181: 271-304.
European Monitoring Centre for Drugs and Drug Addiction (2023), European Drug Report 2023: Trends and Developments, retrieved from https://www.euda.europa.eu/publications/european-drug-report/2023/drug-situationin-europe-up-to-2023_en.
"Intractable Byproduct in 5-MeO-DMT Samples", retrieved Aug. 2021 from https://www.erowid.org/columns/crew/2021/08/5-meo-dmt synthesis byproduct/.
Declaration and *Curriculum Vitae* of Dr. Michael Thase, dated May 22, 2025.
Biography of Dr. Gerardo Sandoval Isaac. Psychedelic Times, 2016, retrieved on Mar. 4, 2025, from https://retreat.guru/teachers/756-59/dr-g.
Roger R., What is the Difference between 5-MeO-DMT and DMT? Choosing a DMT Therapy. Psychedelic Times., Feb. 26, 2016, retrieved from https://psychedelictimes.com/what-is-the-difference-between-5-meo-dmt-and-dmt-choosing-a-dmttherapy/#:~:text=While%20the%20DMT%20experience%20tends,blown%20forcefully%20into%20the%20nose.
Alexander et al., Preclinical models for evaluating psychedelics in the treatment of major depressive disorder, British Journal of Pharmacology, 2024, p. 1-22.
R. Milliere et al., Psychedelics, Meditation, and Self-Consciousness, Front Psychol, 2018, 9, 1475, pp. 1-29, doi: 10.3389/fpsyg.2018.01475.
Thase et al., Safety and Efficacy of GH001in TRD: Results from a Phase 2b, Double-blind, Randomized Controlled Trial; Poster presented at the American Society of Clinical Psychopharmacology Annual Meeting, May 27-30, 2025.
Thase et al., Safety and Efficacy of GH001in TRD: Results from a Phase 2b, Double-blind, Randomized Controlled Trial; Presentation at the American Society of Clinical Psychopharmacology Annual Meeting, May 27-30, 2025.
GH Research, Data for Spravato ® (esketamine), 2025.
Belser et al., Patient Experiences of Psilocybin-Assisted Psychotherapy: An Interpretative Phenomenological Analysis, Journal of Humanistic Psychology, 2017, 57 (4), p. 354-388.
Beliveau et al., A High-Resolution *In Vitro* Atlas of the Human Brain's Serotonin System, The Journal of Neuroscience, 2017, 37(1), p. 120-128.
Johnson & Johnson, "Spravato® (esketamine) approved in the U.S. as the first and only monotherapy for adults with treatment-resistant depression", Jan. 21, 2025, retrieved from https://www.jnj.com/media-center/press-releases/spravato-esketamine-approved-in-the-u-s-as-the-first-and-only-monotherapy-for-adults-with-treatment-resistant-depression.
Excerpt from US Internal Revenue Service database of non-profit organizations, retrieved on May 24, 2025, https://apps.irs.gov/app/eos/.
Office Action issued in PA 93611-01 (WO2020/169850) dated Jun. 10, 2025.
Office Action issued in JP 2024-208392 (WO 2020/169850), dated Dec. 1, 2025, translation.
Office Action issued in JP 2024-208395 (WO 2020/169851), dated Dec. 1, 2025, translation.
Office Action issued in AU 2021228914 (WO 2021/170614), dated Nov. 28, 2025.
Office Action issued in U.S. Appl. No. 18/373,903 dated Dec. 29, 2025.
Office Action issued in JP 2022-549753 (WO2021/170614), dated Dec. 23, 2025, translation.
Office Action issued in KR 10-2022-7033199 (WO2021/170614), dated Dec. 10, 2025, translation.
Office Action issued in U.S. Appl. No. 18/675,614 dated Jan. 12, 2026.
Notice of Opposition filed in EP 4349407 dated Jan. 9, 2026.
Submission under Rule 116 RPC filed in EP4313945 dated Jan. 2, 2026.
Office Action issued in U.S. Appl. No. 18/373,906 dated Jan. 27, 2026.
Office Action issued in U.S. Appl. No. 18/373,904 dated Feb. 6, 2026.
Office Action issued in CR2022-0000417 (WO2021/170614), dated Dec. 17, 2025, translation.
Examiner's Report issued in CA 3172772 (WO2021/170614), dated Jan. 9, 2026.
Reply from Opponent to Submission of Proprietor in EP3927337 (WO2020169850), dated Jan. 15, 2026.
Reply from Opponent to Submission of Proprietor in EP3927338 (WO2020169851), dated Jan. 20, 2026.
Anonymous ClinicalTrials, Study Details NCT05660642 An Open-Label Study to Evaluate the Safety, Tolerability and Pharmacodynamics of BPL-003 in Patients with Treatment-Resistant Depression, ClinicalTrials.gov, Nov. 28, 2025 (Nov. 28, 2025), XP093346249.
GH Research, "GH Research to Announce IND Status for GH001," dated Jan. 2, 2026.
Office Action issued in EP 24163006.0 (WO 2020/254584), dated Dec. 8, 2025.
Office Action issued in IL 289085 (WO2020/254584) dated Dec. 28, 2025.
Office Action issued in Co NC2022/0012059 (WO2020/254584) dated Dec. 29, 2025, translation.

* cited by examiner

RECRYSTALLISATION OF 5-METHOXY-N,N-DIMETHYL-TRYPTAMINE(5-MEO-DMT)

TECHNICAL FIELD

The present invention relates to a method of purifying an organic compound, specifically 5-Methoxy-N,N-dimethyltryptamine (5-MeO-DMT). The invention furthermore relates to 5-MeO-DMT in a form meeting specific purity requirements.

BACKGROUND

5-Methoxy-N,N-dimethyltryptamine (5-MeO-DMT) has the formula shown below.

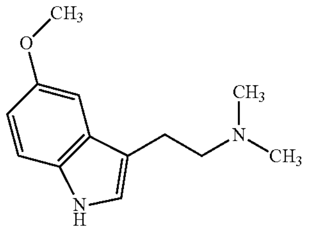

5-MeO-DMT

5-MeO-DMT is a naturally occurring serotonergic psychedelic tryptamine which acts as a 5-HT1A and 5-HT2A receptor agonist.

5-MeO-DMT is synthesized in human pineal and retina, and it has been found in human body fluids including urine, blood, and cerebrospinal fluid.

5-MeO-DMT was first isolated from the bark of *Dictyoloma incanescens*, but it is also contained in other plants, and it has been identified as the major active ingredient in the venom of *Bufo alvarius* toads.

The chemical synthesis of 5-MeO-DMT has been described in 1936 by Hoshino and Shimodaira (Bulletin of the Chemical Society of Japan, 11(3), 221-224). No medical or other use is contemplated in this publication.

According to Hoshino and Shimodaira, following a reaction between 5-methoxy indolyl 3-ethyl beta bromide and dimethyl amine the product is isolated and purified by distillation under reduced pressure. It is also reported that the substance crystallises from ether-petrol ether. No conditions are disclosed.

The product obtained is described as nice colorless prisms having a melting point of 66-67° C. There is no characterisation regarding the amounts of impurities contained in the product.

A comparison of the reported melting point with later data regarding the melting point of 5-MeO-DMT (69-70° C.) may, however, be taken as an indication that impurities are still present.

Moreover, given the high boiling point of 5-MeO-DMT even under reduced pressure (208 to 210° C. at 4 mm), distillation is not an advantageous purification method.

Somei et al. (Chem. Pharm. Bull. 49(1) 87-96 (2001)) report syntheses of serotonin, N-methylserotonin, bufotenine, 5-methoxy-N-methyltryptamine, bufobutanoic acid, N-(indol-3-yl)methyl-5-methoxy-N-methyltryptamine, and lespedamine.

In the context of a synthesis for bufotenine, a mixture of compounds comprising 5-MeO-DMT is obtained from which the components are purified by column chromatography. 5-MeO-DMT is then recrystallised from $Et_2O$-hexane. Details regarding the recrystallisation conditions or the amounts of impurities contained in the product are not disclosed. The liquid mixture used for recrystallisation ($Et_2O$-hexane) is similar to the mixture used by Hoshino and Shimodaira (ether-petrol ether).

Based on its physiological activities, there has recently been an interest in potential medical uses of 5-MeO-DMT, for instance, investigating potential medical uses in human clinical trials.

For such uses in human clinical trials, and for potential use in an approved medical product, 5-MeO-DMT in high purity is required. For administration to humans, purity as high as possible is necessary. According to the invention, it is in particular desirable that the total amount of impurities in the drug substance is below 0.5% and that the amount of each individual impurity is below 0.1%.

Furthermore, limits as regards the amount of residual solvent are to be observed.

Against this background, there is a need for providing a simple method of purifying 5-MeO-DMT, in particular of purifying 5-MeO-DMT so as to obtain the substance in a pharmaceutical grade. There is also a need for providing a 5-MeO-DMT in a form meeting specific purity requirements.

SUMMARY OF THE INVENTION

The present invention relates to a method of purifying 5-methoxy-N,N-dimethyltryptamine (5-MeO-DMT). The method comprises

- dissolving crude 5-MeO-DMT in a solvent at a temperature above room temperature;
- cooling the obtained solution to a temperature below room temperature to precipitate solid 5-MeO-DMT;
- separating the solid 5-MeO-DMT from the remaining solution;
- removing solvent from the crystalline 5-MeO-DMT;
- wherein the solvent comprises one or more ethers and less than 5 wt % of aliphatic hydrocarbons as anti-solvents.

The invention further provides a method comprising the steps as above, wherein the solvent comprises less than 5 wt % in total of any anti-solvents, wherein anti-solvent means a liquid in which the solubility of 5-MeO-DMT at any temperature occurring during the recrystallisation is less than 20% the solubility in the ether used, or, in case that more than one ether is used, in the combination of ethers present in the dissolution solvent.

The invention also provides 5-MeO-DMT in a form containing a total amount of impurities of below 0.5 area %, wherein the amount of each individual impurity is below 0.1 area %. The amounts of impurities are determined by chromatography as describes in detail below.

Specific embodiments are defined in the dependent claims.

DETAILED DESCRIPTION OF THE INVENTION

Figure 1:
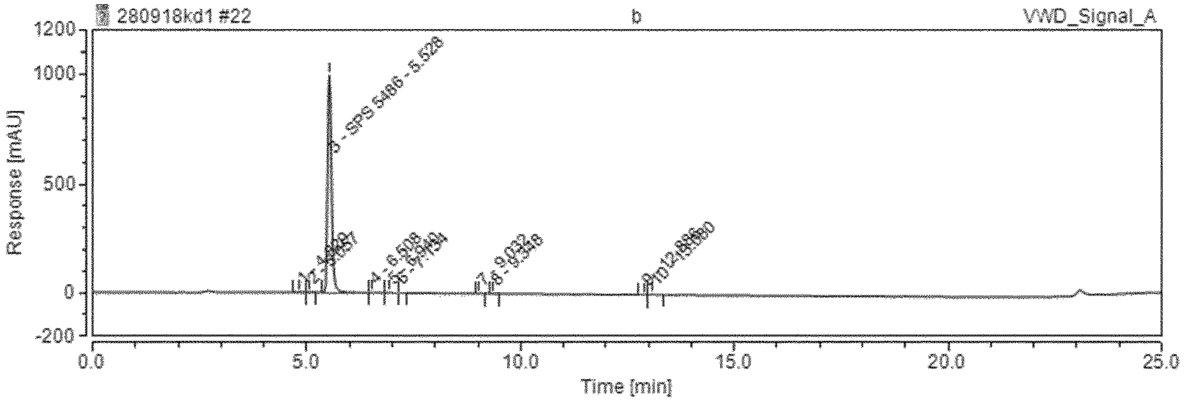
FIG. 1 shows an example chromatogram for a 5-MeO-DMT sample analysed by HPLC as described below.
Figure 2:
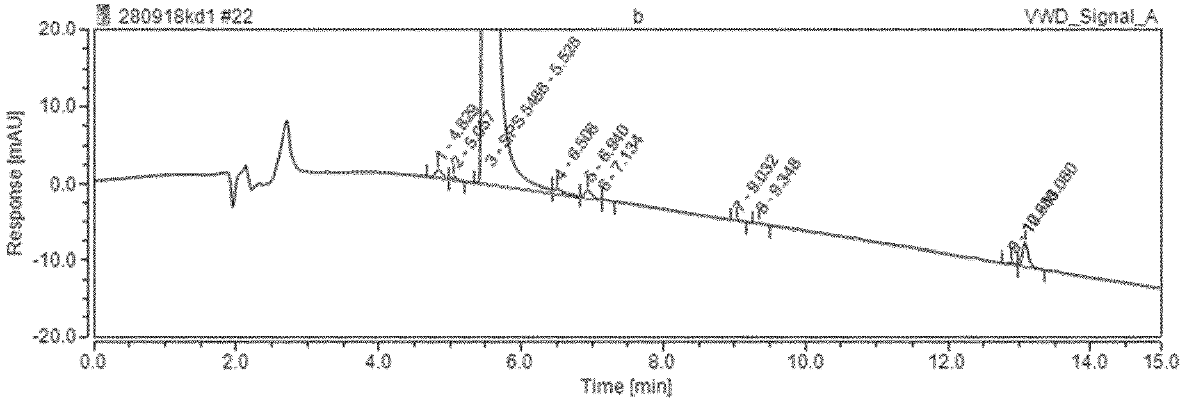
FIG. 2 shows an enhanced view of the example chromatogram.

The present invention is based on the discovery that 5-methoxy-N,N-dimethyltryptamine (5-MeO-DMT) can be purified to obtain the substance in a pharmaceutical grade by recrystallisation if specific conditions are observed.

5-MeO-DMT is available from natural sources as well as via synthetic methods. It is a white to off white, yellow or orange powder.

The preparation of 5-MeO-DMT by isolation from natural sources or by chemical synthesis as a rule yields a material (crude 5-MeO-DMT) still containing significant amounts of impurities so that the material is not suitable for pharmaceutical applications.

The crude 5-MeO-DMT will typically contain a total amount of impurities of 0.5% or more and may contain individual impurities in amounts of 0.1% or more.

Preferably, the crude 5-MeO-DMT used in the method of the invention does not contain more than 5% impurities in total, more preferably not more than 2% impurities in total.

While colouration of 5-MeO-DMT shows the presence of one or more impurities, it does not as such indicate whether or not a certain preparation meets the requirements for a pharmaceutical use.

The purity of a 5-MeO-DMT sample is analysed by HPLC. Individual impurities can be identified by their relative retention times (RRT). The detection method is UV detection at 227 nm.

A suitable column is a reversed-phase column, in particular an octadecyl carbon chain-bonded silica (C18) column.

For elution, a mixed solvent is used which is based on a mobile phase A (0.013M ammonium acetate in water) and a mobile phase B (acetonitrile). A specific gradient method is detailed in Example 1 below.

Percent values referring to purity are area %, based on the peak area in an HPLC chromatogram obtained as described above.

The present inventors have recognised that recrystallisation of crude 5-MeO-DMT in the form of the free base, despite its relatively low melting point, is a suitable approach to obtain 5-MeO-DMT in high purity, i.e., in a form having a purity such that the total amount of impurities is below 0.5% and the amount of each individual impurity is below 0.1%.

While 5-MeO-DMT may separate from a solution upon cooling in the form of an oil, the inventors have found that solvents comprising certain ethers can suitably be used to obtain a solid, in particular crystalline, form of 5-MeO-DMT having improved purity.

The recrystallisation solvent in particular comprises one or more ethers having a boiling point in the range of 40° C. to 100° C. under a pressure of 1 bar.

Suitable ethers are aliphatic and alicyclic ethers. These ethers in particular do not comprise any functional group besides the ether moiety.

Examples of suitable ethers (boiling points in brackets) include di-n-propylether (90° C.), di-iso-propylether (69° C.), methyl tert.-butyl ether (MTBE) (55° C.), ethyl tert.-butyl ether (ETBE) (73° C.), tert.-amyl methyl ether (TAME; 2-methoxy-2-methylbutan) (86° C.), dimethoxymethan (42.3° C.), diethoxymethan (88° C.), tetrahydrofuran (66° C.), (+/−)-tetrahydro-2-methylfuran (80° C.), tetrahydro-2,5-dimethylfuran (90-92° C.), tetrahydropyran (88° C.).

Preferably, the ether has a boiling point in the range of 50° C. to 80° C. under a pressure of 1 bar.

Examples of preferred ethers are methyl tert.-butyl ether (MTBE), ethyl tert.-butyl ether (ETBE), and diisopropyl ether. The most preferred ether is methyl tert.-butyl ether (MTBE).

The recrystallisation solvent contains at least 50%, preferably at least 70% and in particular at least 90% of one or more ethers, in particular of one or more ethers having a boiling point in the range of 40° C. to 100° C. under a pressure of 1 bar, especially of one or more of the ethers specifically identified above. These % values are intended to designate wt %, based on the total weight of the solvent.

While other solvents may be present besides the one or more ethers, the recrystallisation solvent contains less than 5%, preferably less than 2%, more preferably less than 1%, of aliphatic hydrocarbons as anti-solvents and in particular contains no aliphatic hydrocarbons. Preferably, these limitations apply to any hydrocarbon.

The above % values are intended to designate wt %, based on the total weight of the recrystallisation solvent, including hydrocarbon anti-solvents.

Further, preferably, while other solvents may be present besides the one or more ethers, the recrystallisation solvent contains less than 5%, preferably less than 2%, more preferably less than 1%, of any anti-solvents and in particular contains no anti-solvent. These % values are intended to designate wt %, based on the total weight of the recrystallisation solvent, including anti-solvents.

If more than one anti-solvent is present, the limitations set out above for the anti-solvent relate to the total amount of all anti-solvents present.

Minor amounts of certain anti-solvents may be present in commercially available solvents, such as commercially available ethers.

Preferably no anti-solvent is added in the method of the invention.

The term anti-solvent as used herein refers to a liquid in which the solubility of 5-MeO-DMT at any temperature occurring during the recrystallisation is less than 20% the solubility in the ether used, or, in case that more than one ether is used, in the combination of ethers present in the dissolution solvent. The solubility is expressed in mg/mL.

Typical anti-solvents include hydrocarbons, such as aliphatic hydrocarbons, like petrol ether, heptanes, hexanes; and water.

In a preferred embodiment, the recrystallisation solvent contains at least 50%, preferably at least 70% and in particular at least 90% of MTBE. In a specific embodiment, the recrystallisation solvent contains at least 98% MTBE. The % values are intended to designate wt %, based on the total weight of the solvent.

In a further preferred embodiment, 5-MeO-DMT is purified by recrystallisation in 98 wt % MTBE without adding a hydrocarbon as an anti-solvent.

The method of the invention involves dissolving crude 5-MeO-DMT in the recrystallisation solvent. The 5-MeO-DMT will be dissolved in the recrystallisation solvent at a dissolution temperature above room temperature up to the boiling point of the solvent.

Room temperature means a temperature in the range of 20 to 25° C. Above room temperature means above 25° C., below room temperature below 20° C.

In one embodiment, the 5-MeO-DMT will be dissolved in the recrystallisation solvent at a dissolution temperature in the range of 35 to 40° C.

The amount of recrystallisation solvent used is an amount sufficient to achieve complete dissolution at the dissolution temperature.

For instance, an at least 25% saturated solution is achieved. In one embodiment, the amount is sufficient to achieve a saturated solution at the dissolution temperature.

Preferably an at least 50% and at most 90% saturated solution is achieved.

After dissolution has occurred, the solution will be cooled to a temperature below room temperature (i.e., below 20° C.) to allow crystallisation of the 5-MeO-DMT. A suitable temperature range is 0 to 20° C. In one embodiment, the temperature is in the range of 7 to 12° C.

The product obtained can be recovered by filtration.

The recrystallisation may be repeated one or more times to improve purity.

The purification according to the present invention preferably does not involve a column chromatography step. Further, the purification according to the present invention does preferably not involve a step of distillation of 5-MeO-DMT.

From the product recovered residual solvent can, at least in part, be removed under reduced pressure. The weight amount of solvent in the product is NMT 5000 ppm, preferably NMT 2500 ppm, more preferably NMT 500 ppm and in particular NMT 100 ppm.

The method of the invention allows reducing the amount of impurities. It in particular allows reducing the total amount of impurities in a 5-MeO-DMT sample to below 0.5% and reducing the amount of each individual impurity in a 5-MeO-DMT sample to below 0.1%. These % values are area % determined by HPLC as indicated above. At the same time, low amounts of residual solvent can be achieved.

Thus, according to one aspect of the invention, 5-MeO-DMT is provided in a form containing a total amount of impurities of below 0.5 area %, wherein the amount of each individual impurity is below 0.1 area %. The amounts of impurities are determined by HPLC carried out with an octadecyl carbon chain-bonded silica (C18) column and a mixed solvent based on 0.013M ammonium acetate in water and acetonitrile as eluent, using UV detection at 227 nm.

5-MeO-DMT is provided in a form preferably having a residual solvent content of not more than 5000 ppm, preferably not more than 2500 ppm, more preferably not more than 500 ppm and in particular not more than 100 ppm.

The following examples are intended to further illustrate the invention.

EXAMPLES

Example 1—Analytical Method

The purity of 5-MeO-DMT is determined by HPLC.

Method Parameters

Instrument: A suitable HPLC system equipped with UV detection, linked to the laboratory data handling system
Column: ACE C18 (150×4.6×3 μm)
Injection Volume: 5 μl
Flow Rate: 0.75 ml/minute
Detector: UV at 227 nm
Run Time: 25 minutes
Column Temperature: 30° C.
Diluent: Methanol
Mobile Phase A: 0.013M Ammonium acetate in water
Mobile Phase B: Acetonitrile

Gradient

| Time (minutes) | Vol.-% Mobile Phase A | Vol.-% Mobile Phase B |
|---|---|---|
| 0.0 | 80 | 20 |
| 18.0 | 26 | 74 |
| 20.0 | 26 | 74 |
| 20.1 | 80 | 20 |
| 25.0 | 80 | 20 |

The typical retention time of 5-MeO-DMT is 5.5 min.

Sample Preparation (In Duplicate)

Accurately weigh 12-18 mg of sample into 100 ml volumetric flask and make to volume with methanol. Mix well.

Validation of Analytical Procedures

The HPLC method used was tested for linearity and precision. IR, NMR, GC-Headspace, KF and ICP-MS are common techniques, being applied according to routine procedures. Based on the results, the methods are considered as fit for purpose.

Linearity of the HPLC Method

A stock solution of 5-MeO-DMT was prepared in methanol. A nominal concentration of 0.15 mg/ml was taken.

| % Nominal | Actual concentration (mg/ml) | Peak Area Injection 1 | Injection 2 | mean | % RD |
|---|---|---|---|---|---|
| 150 | 0.226 | 132.511 | 134.435 | 133.473 | 1.4 |
| 125 | 0.181 | 109.305 | 108.094 | 108.700 | −1.1 |
| 100 | 0.151 | 91.466 | 92.675 | 92.070 | 1.3 |
| 80 | 0.121 | 73.543 | 72.295 | 72.919 | −1.7 |
| 50 | 0.075 | 46.871 | 46.891 | 46.881 | 0.0 |
| 25 | 0.038 | 23.965 | 24.056 | 24.011 | 0.4 |
| 10 | 0.015 | 9.675 | 9.706 | 9.690 | 0.3 |
| 5 | 0.008 | 4.670 | 4.694 | 4.682 | 0.5 |
| 1 | 0.000 | 0.982 | 0.989 | 0.985 | 0.7 |
| 0.1 | 0.002 | 0.468 | 0.472 | 0.470 | 0.8 |
| 0.01 | 0.000 | 0.097 | 0.095 | 0.096 | −2.1 |

All duplicate injections were within ±2%.

Figure 3:
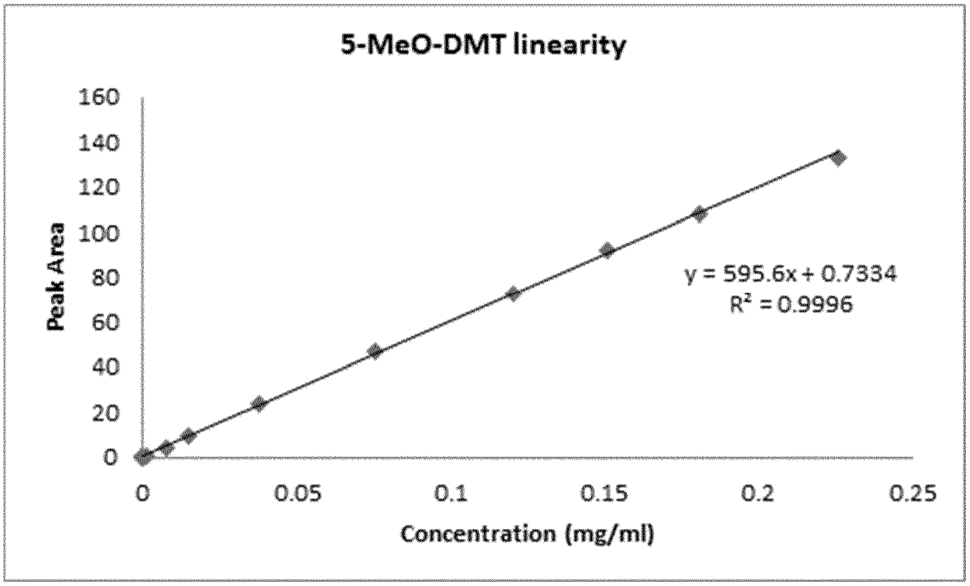
FIG. 3 is a diagram obtained by plotting the peak area, determined by HPLC, vs the concentration of 5-MeO-DMT in the analysed sample.

Y intercept % at nominal concentration was determined to be 0.8%. Method is deemed linear, as seen in FIG. 3.

Precision of the HPLC Method

Six sample solutions were prepared at nominal concentration (12-18 mg in 100 ml methanol). The purity results were as follows:

| Precision | Purity (% area) |
|---|---|
| 1 | 99.21 |
| 2 | 99.02 |
| 3 | 99.18 |

-continued

| Precision | Purity (% area) |
|---|---|
| 4 | 99.21 |
| 5 | 99.17 |
| 6 | 99.17 |
| Average | 99.16 |
| SD | 0.07 |
| RSD (%) | 0.07 |

Acceptance criteria for purity values across the six samples would be 1% RSD, the actual reading was 0.07%. Therefore, the analytical method is considered to exhibit adequate precision.

Example 2—Solvent Screen

A solubility screen of 5-MeO-DMT was performed on a number of solvents at both room temperature and reflux.

The screen involved adding a solvent to 200 mg of 5-MeO-DMT until complete dissolution was obtained, unless the compound had such a low solubility in the solvent that no complete dissolution of the sample was achieved in 4 ml solvent (solubility less than 0.05 mg/ml).

The results of the solubility screen are shown in the table below.

| | 5-MeO-DMT Solubility | | | |
|---|---|---|---|---|
| Solvent | Ambient (g/mL) | Ambient (vols.) | Reflux (g/mL) | Reflux (vols.) |
| Acetone | 0.53 | 1.9 | — | — |
| Ethanol | 0.34 | 2.9 | — | — |
| Ethyl Acetate | 0.26 | 3.9 | — | — |
| 2-Methyltetrahydrofuran (2-MeTHF) | 0.25 | 4.0 | — | — |
| Isopropyl acetate (IPAc) | 0.21 | 4.8 | — | — |
| Toluene | 0.2 | 5.1 | — | — |
| Isopropanol (IPA) | 0.18 | 5.6 | — | — |
| Methyl tert-butyl ether (MTBE) | <0.05 | >20 | 0.42 | 2.4 |
| Heptanes | <0.05 | >20 | <0.05 | >20 |
| Water | <0.05 | >20 | <0.05 | >20 |

The results from the solubility screen indicated that 5-MeO-DMT was very soluble in a number of solvents at room temperature. Poor solubility was observed in water and heptanes.

5-MeO-DMT was not observed to be soluble in MTBE at room temperature but was very soluble when the temperature of the solvent was increased. However, MTBE was not considered a suitable recrystallisation solvent as upon cooling of the hot MTBE solution to room temperature no crystallisation was observed.

Example 3—Initial Attempts at Recrystallisation

Following the results of the solubility study a number of experiments were performed with the aim of recrystallising 5-MeO-DMT from a mixture of isopropanol (IPA) and either heptanes or water. The aim was to dissolve 5-MeO-DMT in IPA before adding water or heptanes as the anti-solvent to afford precipitation/crystallisation. IPA was used in order to maximise recovery of the recrystallised 5-MeO-DMT as although 5-MeO-DMT was found to be very soluble in IPA at room temperature, 5-MeO-DMT was less soluble in IPA than in the other solvents evaluated.

In the first small scale experiment 5-MeO-DMT (200 mg) was dissolved in the minimum amount of IPA (0.3 mL, 1.5 volumes) required to achieve complete dissolution at 80° C. After cooling the solution to room temperature no crystallisation was observed, however. Therefore, heptanes were added dropwise with the aim of precipitating 5-MeO-DMT from solution. Unfortunately, upon the addition of heptanes 5-MeO-DMT was found to oil rather than precipitate. Oiling also occurred when the experiment was repeated using water as the anti-solvent in place of heptanes.

In a second attempt at crystallisation from an IPA and water or heptanes mixture the solvent additions were reversed in an attempt to stop oiling. 9.5 volumes (1.9 mL) of heptanes were charged to 5-MeO-DMT (200 mg) before the resulting slurry was warmed to 80° C. IPA (2.1 volumes, 0.4 mL) was charged dropwise until complete dissolution was observed. Upon cooling to room temperature, however, the material did not crystallise. An attempt with water (9.5 volumes, 1.9 mL) and IPA (5.3 volumes, 1 mL) also resulted in a lack of crystallisation upon cooling to room temperature.

To investigate whether crystallisation could be achieved using a reduced volume of the solvent mixtures a 17% IPA in heptanes solution (9.4 volumes, 1.9 mL) was added dropwise to 5-MeO-DMT (200 mg), at 80° C., until all material was completely dissolved. Unfortunately, after cooling, oiling was observed. Oiling also occurred when a 34% IPA in water (10.7 volumes) was added to 5-MeO-DMT (200 mg) at 80° C.

The previously described experiments utilising the 17% IPA in heptanes and 34% IPA in water solutions were repeated at 60° C. Unfortunately, in both cases oiling was observed upon cooling.

A further final small-scale experiment using a solvent in which 5-MeO-DMT has greater solubility was carried out. Ethanol (0.5 volumes, 0.1 mL) was charged to 5-MeO-DMT (200 mg) at 60° C. before water was added dropwise. However, upon addition of water to the batch oiling of 5-MeO-DMT was observed.

Table 2 below displays a summary of the small scale recrystallisation trials described above.

| Experiment | 5-MeO-DMT charge | Solvent | Anti-solvent | Comments |
|---|---|---|---|---|
| IPA added until dissolution achieved at 80° C. | 200 mg | IPA | Heptanes | Oiling out during dropwise addition of heptanes |
| Anti-solvent charged once dissolution achieved | 200 mg | IPA | Water | Oiling out during dropwise addition of water |
| IPA charged to slurry of 5-MeO-DMT in anti-solvent at 80° C. to achieve complete dissolution | 200 mg | IPA | Heptanes | Complete dissolution achieved but no crystallisation upon cooling |
| | 200 mg | IPA | Water | Complete dissolution achieved but no crystallisation upon cooling |

-continued

| Experiment | 5-MeO-DMT charge | Solvent | Anti-solvent | Comments |
|---|---|---|---|---|
| Mixture of IPA in anti-solvent charged to 5-MeO-DMT at 80° C. to achieve complete dissolution | 200 mg | IPA | Heptanes | Complete dissolution achieved but oiling out upon cooling |
| | 200 mg | IPA | Water | Complete dissolution achieved but oiling out upon cooling |
| Mixture of IPA in anti-solvent charged to 5-MeO-DMT at 60° C. to achieve complete dissolution | 200 mg | IPA | Heptanes | Complete dissolution achieved but oiling out upon cooling |
| | 200 mg | IPA | Water | Complete dissolution achieved but oiling out upon cooling |
| Ethanol added until dissolution achieved at 60° C. Anti-solvent charged once dissolution achieved | 200 mg | Ethanol | Water | Oiling out during dropwise addition of water |

Example 4—Crystallisation After Heating and Oiling

In an attempt to avoid 5-MeO-DMT oiling out during crystallisation a larger scale experiment was performed. With the increased scale, greater control over the anti-solvent charge was expected, allowing more careful addition, potential determination of the cloud point and the avoidance of oiling. 5-MeO-DMT (2.0 g) was warmed to 60° C. before being dissolved in the minimum amount of IPA (0.8 mL, 0.4 volumes) required to achieve complete dissolution. After cooling to room temperature no crystallisation was observed and so the batch was warmed back to 60° C. Water was added dropwise until the solution became cloudy. Unfortunately, no cloud point was determined because of 5-MeO-DMT oiling from solution without the solution becoming cloudy.

In order to determine whether it was possible to still crystallise 5-MeO-DMT, despite it oiling from solution, the solvent was removed by evaporation to yield an orange oil. After cooling the oil in a fridge overnight an orange crystalline solid was obtained. This result indicated that although crystallisation of 5-MeO-DMT was slow it was still possible to crystallise 5-MeO-DMT even after heating and oiling.

Example 5—Larger Scale Crystallisation Attempts Using MTBE/Heptanes

Due to the issues encountered when using a solvent mixture of either IPA or ethanol in heptanes or water, a solvent system utilising MTBE was reinvestigated.

Previously crystallisation from MTBE was not observed following cooling to room temperature. Therefore, in the second attempt at crystallisation, from MTBE, the solution was further cooled to 0 to 5° C.

MTBE (1 mL, 0.5 volumes) was charged to the crystalline solid at 45 to 50° C. until complete dissolution was achieved. This MTBE charge was lower than the 2.4 volumes stated previously and is likely due to the small scale that the solvent screen was performed at.

Following dissolution, the batch was cooled to 0 to 5° C. over 40 minutes to yield a very thick viscous solution that did afford crystallisation.

The batch was warmed back to 45 to 50° C. and then cooled to room temperature over 1 hour. After stirring at room temperature for 30 minutes the batch became a very thick viscous solution and so a further 0.4 mL (0.2 volumes) of MTBE was charged before the batch was stirred for a further 15 minutes. Following the stirring a thin slurry was obtained.

Heptanes (0.7 mL, 0.35 volumes) were charged dropwise and then the batch was stirred for an additional 15 minutes resulting in a thicker slurry. The batch was cooled to 0 to 5° C. and heptanes (0.7 mL, 0.35 volumes) were subsequently charged dropwise. Once filtered the isolated solids were washed with cold heptanes (2×2 mL) before being dried under vacuum overnight to yield a pale orange solid. The isolated solid (1.44 g, 72% recovery) was analysed by HPLC for purity.

Experimental conditions are summarised in Table 3. The results of the analysis are shown in Table 4.

Example 6—Crystallisation Utilising MTBE/Heptanes

A second experiment utilising MTBE/heptanes was performed. 5-MeO-DMT (2.0 g) was dissolved in MTBE (1.4 mL, 0.7 volumes) at 45 to 50° C. before being cooled to room temperature over 70 minutes. Upon crystallisation stirring stopped and so the batch was warmed back to 45 to 50° C. and additional MTBE (1 mL, 0.5 volumes) was charged. After cooling back to room temperature and stirring out the resulting slurry was diluted with heptanes (1 mL, 0.5 volumes). Upon heptanes addition a large amount of material was observed to coat the vessel wall and so to try and remove this material a further amount MTBE (1 mL, 0.5 volumes) was charged. After stirring for 90 minutes at room temperature the batch was filtered then washed sequentially with MTBE:heptanes (2:1, 1 mL, 0.5 volumes) and heptanes (1 mL, 0.5 volumes). After drying a pale orange solid was obtained in 1.13 g (57% recovery). The isolated material was analysed for purity by HPLC.

Experimental conditions are summarised in Table 3. The results of the analysis are shown in Table 4.

Example 7—Crystallisation Utilising MTBE/Heptanes

5-MeO-DMT (2.0 g) was dissolved in MTBE (2 mL, 1.0 volume) at 45 to 50° C. before being cooled to room temperature over 1 hour. After stirring out at room temperature for 1.5 hours the resulting slurry was diluted with MTBE (2×1 mL, 1.0 volume) over 20 minutes. Heptanes (1 mL, 0.5 volumes) were then charged over 5 minutes before the batch was stirred at room temperature for 2 hours. After cooling to 8 to 12° C. over 10 minutes the batch was stirred for 15 minutes at 8 to 12° C. before being diluted with more heptanes (1 mL, 0.5 volumes). After an additional 10 minutes stir out at 8 to 12° C. the batch was cooled to 0 to 5° C. over 10 minutes then stirred out for a further 15 minutes. Heptanes (2 mL, 1.0 volume) were then charged over 5 minutes before the batch was stirred at 0 to 5° C. for 1 hour. The batch was filtered and washed with MTBE:heptanes (1:1, 2 mL, 1.0 volume). After drying a pale orange solid was obtained in 1.37 g (69% recovery). The isolated solid was analysed for purity by HPLC.

Experimental conditions are summarised in Table 3. The results of the analysis are shown in Table 4.

Example 8—Crystallisation from MTBE

In order to try and further increase the purity of the recrystallised material an experiment was performed using only MTBE as the solvent. 5-MeO-DMT (2.0 g) was dissolved in MTBE (4 mL, 2.0 volumes) at 35 to 40° C. before being cooled to room temperature over 30 minutes. After stirring at room temperature for 50 minutes no crystallisation was observed, therefore, the batch temperature was decreased to 7 to 12° C. over 30 minutes. After stirring at 7 to 12° C. for 10 minutes crystallisation occurred. The batch was subsequently filtered following a 1 hour stir out at 7 to 12° C. After washing with MTBE (1 mL, 0.5 volumes), at 7 to 12° C., the batch was pulled dry under vacuum for 3.5 hours to yield a pale orange solid in 1.02 g (50% recovery). The isolated solid was analysed for purity by HPLC.

Experimental conditions are summarised in Table 3. The results of the analysis are shown in Table 4.

Table 3 below displays a summary of the conditions of the larger scale attempts at recrystallisation of 5-MeO-DMT.

| | Example 5 | Example 6 | Example 7 | Example 8 |
|---|---|---|---|---|
| Input (g) | 2.00 | 2.00 | 2.00 | 2.0 |
| MTBE:heptanes ratio | 1:1 | 4:1 | 1:1 | No heptanes |
| Total solvent volume (mL) | 2.8 | 4.4 | 8.0 | 4.0 |
| Total solvent volume (vols.) | 1.2 | 2.2 | 4.0 | 2.0 |
| Isolation temperature (° C.) | 0-5 | 20-25 | 0-5 | 7-12 |
| Recovery (g) | 1.44 | 1.13 | 1.37 | 1.02 |
| Recovery (%) | 72 | 57 | 69 | 50 |
| Purity (% area) | 99.61 | 99.58 | 99.45 | 99.74 |

Table 4 below displays impurity profiles of materials isolated from recrystallisation experiments.

| Impurity Profile | | HPLC Purity (area %) | | | | |
|---|---|---|---|---|---|---|
| | RRT | Raw Material | Example 5 | Example 6 | Example 7 | Example 8 |
| | 0.87 | 0.07 | — | 0.02 | 0.02 | 0.06 |
| | 0.90 | 0.04 | 0.08 | 0.05 | 0.06 | 0.02 |
| | 0.92 | 0.03 | 0.02 | 0.02 | 0.02 | — |
| 5-MeO-DMT | 1.00 | 99.21 | 99.61 | 99.58 | 99.45 | 99.74 |
| | 1.18 | 0.13 | 0.03 | 0.11 | 0.14 | 0.04 |
| | 1.24 | 0.15 | 0.06 | 0.07 | 0.05 | 0.02 |
| | 1.28 | 0.02 | — | — | 0.01 | <0.01 |
| | 1.64 | — | — | — | 0.01 | 0.02 |
| | 1.67 | — | — | — | — | <0.01 |
| | 1.72 | — | — | — | 0.02 | — |
| | 1.96 | 0.02 | — | — | 0.01 | — |
| | 2.08 | — | — | — | 0.01 | — |
| | 2.11 | — | — | — | 0.01 | — |
| | 2.34 | 0.03 | 0.02 | 0.03 | 0.03 | — |
| | 2.38 | 0.29 | 0.19 | 0.13 | 0.14 | 0.08 |
| | 2.42 | — | — | — | 0.01 | — |
| | 2.61 | — | — | — | <0.01 | — |
| | 2.76 | 0.01 | — | — | 0.01 | — |
| | 2.82 | — | — | — | 0.01 | — |
| | 2.90 | — | — | — | <0.01 | — |

A summary of the conditions used in the each of the larger scale recrystallisation experiments is shown in Table 3. The results from the analysis indicated that in all cases the overall purity of the material was increased and the impurity at RRT 1.24 was purged to below 0.10%. The impurity at RRT 2.38 was also reduced in all three experiments however but only below the target of NMT 0.10% in the experiment according to Example 8. The impurity at RRT 1.18 was only purged using the experimental conditions according to Example 5 and according to Example 8. Based upon these results it appears the most suitable conditions for achieving material in which all impurities are below 0.10% are from the experiment according to Example 8. Solvent analysis of sample according to Example 8 indicated an MTBE level of 17 ppm against an expected limit of NMT 5000 ppm.

The invention claimed is:

1. A method of purifying 5-methoxy-N,N-dimethyltryptamine (5-MeO-DMT) comprising:

dissolving crude 5-MeO-DMT in a recrystallisation solvent at a temperature above room temperature to obtain a solution;

cooling the obtained solution to a temperature below room temperature to precipitate a solid, the solid comprising crystalline 5-MeO-DMT;

separating the crystalline 5-MeO-DMT from the remaining solution; and removing the recrystallisation solvent from the crystalline 5-MeO-DMT to obtain a purified 5-MeO-DMT product;

wherein the recrystallisation solvent contains at least 98 wt % methyl tert.-butyl ether (MTBE).

2. The method according to claim 1, wherein the recrystallisation solvent contains less than 2 wt % aliphatic hydrocarbons.

3. The method according to claim 2, wherein the recrystallisation solvent contains less than 1 wt % aliphatic hydrocarbons.

4. The method according to claim 1, wherein the recrystallisation solvent comprises less than 2 wt % in total of any anti-solvents, wherein an anti-solvent is a liquid in which a solubility of 5-MeO-DMT at any temperature occurring during the recrystallisation is less than 20% of the solubility in the recrystallisation solvent used to dissolve the crude 5-MeO-DMT.

5. The method according to claim 4, wherein the recrystallisation solvent contains less than 1 wt % of anti-solvents.

6. The method according to claim 1, wherein the obtained solution is cooled to a temperature of 0 to 20° C.

7. The method according to claim 6, wherein the temperature is 7 to 12° C.

8. The method according to claim 1, wherein the purifying of the crude 5-MeO-DMT to form the purified 5-MeO-DMT product results in a total amount of impurities being reduced to below 0.5 area % as determined by HPLC using UV detection at 227 nm, and/or an amount of each individual impurity being reduced to below 0.1 area % as determined by HPLC using UV detection at 227 nm.

9. The method according to claim 8, wherein the HPLC is carried out with an octadecyl carbon chain-bonded silica (C18) column and a mixed solvent based on 0.013M ammonium acetate in water and acetonitrile as eluent.

10. The method according to claim 1, wherein an amount of residual solvent in the purified 5-MeO-DMT product is not more than 5000 ppm.

11. A method of purifying 5-methoxy-N,N-dimethyltryptamine (5-MeO-DMT) comprising:

dissolving crude 5-MeO-DMT in a recrystallisation solvent at a temperature above room temperature to form a mother liquor, wherein the crude 5-MeO-DMT contains a total amount of impurities of 0.5 area % to 5 area %, based on peak area in an HPLC chromatogram;

cooling the mother liquor to a temperature below room temperature to precipitate a solid, the solid comprising crystalline 5-MeO-DMT;

separating the crystalline 5-MeO-DMT from the mother liquor; and after the separation of the crystalline 5-MeO-DMT from the mother liquor, removing any remaining recrystallisation solvent from the crystalline 5-MeO-DMT to obtain a crystalline 5-MeO-DMT product in which the total amount of impurities in the crystalline 5-MeO-DMT product is below 0.5 area % and the amount of each individual impurity is below 0.1 area %;

wherein the recrystallisation solvent contains at least 98 wt % methyl tert.-butyl ether (MTBE), and the crystalline 5-MeO-DMT product is generated from the crude 5-MeO-DMT without performing column chromatography.

12. The method according to claim 11, wherein the 5-MeO-DMT is purified without adding a hydrocarbon as an anti-solvent.

13. The method according to claim 11, wherein the 5-MeO-DMT of the crude 5-MeO-DMT is in a free base form.

14. The method according to claim 11, wherein the crystalline 5-MeO-DMT product is generated from the crude 5-MeO-DMT without performing a distillation of 5-MeO-DMT.

15. A method of purifying 5-methoxy-N,N-dimethyltryptamine (5-MeO-DMT) comprising:

dissolving crude 5-MeO-DMT in a recrystallisation solvent at a temperature above room temperature to obtain a solution;

performing a recrystallization by cooling the obtained solution to a temperature below room temperature to precipitate a solid, the solid comprising crystalline 5-MeO-DMT;

separating the crystalline 5-MeO-DMT from the remaining solution; and removing the recrystallisation solvent from the crystalline 5-MeO-DMT to obtain a purified 5-MeO-DMT product in which an amount of each individual impurity in the purified 5-MeO-DMT product is below 0.1 area %, the amount of each individual impurity being determined by HPLC carried out with an octadecyl carbon chain-bonded silica (C18) column and a mixed solvent based on 0.013M ammonium acetate in water and acetonitrile as eluent, using UV detection at 227 nm; wherein the recrystallisation solvent contains at least 98 wt % methyl tert.-butyl ether (MTBE), and the purified 5-MeO-DMT product is obtained by performing the recrystallization only once.

* * * * *